(12) United States Patent
Kato et al.

(10) Patent No.: US 10,544,425 B2
(45) Date of Patent: Jan. 28, 2020

(54) PLANT HAVING INCREASED RESISTANCE OR SUSCEPTIBILITY TO 4-HPPD INHIBITOR

(75) Inventors: Hiroshi Kato, Tsukuba (JP); Hideo Maeda, Tsukuba (JP); Yoshihiro Sunohara, Tsukuba (JP); Ikuo Ando, Tsukuba (JP); Masahiro Oshima, Tsukuba (JP); Motoshige Kawata, Tsukuba (JP); Hitoshi Yoshida, Tsukuba (JP); Sakiko Hirose, Tsukuba (JP); Makiko Kawagishi, Tsukuba (JP); Yojiro Taniguchi, Tsukuba (JP); Kazumasa Murata, Toyama (JP); Hiroaki Maeda, Toyama (JP); Yuji Yamada, Tokyo (JP); Keisuke Sekino, Tokyo (JP); Akihiko Yamazaki, Tokyo (JP)

(73) Assignees: Incorporated Administrative Agency National Agriculture Agriculture and Food Research Organization, Ibaraki (JP); TOYAMA PREFECTURE, Toyama-shi (JP); SDS BIOTECH K.K., Tokyo (JP)

( * ) Notice: Subject to any disclaimer, the term of this patent is extended or adjusted under 35 U.S.C. 154(b) by 953 days.

(21) Appl. No.: 13/976,526

(22) PCT Filed: Dec. 26, 2011

(86) PCT No.: PCT/JP2011/080105
§ 371 (c)(1),
(2), (4) Date: Oct. 7, 2013

(87) PCT Pub. No.: WO2012/090950
PCT Pub. Date: Jul. 5, 2012

(65) Prior Publication Data
US 2015/0047066 A1 Feb. 12, 2015

(30) Foreign Application Priority Data
Dec. 28, 2010 (JP) ................................. 2010-293451

(51) Int. Cl.
C12N 15/82 (2006.01)
C12Q 1/6895 (2018.01)

(52) U.S. Cl.
CPC ....... *C12N 15/8274* (2013.01); *C12Q 1/6895* (2013.01)

(58) Field of Classification Search
CPC . C12N 15/8274; C12N 9/0004; C12Q 1/6895
See application file for complete search history.

(56) References Cited

U.S. PATENT DOCUMENTS

| 6,353,159 | B1 * | 3/2002 | Skillings | A01H 5/10 435/412 |
| 2004/0123343 | A1 * | 6/2004 | La Rosa | C07K 14/415 800/278 |

(Continued)

FOREIGN PATENT DOCUMENTS

| JP | 200129080 A | 2/2001 |
| JP | 2005185101 A | 7/2005 |

(Continued)

OTHER PUBLICATIONS

Friedberg, Iddo. "Automated protein function prediction—the genomic challenge." Briefings in bioinformatics 7.3 (2006): 225-242.*

(Continued)

*Primary Examiner* — Weihua Fan
(74) *Attorney, Agent, or Firm* — Sughrue Mion, PLLC

(57) ABSTRACT

By a QTL analysis and so forth using 4-HPPD inhibitor-susceptible rice and 4-HPPD inhibitor-resistant rice, a hypothetical gene (HIS1 gene) of an iron/ascorbate-dependent oxidoreductase gene located on a short arm of chromosome 2 of rice has been identified as a 4-HPPD inhibitor-resistance (Continued)

gene. Further, it has also been revealed that a homologous gene (HSL1 gene) of the HIS1 gene is located on chromosome 6 of rice. Furthermore, it has been found out that utilizations of these genes make it possible to efficiently produce a plant having increased resistance or susceptibility to a 4-HPPD inhibitor and to efficiently determine whether a plant has resistance or susceptibility to a 4-HPPD inhibitor.

16 Claims, 20 Drawing Sheets

Specification includes a Sequence Listing.

(56) References Cited

U.S. PATENT DOCUMENTS

| | | | | |
|---|---|---|---|---|
| 2006/0123505 | A1* | 6/2006 | Kikuchi | C07K 14/415 800/278 |
| 2006/0282911 | A1* | 12/2006 | Bull | A01H 1/02 800/266 |
| 2009/0011936 | A1* | 1/2009 | Hawkes | C12N 9/0077 504/136 |
| 2011/0039706 | A1* | 2/2011 | Busch | C12N 9/0069 504/348 |
| 2014/0018241 | A1* | 1/2014 | Sammons | A01N 63/02 504/128 |

FOREIGN PATENT DOCUMENTS

| | | |
|---|---|---|
| WO | 2008034648 A1 | 3/2008 |
| WO | 2008150473 A2 | 12/2008 |

OTHER PUBLICATIONS

GOWAN_Industry Product Updates, retrieved from www.laca1.org/presentations/2015/IUR/Industry%20Product%20Updates-Gowan%20USA-Craig%20Sandowski.pdf.*

Kawahara, Y., et al, 2013. Improvement of the *Oryza sativa* Nipponbare reference genome using next generation sequence and optical map data. Rice 6:4.*

Friedberg, I. "Automated protein function prediction—the genomic challenge." Briefings in bioinformatics 7.3 (2006): 225-242.*

Lang, N. T.,"Rice Breeding and Inheritance of Herbicide Resistance in Clearfield Rice (*Oryza sativa* L.)." Omonrice 15 (2007): 36-45.*

Friedberg, I. "Automated protein function prediction—the genomic challenge." Briefings in bioinformatics 7.3 (2006): 225-242 (Year: 2006).*

Luo, Ming, et al. "Expression and parent-of-origin effects for FIS2, MEA, and FIE in the endosperm and embryo of developing *Arabidopsis* seeds." Proceedings of the National Academy of Sciences 97.19 (2000): 10637-10642 (Year: 2000).*

Sutton, Peter, et al. "Activity of mesotrione on resistant weeds in maize." Pest management science 58.9 (2002): 981-984. (Year: 2002).*

Pawlowski, Wojciech P., and David A. Somers. "Transgene inheritance in plants genetically engineered by microprojectile bombardment." Molecular biotechnology 6.1 (1996): 17-30. (Year: 1996).*

Vain, P., et al. "Transgene behaviour in populations of rice plants transformed using a new dual binary vector system: pGreen/pSoup." Theoretical and Applied Genetics 107.2 (2003): 210-217. (Year: 2003).*

NCBI Reference Sequence NM_001053093.1, downloaded from Gen Bank Sep. 25, 2014.

Communication dated Nov. 16, 2015 from the Russian Intellectual Property Office in counterpart application No. 2013135291/10.

Tanaka et al., "Os06g0178100 [*Oryza sativa* Japonica Group]," NCBI Reference Sequence; NP_001174633.1 from Aug. 6, 2010; 3 pages total.

Akasaka et al., "Inheritance patterns for sensitivity of high-yielding rice varieties to benzobicycolon, 4-HPPD inhibitor", Ikushugaku Kenkyu, Mar. 2010, vol. 12, Supplementary vol. 1, p. 266.

International Preliminary Report on Patentability dated Jul. 10, 2013, issued in International Application No. PCT/JP2011/080105 to Incorporated Administrative Agency National Agriculture and Food Research Organization.

Wright et al., "Robust crop resistance to broadleaf and grass herbicides provided by aryloxyalkanoate dioxygenase transgenes", PNAS, 2010, 107(47):20240-20245.

Maruyama et al., "Forage rice and so forth are revealed to be susceptible to some herbicide", National Agriculture and Food Research Organization Agricultural Research Center, [online] Mar. 26, 2010, pp. 1-4, Press Release, [retrieved on Sep. 29, 2010], the Internet, URL:http://narc.naro.affrc.go.jp/press/h22/0326/index.htm>.

Sekino et al., "Sensitivity of Nineteen Varieties and Line of Forage Rice to Paddy Herbicide, Benzobicyclon," Japanese Journal of Crop Science, Mar. 25, 2009, 78(extra issue 1):120-121.

* cited by examiner

Fig. 19

SEQUENCE LISTING

```
<160> NUMBER OF SEQ ID NOS: 26

<210> SEQ ID NO 1
<211> LENGTH: 1729
<212> TYPE: DNA
<213> ORGANISM: Oryza sativa

<400> SEQUENCE: 1
ggctagctcc ccaagtcgaa acgtcgtcgc ccctcatcat ctcctcctcg ttgtcgcacc      60
cccaaccgca cgctgccgcc gctcgcttcc tcctctcctc gtctcactcc agaaagccaa     120
gctgcaaagc actatggcac atcccatagc aatggcagca tggacacaca gccatcggag     180
ccgaccgtgg taaaagcttt catcgcggtg cctgatatat cgacgccgac atcgagcacg     240
ccccaactcc atatgtattt gcaggctata gatgagctga aagatctcct ttcttttcaa     300
gcaagaacaa agttaagcaa gggaagatcc aagaacaaga acaccaatgg ctgacgagtc     360
atggagggcg ccggcgatag tgcaagagct ggcggcagcc ggcgtcgagg agccgccgag     420
ccgatacctg ctacgggaga aagaccgttc tgacgtcaag ctggtcgccg ccgagctgcc     480
ggagcccctc cccgtcgttg atctcagccg gctagatggt gccgaggagg ccaccaagct     540
```

-continued

```
cagggtggct ctgcagaatt ggggcttctt cctgcttacc aaccatggag tagaagcctc    600
tctgatggac agcgtgatga acttgtcgag agagtttttc aaccaaccaa tcgaacggaa    660
gcaaaaattc agcaacttga tcgatggcaa gaacttccag attcaagggt atggaactga    720
ccgggtggtt acccaagatc agatcctgga ctggtctgat cggttgcatc tcagagttga    780
acccaaggag gagcaagatc ttgccttctg gcctgaccat cctgaatctt tcagggatgt    840
tctgaacaag tatgcatcag gaaccaaaag aattagagac gatatcattc aggctatggc    900
caagcttctt gagcttgatg aggattactt cttggaccga ctcaacgaag ctcctgcatt    960
tgcaagattc aactactacc ctccctgtcc aaggcctgac cttgtgttcg gcatcaggcc   1020
tcactccgac ggcaccctct tgacgattct tctcgtcgac aaagatgtca gtggcctgca   1080
agttcagagg gatggcaagt ggtccaacgt tgaggcaact cctcacacat tgctgatcaa   1140
cttaggtgac accatggagg taatgtgcaa tggcatcttc aggagcccgg tgcacagggt   1200
ggtgacaaac gccgagaagg agaggatctc cctggccatg ttatacagcg tgaacgatga   1260
gaaagacatt gagccggcgg ctggtttgct ggatgagaat cggcctgcaa gatacaggaa   1320
agtgagcgtc gaagagttca gggccgggat ctttggaaaa ttctctcgag gagagaggta   1380
catcgactcc ctgaggatct gatctcgaag agagcatgat tgttgcaagc tcagcagctt   1440
tcagtagcaa gtatttcctt gggaaaacaa acattttttcc cccttaagg gaattgctga   1500
aaacatgtcg caagttctcg taaagaaaaa cttttaaatt taactatggt ataattgtaa   1560
tataattaca tatgtaataa cccctccgtt tcatattata agactttcta gcattgtcca   1620
catttatata gatgtgggca atgccataaa gtcttacaat atgaaaacgg aggaagtctt   1680
gtaactacgg tactgcattc ttttcaaatt acaaattact tgtcatccg              1729
```

<210> SEQ ID NO 2
<211> LENGTH: 351
<212> TYPE: PRT
<213> ORGANISM: Oryza sativa

<400> SEQUENCE: 2

```
Met Ala Asp Glu Ser Trp Arg Ala Pro Ala Ile Val Gln Glu Leu Ala
1               5                   10                  15

Ala Ala Gly Val Glu Glu Pro Pro Ser Arg Tyr Leu Leu Arg Glu Lys
            20                  25                  30

Asp Arg Ser Asp Val Lys Leu Val Ala Ala Glu Leu Pro Glu Pro Leu
        35                  40                  45

Pro Val Val Asp Leu Ser Arg Leu Asp Gly Ala Glu Glu Ala Thr Lys
    50                  55                  60

Leu Arg Val Ala Leu Gln Asn Trp Gly Phe Phe Leu Leu Thr Asn His
65                  70                  75                  80

Gly Val Glu Ala Ser Leu Met Asp Ser Val Met Asn Leu Ser Arg Glu
                85                  90                  95

Phe Phe Asn Gln Pro Ile Glu Arg Lys Gln Lys Phe Ser Asn Leu Ile
            100                 105                 110

Asp Gly Lys Asn Phe Gln Ile Gln Gly Tyr Gly Thr Asp Arg Val Val
        115                 120                 125

Thr Gln Asp Gln Ile Leu Asp Trp Ser Asp Arg Leu His Leu Arg Val
    130                 135                 140

Glu Pro Lys Glu Glu Gln Asp Leu Ala Phe Trp Pro Asp His Pro Glu
145                 150                 155                 160
```

Ser Phe Arg Asp Val Leu Asn Lys Tyr Ala Ser Gly Thr Lys Arg Ile
         165                 170                 175

Arg Asp Asp Ile Ile Gln Ala Met Ala Lys Leu Leu Glu Leu Asp Glu
         180                 185                 190

Asp Tyr Phe Leu Asp Arg Leu Asn Glu Ala Pro Ala Phe Ala Arg Phe
         195                 200                 205

Asn Tyr Tyr Pro Pro Cys Pro Arg Pro Asp Leu Val Phe Gly Ile Arg
210                 215                 220

Pro His Ser Asp Gly Thr Leu Leu Thr Ile Leu Leu Val Asp Lys Asp
225                 230                 235                 240

Val Ser Gly Leu Gln Val Gln Arg Asp Gly Lys Trp Ser Asn Val Glu
                 245                 250                 255

Ala Thr Pro His Thr Leu Leu Ile Asn Leu Gly Asp Thr Met Glu Val
                 260                 265                 270

Met Cys Asn Gly Ile Phe Arg Ser Pro Val His Arg Val Val Thr Asn
                 275                 280                 285

Ala Glu Lys Glu Arg Ile Ser Leu Ala Met Leu Tyr Ser Val Asn Asp
         290                 295                 300

Glu Lys Asp Ile Glu Pro Ala Ala Gly Leu Leu Asp Glu Asn Arg Pro
305                 310                 315                 320

Ala Arg Tyr Arg Lys Val Ser Val Glu Glu Phe Arg Ala Gly Ile Phe
                 325                 330                 335

Gly Lys Phe Ser Arg Gly Glu Arg Tyr Ile Asp Ser Leu Arg Ile
                 340                 345                 350

<210> SEQ ID NO 3
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 3
ctagctcccc aagtcgaaac                                                    20

<210> SEQ ID NO 4
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 4
atggggtgaa ctcacatgg                                                     19

<210> SEQ ID NO 5
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 5
gcaggctata gatgagctga aa                                                 22

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized primer sequence -continued

<400> SEQUENCE: 6
caggaagaag ccccaattct                                               20

<210> SEQ ID NO 7
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 7
cttaccaacc atggagtaga agc                                           23

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 8
tgaaagattc aggatggtca g                                             21

<210> SEQ ID NO 9
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 9
gttctgaaca agtatgcatc agga                                          24

<210> SEQ ID NO 10
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 10
ggtgtcacct aagttgatca gcaat                                         25

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 11
gggtttctga atgctgatgc                                               20

<210> SEQ ID NO 12
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 12
tgccttgaaa cgtgagaacg                                               20

<210> SEQ ID NO 13

```
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 13
tgttgtctga attcagaaag tac                                              23

<210> SEQ ID NO 14
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 14
tcctcatcaa gctcaagaag c                                                21

<210> SEQ ID NO 15
<211> LENGTH: 3932
<212> TYPE: DNA
<213> ORGANISM: Oryza sativa

<400> SEQUENCE: 15
gctagctccc caagtcgaaa cgtcgtcgcc cctcatcatc tcctcctcgt tgtcgcaccc        60
ccaaccgcac gctgccgccg ctcgcttcct cctctcctcg tctcactcca gaaagccaag       120
ctgcaaagca ctatggcaca tcccatagca atggcagcat ggacacacag ccatcggagc       180
cgaccgtggt aaaagctttc gtcgcggtgc ctgatatatc gacgccgaca tcgagcacgc       240
cccaactcca tgtgagttca ccccatcttt ccttctactt gctaatccag tgtttggtct       300
tggatgtcag tctgatagtt ctgctcctgc tatgagattg atgaatttgt ttgttgcttc       360
acctgtccgt tctcccaaaa catgttgaac tcggtgctgc tcgaataaaa cttgtagtgt       420
tgatttgatt cctagtttta gggatagcta taagggtcac caccattgac atggtaaatt       480
gtaggtccca aacgacatta cattttagtt gtgcagggag ttatataaac ttcgaaataa       540
ttcattctaa tattcagtga aaaggtttag ggtgagaaat actgcaagtt ttattttaga       600
ctaaaagagt ctaaaataac aatactctct gcatatctcc ttgaaaaggg ggctactgca       660
acgaagaagt attatggaac cataatggtt tgttttactc agttgtttga gtaattgagt       720
ttaatttcca taaacatcca ctattatgat gtaaaatatt tgaagaccgg ataggtgaag       780
atgatcttta ccagtagaag ccaatagaag acttattcag tttggccttg gtaaagtctg       840
aaacctgaaa acttaatgtt ctgttttcat atatgcagat ccaacaaatg cttagttatt       900
actccgtatg gtggaattcc atcgcttatc agcctggtaa agaatactgt tattaatttt       960
ctaaaactaa gagcaatgcc ataacttatt ctctatccac ttatgatagg aggtttcatt      1020
cttatgaaat tgtttatttc attattgatt cctcaatttt ctgtagtttt ttctatgcgt      1080
gctaactcag caagctcttt tatgggccta attgctcaaa acagattct tttttactct       1140 agattgaatt aaattatgta cataacaagt tgaaatcaga tgtgcatatt taatggctca      1200
gttctgccga ccaataataa cataatattt aaacatttag ttcggatcat aggttcgtct      1260
cgatatctaa ttctagttga ctgactatca atttatgtat ttttgaaaaa aaaaatcaaa      1320
tttaaagtat aatccaatta taatatatta tggcccatat atacacaagg ctcttatacg      1380
ggcatcacaa agtcgcgcaa cgcgcggcta ggtggctagt tatactagtt gaaatatcta      1440
ggagataaga gaaggcaagc aatggaattt gttttttccca ttcaggcatt cagccccgtt     1500
```

```
tggaactcaa ttccacaatg ttactagctc acttccacaa tgtcaaactg cttgaaatac    1560
cagtcccttt cttctgccca atgccacaat gttaaatagt ttgaatacct ttagtttaat    1620
ttcaaaaaag gaatttgaag attccctttc ttgtgctcaa ttccacgatg tcaaacagtt    1680
tgaataccta tcccttcctt cagctcaatc tgaatctttt tatcttatct ataacgagtc    1740
attttttttc accatgtata tcgtacatca tttcttctac tgttgaatag tagctgagaa    1800
gcagtgtcca ttctcattat gcctgaattt tcaatccatt ttcatccaag tatccaattc    1860
aagatgtatt tgcaggctat agatgagctg aaagatctcc tttcttttca agcaagaaca    1920
aagttaagca agggaagatc caagaacaag aacaccaatg gctgacgagt catggagggc    1980
gccggcgata gtgcaagagc tggcggcagc cggcgtcgag gagccgccga gccgatacct    2040
gctacgggag aaagaccgtt ctgacgtcaa gctggtcgcc gccgagctgc cggagcccct    2100
ccccgtcgtt gatctcagcc ggctagatgg tgccgaggag gccaccaagc tcagggtggc    2160
tctgcagaat tggggcttct tcctggtcag cttctaacaa gtgattctac tttgcttcat    2220
aaaaaagact tgctcatttg tattcatttc tccaatttgt gtggttgtgt gtgatccagc    2280
ttaccaacca tggagtagaa gcctctctga tggacagcgt gatgaacttg tcgagagagt    2340
ttttcaacca accaatcgaa cggaagcaaa aattcagcaa cttgatcgat ggcaagaact    2400
tccagattca agggtatgga actgaccggg tggttaccca agatcagatc ctggactggt    2460
ctgatcggtt gcatctcaga gttgaaccca aggaggagca agatcttgcc ttctggcctg    2520
accatcctga atctttcagg tcacctactc acctcacatt gatcgatgtt ttactttcca    2580
gtttccacac gtctgaattt gtttctcttt tgttttttcc ttttttgcaa aagatagtgt    2640
ttcttactgt tcatatatta cttacaaagt aacaaggatt gttgtctgaa ttcagaaagt    2700
acaacttgac gatgtatcaa gaaatggttt tgctgagcta tttgagagcc ttttcttctg    2760
cagggatgtt ctgaacaagt atgcatcatt caggctatgg ccaagcttct tgagcttgat    2820
gaggattact tcttggaccg actcaacgaa gctcctgcat ttgcaagatt caactactac    2880
cctccctgtc caaggcctga ccttgtgttc ggcatcaggc ctcactccga cggcaccctc    2940
ttgacgattc tttctcgtcga caaagatgtc agtggcctgc aagttcagag ggatggcaag    3000
tggtccaacg ttgaggcaac tcctcacaca ttgctgatca acttaggtga caccatggag    3060
gtaattgcct tattggcatc caacatccaa aatacttact ctctgaatct gcagacatcc    3120
agtacttcct ccgtttcata ttataagact ttctagcatt gcccacattc atatatatgt    3180
taatgaatct agacataata tatatataaa tgttgttaat gaatctagac acatatacat    3240
atatatgaat gtgggcaatg ctagaaagtc ttatgacctg aaacgaaggt agtatatctg    3300
atgataaatc caggggtttct gaatgctgat gcatatttgg atgcaacatt tctgtgcagg    3360
taatgtgcaa tggcatcttc aggagcccgg tgcacagggt ggtgacaaac gccgagaagg    3420
agaggatctc cctggccatg ttatacagcg tgaacgatga aaagacatt gagccggcgg    3480 ctggtttgct ggatgagaat cggcctgcaa gatacaggaa agtgagcgtc gaagagttca    3540
gggccgggat ctttggaaaa ttctctcgag gagagaggta catcgactcc ctgaggatct    3600
gatctcgaag agagcatgat tgttgcaagc tcagcagctt tcagtagcaa gtatttcctt    3660
gggaaaacaa acattttccc cccttaagg gaattgctga aaacatgtcg caagttctcg    3720
taaagaaaaa cttttaaatt taactatggt ataattgtaa tataattaca tatgtaataa    3780
cccctccgtt ttatattata agactttcta gcattgtcca catttatata gacgtgggta    3840
```

```
atgccataaa gtcttacaat atgaaacgga ggaagtccta tattgtaact acggtactgc    3900
attcttttca aattacaaat tacttgtcat cc                                  3932

<210> SEQ ID NO 16
<211> LENGTH: 1394
<212> TYPE: DNA
<213> ORGANISM: Oryza sativa
<220> FEATURE:
<221> NAME/KEY: CDS
<222> LOCATION: (52)..(1104)

<400> SEQUENCE: 16
ttgaggcaag aagaaaatta agcaaagaaa gatccaagaa caagaacact a atg gct      57
                                                         Met Ala
                                                           1 gac gag tca tgg agg acg ccg gcg ata gtg caa gag ctg gcg gcg gcc     105
Asp Glu Ser Trp Arg Thr Pro Ala Ile Val Gln Glu Leu Ala Ala Ala
          5                  10                  15 ggc gtc gag gag cca ccg agt cgg tac gtg ctt ggg gag aaa gac cgt     153
Gly Val Glu Glu Pro Pro Ser Arg Tyr Val Leu Gly Glu Lys Asp Arg
 20                  25                  30 tct gac gag ctg gtc gcc gcc gag ctg ccg gag ccc atc ccc gtc gtt     201
Ser Asp Glu Leu Val Ala Ala Glu Leu Pro Glu Pro Ile Pro Val Val
 35                  40                  45                  50 gat ctc agc cgg cta gcc ggc gcc gac gag gct gcc aag ctc agg gcg     249
Asp Leu Ser Arg Leu Ala Gly Ala Asp Glu Ala Ala Lys Leu Arg Ala
                 55                  60                  65 gct ctg cag aat tgg ggc ttc ttc ctg ctt acc aac cat gga gta gaa     297
Ala Leu Gln Asn Trp Gly Phe Phe Leu Leu Thr Asn His Gly Val Glu
             70                  75                  80 acc tct ctg atg gat gat gtg ttg aac ttg gca aga gag ttc ttc aac     345
Thr Ser Leu Met Asp Asp Val Leu Asn Leu Ala Arg Glu Phe Phe Asn
         85                  90                  95 caa ccg atc gaa cgg aag cga aaa ttc agc aac ttg atc gac ggc aag     393
Gln Pro Ile Glu Arg Lys Arg Lys Phe Ser Asn Leu Ile Asp Gly Lys
    100                 105                 110 aac ttc cag gtg gaa ggg tat gga act gac cgg gtg gta acc caa gat     441
Asn Phe Gln Val Glu Gly Tyr Gly Thr Asp Arg Val Val Thr Gln Asp
115                 120                 125                 130 cag atc ctg gac tgg tct gat cgg ctg ttt ctc aga gtt gaa ccc aag     489
Gln Ile Leu Asp Trp Ser Asp Arg Leu Phe Leu Arg Val Glu Pro Lys
                135                 140                 145 gag gag cga aat ctt gcc ttc tgg cct gac cat cct gaa tct ttc agg     537
Glu Glu Arg Asn Leu Ala Phe Trp Pro Asp His Pro Glu Ser Phe Arg
            150                 155                 160 gat gtt ctg aac gag tac gca tca aga acc aaa aga ata aga gac gat     585
Asp Val Leu Asn Glu Tyr Ala Ser Arg Thr Lys Arg Ile Arg Asp Asp
        165                 170                 175 atc gtt cag gct atg tcc aag ctt ctt ggg ctt gat gag gat tac ttc     633
Ile Val Gln Ala Met Ser Lys Leu Leu Gly Leu Asp Glu Asp Tyr Phe
    180                 185                 190 ttc gac cga ctc aac aaa gct cct gca ctt gca aga ttc aac tac tac     681
Phe Asp Arg Leu Asn Lys Ala Pro Ala Leu Ala Arg Phe Asn Tyr Tyr
195                 200                 205                 210 cct ccc tgt cca agg cct gac ctt gtg ttc ggc gtc agg cct cac tcc     729
Pro Pro Cys Pro Arg Pro Asp Leu Val Phe Gly Val Arg Pro His Ser
                215                 220                 225 gac ggc tcc ctc ttt acg att ctt ctc gtc gac gaa gat gtc ggt ggc     777
Asp Gly Ser Leu Phe Thr Ile Leu Leu Val Asp Glu Asp Val Gly Gly
            230                 235                 240
```

```
ctg caa att cag agg gat ggc aag tgg tac aat gtt cag gtc act ccc    825
Leu Gln Ile Gln Arg Asp Gly Lys Trp Tyr Asn Val Gln Val Thr Pro
        245                 250                 255 aac aca ttg ctg atc aac tta ggt gac acc atg gag gta ttg tgc aat    873
Asn Thr Leu Leu Ile Asn Leu Gly Asp Thr Met Glu Val Leu Cys Asn
260                 265                 270 ggc atc ttc agg agc cca gtg cac agg gtg gtg aca aac gcc gag agg    921
Gly Ile Phe Arg Ser Pro Val His Arg Val Val Thr Asn Ala Glu Arg
    275                 280                 285                 290 gag agg atc tca ctg gcc atg ttt tac agt gtg aat gat gag aaa gat    969
Glu Arg Ile Ser Leu Ala Met Phe Tyr Ser Val Asn Asp Glu Lys Asp
                295                 300                 305 att ggg ccg gcg gct ggt ttg ctg gat gag aat cgg cct gca aga tac    1017
Ile Gly Pro Ala Ala Gly Leu Leu Asp Glu Asn Arg Pro Ala Arg Tyr
310                 315                 320 agg aaa gtg agc gtc gga gag ttc agg gct ggg atc att gga aaa ttc    1065
Arg Lys Val Ser Val Gly Glu Phe Arg Ala Gly Ile Ile Gly Lys Phe
    325                 330                 335 tct cga cga gag aga tac atc gac tcc ctg aag atc tga tttgtactag    1114
Ser Arg Arg Glu Arg Tyr Ile Asp Ser Leu Lys Ile
                340                 345                 350 tagcatgatt gttgcaagct cagcagcttt cagtagcaag tattcctggg aaataaata   1174 tgttttttc cttgagggaa ttgctaaaag catgtcgcaa gttttttta acaaaaaact   1234 ttcaaatgta actataatat tattaatggt attgtaatta gacattatta atattatagt   1294
gttattatat tgtaattatt gtataattgt aatgtaatta cactattaac tacattggat   1354
atgttttttt tcctactttt atcgatatag ccatattagt                        1394

<210> SEQ ID NO 17
<211> LENGTH: 350
<212> TYPE: PRT
<213> ORGANISM: Oryza sativa

<400> SEQUENCE: 17

Met Ala Asp Glu Ser Trp Arg Thr Pro Ala Ile Val Gln Glu Leu Ala
1               5                   10                  15

Ala Ala Gly Val Glu Glu Pro Pro Ser Arg Tyr Val Leu Gly Glu Lys
            20                  25                  30

Asp Arg Ser Asp Glu Leu Val Ala Ala Glu Leu Pro Glu Pro Ile Pro
        35                  40                  45

Val Val Asp Leu Ser Arg Leu Ala Gly Ala Asp Glu Ala Ala Lys Leu
    50                  55                  60

Arg Ala Ala Leu Gln Asn Trp Gly Phe Phe Leu Leu Thr Asn His Gly
65                  70                  75                  80

Val Glu Thr Ser Leu Met Asp Asp Val Leu Asn Leu Ala Arg Glu Phe
                85                  90                  95

Phe Asn Gln Pro Ile Glu Arg Lys Arg Lys Phe Ser Asn Leu Ile Asp
            100                 105                 110

Gly Lys Asn Phe Gln Val Glu Gly Tyr Gly Thr Asp Arg Val Val Thr
        115                 120                 125

Gln Asp Gln Ile Leu Asp Trp Ser Asp Arg Leu Phe Leu Arg Val Glu
    130                 135                 140

Pro Lys Glu Glu Arg Asn Leu Ala Phe Trp Pro Asp His Pro Glu Ser
145                 150                 155                 160

Phe Arg Asp Val Leu Asn Glu Tyr Ala Ser Arg Thr Lys Arg Ile Arg
                165                 170                 175
```

```
Asp Asp Ile Val Gln Ala Met Ser Lys Leu Leu Gly Leu Asp Glu Asp
            180                 185                 190

Tyr Phe Phe Asp Arg Leu Asn Lys Ala Pro Ala Leu Ala Arg Phe Asn
        195                 200                 205

Tyr Tyr Pro Pro Cys Pro Arg Pro Asp Leu Val Phe Gly Val Arg Pro
    210                 215                 220

His Ser Asp Gly Ser Leu Phe Thr Ile Leu Leu Val Asp Glu Asp Val
225                 230                 235                 240

Gly Gly Leu Gln Ile Gln Arg Asp Gly Lys Trp Tyr Asn Val Gln Val
                245                 250                 255

Thr Pro Asn Thr Leu Leu Ile Asn Leu Gly Asp Thr Met Glu Val Leu
            260                 265                 270

Cys Asn Gly Ile Phe Arg Ser Pro Val His Arg Val Val Thr Asn Ala
        275                 280                 285

Glu Arg Glu Arg Ile Ser Leu Ala Met Phe Tyr Ser Val Asn Asp Glu
    290                 295                 300

Lys Asp Ile Gly Pro Ala Ala Gly Leu Leu Asp Glu Asn Arg Pro Ala
305                 310                 315                 320

Arg Tyr Arg Lys Val Ser Val Gly Glu Phe Arg Ala Gly Ile Ile Gly
                325                 330                 335

Lys Phe Ser Arg Arg Glu Arg Tyr Ile Asp Ser Leu Lys Ile
            340                 345                 350

<210> SEQ ID NO 18
<211> LENGTH: 65
<212> TYPE: DNA
<213> ORGANISM: Oryza sativa

<400> SEQUENCE: 18
ctgaacaagt atgcatcagg aaccaaaaga attagagacg atatcattca ggctatggcc    60
aagct                                                                65

<210> SEQ ID NO 19
<211> LENGTH: 37
<212> TYPE: DNA
<213> ORGANISM: Oryza sativa

<400> SEQUENCE: 19
ctgaacaagt atgcatcatt caggctatgg ccaagct                              37

<210> SEQ ID NO 20
<211> LENGTH: 40
<212> TYPE: DNA
<213> ORGANISM: Oryza sativa

<400> SEQUENCE: 20
agacacatat atgtctagat tcattaatat atatataaat                           40

<210> SEQ ID NO 21
<211> LENGTH: 21
<212> TYPE: DNA
<213> ORGANISM: Oryza sativa

<400> SEQUENCE: 21
agacataata tatatataaa t                                               21

<210> SEQ ID NO 22
<211> LENGTH: 30
<212> TYPE: DNA
```

```
<213> ORGANISM: Oryza sativa

<400> SEQUENCE: 22
catatatgtg tctagattca ttaacatata                                           30

<210> SEQ ID NO 23
<211> LENGTH: 14
<212> TYPE: DNA
<213> ORGANISM: Oryza sativa

<400> SEQUENCE: 23
cacatataca tata                                                            14

<210> SEQ ID NO 24
<211> LENGTH: 42
<212> TYPE: DNA
<213> ORGANISM: Oryza sativa

<400> SEQUENCE: 24
tatatataaa tgttgttaat gaatctagac atatatgtgt ct                             42

<210> SEQ ID NO 25
<211> LENGTH: 28
<212> TYPE: DNA
<213> ORGANISM: Oryza sativa

<400> SEQUENCE: 25
tatatatata aatgttgtta atgtgtct                                             28

<210> SEQ ID NO 26
<211> LENGTH: 351
<212> TYPE: PRT
<213> ORGANISM: Artificial Sequence
<220> FEATURE:
<223> OTHER INFORMATION: Amino acid sequence that is approximately 86%
      homologous to each of SEQ ID NOs:2 and 17
<220> FEATURE:
<221> NAME/KEY: MISC_FEATURE
<222> LOCATION: (8)..(8)
<223> OTHER INFORMATION: Xaa stands for any amino acid
<220> FEATURE:
<221> NAME/KEY: MISC_FEATURE
<222> LOCATION: (28)..(28)
<223> OTHER INFORMATION: Xaa stands for any amino acid
<220> FEATURE:
<221> NAME/KEY: MISC_FEATURE
<222> LOCATION: (30)..(30)
<223> OTHER INFORMATION: Xaa stands for any amino acid
<220> FEATURE:
<221> NAME/KEY: MISC_FEATURE
<222> LOCATION: (37)..(37)
<223> OTHER INFORMATION: Xaa stands for any amino acid
<220> FEATURE:
<221> NAME/KEY: MISC_FEATURE
<222> LOCATION: (38)..(38)
<223> OTHER INFORMATION: Xaa stands for any amino acid
<220> FEATURE:
<221> NAME/KEY: MISC_FEATURE
<222> LOCATION: (48)..(48)
<223> OTHER INFORMATION: Xaa stands for any amino acid
<220> FEATURE:
<221> NAME/KEY: MISC_FEATURE
<222> LOCATION: (57)..(57)
<223> OTHER INFORMATION: Xaa stands for any amino acid
<220> FEATURE:
<221> NAME/KEY: MISC_FEATURE
<222> LOCATION: (60)..(60)
<223> OTHER INFORMATION: Xaa stands for any amino acid
<220> FEATURE:
<221> NAME/KEY: MISC_FEATURE
<222> LOCATION: (63)..(63)
```

```
<223> OTHER INFORMATION: Xaa stands for any amino acid
<220> FEATURE:
<221> NAME/KEY: MISC_FEATURE
<222> LOCATION: (67)..(67)
<223> OTHER INFORMATION: Xaa stands for any amino acid
<220> FEATURE:
<221> NAME/KEY: MISC_FEATURE
<222> LOCATION: (84)..(84)
<223> OTHER INFORMATION: Xaa stands for any amino acid
<220> FEATURE:
<221> NAME/KEY: MISC_FEATURE
<222> LOCATION: (89)..(89)
<223> OTHER INFORMATION: Xaa stands for any amino acid
<220> FEATURE:
<221> NAME/KEY: MISC_FEATURE
<222> LOCATION: (91)..(91)
<223> OTHER INFORMATION: Xaa stands for any amino acid
<220> FEATURE:
<221> NAME/KEY: MISC_FEATURE
<222> LOCATION: (94)..(94)
<223> OTHER INFORMATION: Xaa stands for any amino acid
<220> FEATURE:
<221> NAME/KEY: MISC_FEATURE
<222> LOCATION: (106)..(106)
<223> OTHER INFORMATION: Xaa stands for any amino acid
<220> FEATURE:
<221> NAME/KEY: MISC_FEATURE
<222> LOCATION: (119)..(119)
<223> OTHER INFORMATION: Xaa stands for any amino acid
<220> FEATURE:
<221> NAME/KEY: MISC_FEATURE
<222> LOCATION: (120)..(120)
<223> OTHER INFORMATION: Xaa stands for any amino acid
<220> FEATURE:
<221> NAME/KEY: MISC_FEATURE
<222> LOCATION: (141)..(141)
<223> OTHER INFORMATION: Xaa stands for any amino acid
<220> FEATURE:
<221> NAME/KEY: MISC_FEATURE
<222> LOCATION: (150)..(150)
<223> OTHER INFORMATION: Xaa stands for any amino acid
<220> FEATURE:
<221> NAME/KEY: MISC_FEATURE
<222> LOCATION: (151)..(151)
<223> OTHER INFORMATION: Xaa stands for any amino acid
<220> FEATURE:
<221> NAME/KEY: MISC_FEATURE
<222> LOCATION: (168)..(168)
<223> OTHER INFORMATION: Xaa stands for any amino acid
<220> FEATURE:
<221> NAME/KEY: MISC_FEATURE
<222> LOCATION: (172)..(172)
<223> OTHER INFORMATION: Xaa stands for any amino acid
<220> FEATURE:
<221> NAME/KEY: MISC_FEATURE
<222> LOCATION: (181)..(181)
<223> OTHER INFORMATION: Xaa stands for any amino acid
<220> FEATURE:
<221> NAME/KEY: MISC_FEATURE
<222> LOCATION: (185)..(185)
<223> OTHER INFORMATION: Xaa stands for any amino acid
<220> FEATURE:
<221> NAME/KEY: MISC_FEATURE
<222> LOCATION: (189)..(189)
<223> OTHER INFORMATION: Xaa stands for any amino acid
<220> FEATURE:
<221> NAME/KEY: MISC_FEATURE
<222> LOCATION: (196)..(196)
<223> OTHER INFORMATION: Xaa stands for any amino acid
<220> FEATURE:
<221> NAME/KEY: MISC_FEATURE
<222> LOCATION: (201)..(201)
<223> OTHER INFORMATION: Xaa stands for any amino acid
<220> FEATURE:
<221> NAME/KEY: MISC_FEATURE
<222> LOCATION: (205)..(205)
<223> OTHER INFORMATION: Xaa stands for any amino acid
<220> FEATURE:
<221> NAME/KEY: MISC_FEATURE
```

```
<222> LOCATION: (223)..(223)
<223> OTHER INFORMATION: Xaa stands for any amino acid
<220> FEATURE:
<221> NAME/KEY: MISC_FEATURE
<222> LOCATION: (230)..(230)
<223> OTHER INFORMATION: Xaa stands for any amino acid
<220> FEATURE:
<221> NAME/KEY: MISC_FEATURE
<222> LOCATION: (232)..(232)
<223> OTHER INFORMATION: Xaa stands for any amino acid
<220> FEATURE:
<221> NAME/KEY: MISC_FEATURE
<222> LOCATION: (239)..(239)
<223> OTHER INFORMATION: Xaa stands for any amino acid
<220> FEATURE:
<221> NAME/KEY: MISC_FEATURE
<222> LOCATION: (242)..(242)
<223> OTHER INFORMATION: Xaa stands for any amino acid
<220> FEATURE:
<221> NAME/KEY: MISC_FEATURE
<222> LOCATION: (246)..(246)
<223> OTHER INFORMATION: Xaa stands for any amino acid
<220> FEATURE:
<221> NAME/KEY: MISC_FEATURE
<222> LOCATION: (253)..(253)
<223> OTHER INFORMATION: Xaa stands for any amino acid
<220> FEATURE:
<221> NAME/KEY: MISC_FEATURE
<222> LOCATION: (256)..(256)
<223> OTHER INFORMATION: Xaa stands for any amino acid
<220> FEATURE:
<221> NAME/KEY: MISC_FEATURE
<222> LOCATION: (257)..(257)
<223> OTHER INFORMATION: Xaa stands for any amino acid
<220> FEATURE:
<221> NAME/KEY: MISC_FEATURE
<222> LOCATION: (260)..(260)
<223> OTHER INFORMATION: Xaa stands for any amino acid
<220> FEATURE:
<221> NAME/KEY: MISC_FEATURE
<222> LOCATION: (273)..(273)
<223> OTHER INFORMATION: Xaa stands for any amino acid
<220> FEATURE:
<221> NAME/KEY: MISC_FEATURE
<222> LOCATION: (291)..(291)
<223> OTHER INFORMATION: Xaa stands for any amino acid
<220> FEATURE:
<221> NAME/KEY: MISC_FEATURE
<222> LOCATION: (299)..(299)
<223> OTHER INFORMATION: Xaa stands for any amino acid
<220> FEATURE:
<221> NAME/KEY: MISC_FEATURE
<222> LOCATION: (309)..(309)
<223> OTHER INFORMATION: Xaa stands for any amino acid
<220> FEATURE:
<221> NAME/KEY: MISC_FEATURE
<222> LOCATION: (329)..(329)
<223> OTHER INFORMATION: Xaa stands for any amino acid
<220> FEATURE:
<221> NAME/KEY: MISC_FEATURE
<222> LOCATION: (336)..(336)
<223> OTHER INFORMATION: Xaa stands for any amino acid
<220> FEATURE:
<221> NAME/KEY: MISC_FEATURE
<222> LOCATION: (342)..(342)
<223> OTHER INFORMATION: Xaa stands for any amino acid
<220> FEATURE:
<221> NAME/KEY: MISC_FEATURE
<222> LOCATION: (350)..(350)
<223> OTHER INFORMATION: Xaa stands for any amino acid

<400> SEQUENCE: 26

Met Ala Asp Glu Ser Trp Arg Xaa Pro Ala Ile Val Gln Glu Leu Ala
1               5                   10                  15

Ala Ala Gly Val Glu Glu Pro Pro Ser Arg Tyr Xaa Leu Xaa Glu Lys
            20                  25                  30
```

```
Asp Arg Ser Asp Xaa Xaa Leu Val Ala Ala Glu Leu Pro Glu Pro Xaa
            35                  40                  45

Pro Val Val Asp Leu Ser Arg Leu Xaa Gly Ala Xaa Glu Ala Xaa Lys
     50                  55                  60

Leu Arg Xaa Ala Leu Gln Asn Trp Gly Phe Phe Leu Leu Thr Asn His
 65                  70                  75                  80

Gly Val Glu Xaa Ser Leu Met Asp Xaa Val Xaa Asn Leu Xaa Arg Glu
                 85                  90                  95

Phe Phe Asn Gln Pro Ile Glu Arg Lys Xaa Lys Phe Ser Asn Leu Ile
            100                 105                 110

Asp Gly Lys Asn Phe Gln Xaa Xaa Gly Tyr Gly Thr Asp Arg Val Val
            115                 120                 125

Thr Gln Asp Gln Ile Leu Asp Trp Ser Asp Arg Leu Xaa Leu Arg Val
    130                 135                 140

Glu Pro Lys Glu Glu Xaa Xaa Leu Ala Phe Trp Pro Asp His Pro Glu
145                 150                 155                 160

Ser Phe Arg Asp Val Leu Asn Xaa Tyr Ala Ser Xaa Thr Lys Arg Ile
                165                 170                 175

Arg Asp Asp Ile Xaa Gln Ala Met Xaa Lys Leu Leu Xaa Leu Asp Glu
            180                 185                 190

Asp Tyr Phe Xaa Asp Arg Leu Asn Xaa Ala Pro Ala Xaa Ala Arg Phe
            195                 200                 205

Asn Tyr Tyr Pro Pro Cys Pro Arg Pro Asp Leu Val Phe Gly Xaa Arg
            210                 215                 220

Pro His Ser Asp Gly Xaa Leu Xaa Thr Ile Leu Leu Val Asp Xaa Asp
225                 230                 235                 240

Val Xaa Gly Leu Gln Xaa Gln Arg Asp Gly Lys Trp Xaa Asn Val Xaa
                245                 250                 255

Xaa Thr Pro Xaa Thr Leu Leu Ile Asn Leu Gly Asp Thr Met Glu Val
            260                 265                 270

Xaa Cys Asn Gly Ile Phe Arg Ser Pro Val His Arg Val Val Thr Asn
            275                 280                 285

Ala Glu Xaa Glu Arg Ile Ser Leu Ala Met Xaa Tyr Ser Val Asn Asp
    290                 295                 300

Glu Lys Asp Ile Xaa Pro Ala Ala Gly Leu Leu Asp Glu Asn Arg Pro
305                 310                 315                 320

Ala Arg Tyr Arg Lys Val Ser Val Xaa Glu Phe Arg Ala Gly Ile Xaa
                325                 330                 335

Gly Lys Phe Ser Arg Xaa Glu Arg Tyr Ile Asp Ser Leu Xaa Ile
            340                 345                 350
```

PLANT HAVING INCREASED RESISTANCE OR SUSCEPTIBILITY TO 4-HPPD INHIBITOR

TECHNICAL FIELD

The present invention relates to an agent for providing a plant with resistance or susceptibility to a 4-HPPD inhibitor, a transgenic plant cell capable of regenerating a plant having increased resistance or susceptibility to a 4-HPPD inhibitor, a plant regenerated from the cell, and methods for producing these. Further, the present invention relates to a method for determining whether a plant has resistance or susceptibility to a 4-HPPD inhibitor, and a method for breeding a plant having increased resistance or susceptibility to a 4-HPPD inhibitor by utilizing the determination.

BACKGROUND ART

Along with an increase in the demand for bioethanol fuels, the import price of feed grains from overseas has increased drastically, which has imposed heavy burden on livestock businesses in Japan. In this situation, in order to enhance domestic production and self-sufficiency rate of feeds, not paddy rice but alternate crops are cultivated by utilizing fallow fields and so forth. However, paddy fields suitable for cultivating these alternate crops are limited due to problems such as poor drainage. For this reason, use of rice as feeds and developments of exclusive feed-rice cultivars having a high productivity (high yielding cultivars) have been promoted. In order for such high yielding cultivars to demonstrate their characteristic high-yielding properties and stable growability, and also to improve the palatability and nutritional value of livestock, weed control in the cultivation paddy fields is an important cultivation management technique (NPL 1). Further, stable and economical productions of not only high yielding cultivars and rice but also crops require low-cost, energy-saving and easy weed control. Development and use of a highly selective herbicide are effective in such control (NPL 2). Hence, required are development and cultivation of crops resistant to the herbicide used.

Meanwhile, in the weed control in cultivation paddy fields, sulfonylurea (SU) herbicides are widely employed because the herbicides are effective against a wide range of weeds at a low dose and have little influence on human and also on the environment. Nevertheless, emergence of weeds such as *Scirpus juncoides* Roxb. having tolerance to SU herbicides has been recognized. This brings about a problem in the cultivation management for rice and so on.

Recently, as the measure against such a problem, herbicide components such as benzobicyclon (BBC), mesotrione, and tefuryltrione have been developed, which are also effective against plants tolerant to SU herbicides and have been put into practical use. All of BBC, mesotrione, and tefuryltrione are agents for inhibiting a function of 4-hydroxyphenylpyruvate dioxygenase (4-HPPD) (4-HPPD inhibitors). Inhibiting a function of this enzyme indirectly inhibits a carotenoid synthetic system and causes chlorophyll degradation to thereby whiten and wither the plant to death (see FIG. 1). The safety of these inhibitors against food rice cultivars has been sufficiently confirmed, so that the inhibitors are rapidly widespread in rice cultivation.

However, susceptibility of high yielding cultivars to the 4-HPPD inhibitors was not examined sufficiently at the developmental stage or other stages. By now, it has been reported that seven high-yielding feed rice cultivars are susceptible to 4-HPPD inhibitors and may be withered to death in some cases (NPLs 1 and 3).

Developments of a method capable of surely identifying the resistance or susceptibility to a 4-HPPD inhibitor and a method capable of increasing the resistance or susceptibility to a 4-HPPD inhibitor would make it possible to utilize a 4-HPPD inhibitor for control of a germination risk (problem from fallen seeds and seedlings) of "self-sown seeds" from the previous year in crop rotation cycles with food and feed rice cultivars as shown in FIG. 2, for example; consequently, production expansion of the feed rice cultivar and so forth can be expected. In addition, by utilizing these methods, a 4-HPPD inhibitor may be also used in an area management technique for cultivating crops such as rice, as necessary. Furthermore, if a gene serving as a marker for identifying resistance or susceptibility to a 4-HPPD inhibitor is found out, crops including rice can be bred efficiently.

Accordingly, it has been strongly desired to develop a technique for providing a plant with resistance or susceptibility to a 4-HPPD inhibitor and a technique for determining whether a plant has resistance or susceptibility to a 4-HPPD inhibitor. However, techniques which can efficiently achieve these purposes have not been developed yet.

CITATION LIST

Non Patent Literatures

[NPL 1] Keisuke Sekino et al., "Sensitivity of Nineteen Varieties and Line of Forage Rice to Paddy Herbicide, benzobicyclon," Japanese Journal of Crop Science, Mar. 25, 2009, vol. 227, extra issue, pp. 120 to 121

[NPL 2] Terry R. Wright et al., Proc Natl Acad Sci USA., Nov. 23, 2010, vol. 107, no. 47, pp. 20240 to 20 245

[NPL 3] Kiyoaki Maruyama et al., "Forage rice and so forth are revealed to be susceptible to some herbicide", [online], Mar. 26, 2010, National Agriculture and Food Research Organization Agricultural Research Center, Press Release, [retrieved on Sep. 29, 2010], the Internet <URL: http://narc.naro.affrc.go.jp/press/h22/0326/index.htm>

SUMMARY OF INVENTION

Technical Problem

The present invention has been made in view of the problems of the above-described conventional techniques. An object of the present invention is to provide a technology capable of efficiently providing a plant with resistance or susceptibility to a 4-HPPD inhibitor, and to provide a technology capable of efficiently determining whether a plant has resistance or susceptibility to a 4-HPPD inhibitor.

Solution to Problem

In order to achieve the above object, the present inventors, first, attempted to identify genes associated with resistance to a 4-HPPD inhibitor in a plant. Specifically, the present inventors, first, performed a quantitative trait locus (QTL) analysis using 4-HPPD inhibitor-susceptible rice and 4-HPPD inhibitor-resistant rice. This result revealed that a gene locus for determining resistance to a 4-HPPD inhibitor was located on a short arm of chromosome 2 of rice. Then, the present inventors examined a phenotype (4-HPPD inhibitor-susceptibility) using a Nipponbare line having a retrotransposon Tos17 inserted into a hypothetical gene of an iron/ascorbate-dependent oxidoreductase gene located at the gene locus specified by the QTL analysis. It was found out that Tos17-inserted homozygous individuals showed susceptibility to a 4-HPPD inhibitor. When the iron/ascorbate-dependent oxidoreductase gene thus found out was introduced into *Arabidopsis thaliana* (*A. thaliana*) and rice, these transgenic plants showed resistance to a 4-HPPD inhibitor. This supported that this gene is a responsible gene for providing a plant with resistance to a 4-HPPD inhibitor (hereinafter also referred to as 4-hydroxyphenylpyruvate dioxygenase inhibitor sensitive gene No. 1 (HIS1)). Additionally, genes having a high homology with the HIS1 gene of rice also exist in barley, sorghum, corn, and the like.

Further, the present inventors compared the structure of the HIS1 gene between the 4-HPPD inhibitor-susceptible rice and the 4-HPPD inhibitor-resistant rice by a PCR analysis. As a result, the rice cultivars showing susceptibility to a 4-HPPD inhibitor had insertion or deletion from the fourth exon to the fifth exon of the HIS1 gene. This may suggest that suppressing a function of the HIS1 gene provide a plant with susceptibility to a 4-HPPD inhibitor.

Moreover, it was revealed that a rice gene (HSL1 gene) having the highest homology with the HIS1 gene was located on chromosome 6 of rice. Furthermore, it was also revealed that when the HSL1 gene was introduced into rice, the transgenic rice also showed resistance to a 4-HPPD inhibitor.

Based on these findings, the present inventors found out that a utilization of the HIS1 gene or a homologous gene thereof makes it possible to produce a plant having increased resistance or susceptibility to a 4-HPPD inhibitor, and that targeting the genes makes it possible to determine whether a plant has resistance or susceptibility to a 4-HPPD inhibitor. These discoveries have led to the completion of the present invention.

More specifically, the present invention is as follows.

(1) An agent for providing a plant with resistance to a 4-HPPD inhibitor, the agent comprising at least one DNA or a vector having the DNA inserted therein, the DNA encoding a protein having an activity of providing a plant with resistance to a 4-HPPD inhibitor, the DNA selected from the group consisting of the following (a) to (d):

(a) a DNA encoding a protein having an amino acid sequence of any one of SEQ ID NOs: 2 and 17;

(b) a DNA encoding a protein having an amino acid sequence of any one of SEQ ID NOs: 2 and 17, in which one or more amino acids are substituted, deleted, added, and/or inserted;

(c) a DNA hybridizing under stringent conditions to a DNA having a base sequence of any one of SEQ ID NOs: 1 and 16; and (d) a DNA encoding an amino acid sequence having a homology of 60% or more with an amino acid sequence of any one of SEQ ID NOs: 2 and 17.

(2) A transgenic plant cell capable of regenerating a plant having increased resistance to a 4-HPPD inhibitor, the transgenic plant cell comprising at least one DNA or a vector having the DNA inserted therein, the DNA encoding a protein having an activity of providing a plant with resistance to a 4-HPPD inhibitor, the DNA selected from the group consisting of the following (a) to (d):

(a) a DNA encoding a protein having an amino acid sequence of any one of SEQ ID NOs: 2 and 17;

(b) a DNA encoding a protein having an amino acid sequence of any one of SEQ ID NOs: 2 and 17, in which one or more amino acids are substituted, deleted, added, and/or inserted;

(c) a DNA hybridizing under stringent conditions to a DNA having a base sequence of any one of SEQ ID NOs: 1 and 16; and (d) a DNA encoding an amino acid sequence having a homology of 60% or more with an amino acid sequence of any one of SEQ ID NOs: 2 and 17.

(3) A plant having increased resistance to a 4-HPPD inhibitor, which is regenerated from the transgenic plant cell according to (2).

(4) A plant having increased resistance to a 4-HPPD inhibitor, which is any one of a progeny and a clone of the plant according to (3).

(5) A propagation material of the plant having increased resistance to a 4-HPPD inhibitor according to any one of (3) and (4).

(6) A method for producing a plant having increased resistance to a 4-HPPD inhibitor, the method comprising:

(I) a step of introducing into a plant cell at least one DNA or a vector having the DNA inserted therein, the DNA encoding a protein having an activity of providing a plant with resistance to a 4-HPPD inhibitor, the DNA selected from the group consisting of the following (a) to (d), (a) a DNA encoding a protein having an amino acid sequence of any one of SEQ ID NOs: 2 and 17, (b) a DNA encoding a protein having an amino acid sequence of any one of SEQ ID NOs: 2 and 17, in which one or more amino acids are substituted, deleted, added, and/or inserted, (c) a DNA hybridizing under stringent conditions to a DNA having a base sequence of any one of SEQ ID NOs: 1 and 16, and (d) a DNA encoding an amino acid sequence having a homology of 60% or more with an amino acid sequence of any one of SEQ ID NOs: 2 and 17; and (II) a step of regenerating a plant from the transgenic plant cell in which the DNA or the vector having the DNA inserted therein has been introduced in step (I).

(7) An agent for providing a plant with susceptibility to a 4-HPPD inhibitor, the agent comprising at least one DNA or a vector having the DNA inserted therein, the DNA encoding an RNA having an activity of providing a plant with susceptibility to a 4-HPPD inhibitor, the DNA selected from the group consisting of the following (a) to (c):

(a) a DNA encoding a double-stranded RNA complementary to a transcript of the DNA according to (1);

(b) a DNA encoding an antisense RNA complementary to a transcript of the DNA according to (1); and (c) a DNA encoding an RNA having a ribozyme activity of specifically cleaving a transcript of the DNA according to (1).

(8) A transgenic plant cell capable of regenerating a plant having increased susceptibility to a 4-HPPD inhibitor, the transgenic plant cell comprising at least one DNA or a vector having the DNA inserted therein, the DNA encoding an RNA having an activity of providing a plant with susceptibility to a 4-HPPD inhibitor, the DNA selected from the group consisting of the following (a) to (c):

(a) a DNA encoding a double-stranded RNA complementary to a transcript of the DNA according to (1);

(b) a DNA encoding an antisense RNA complementary to a transcript of the DNA according to (1); and (c) a DNA encoding an RNA having a ribozyme activity of specifically cleaving a transcript of the DNA according to (1).

(9) A plant having increased susceptibility to a 4-HPPD inhibitor, which is regenerated from the transgenic plant cell according to (8).

(10) A plant having increased susceptibility to a 4-HPPD inhibitor, which is any one of a progeny and a clone of the plant according to (9).

(11) A propagation material of the plant having increased susceptibility to a 4-HPPD inhibitor according to any one of (9) and (10).

(12) A method for producing a plant having increased susceptibility to a 4-HPPD inhibitor, the method comprising:

(I) a step of introducing into a plant cell at least one DNA or a vector having the DNA inserted therein, the DNA encoding an RNA having an activity of providing a plant with susceptibility to a 4-HPPD inhibitor, the DNA selected from the group consisting of the following (a) to (c), (a) a DNA encoding a double-stranded RNA complementary to a transcript of the DNA according to (1), (b) a DNA encoding an antisense RNA complementary to a transcript of the DNA according to (1), and (c) a DNA encoding an RNA having a ribozyme activity of specifically cleaving a transcript of the DNA according to (1); and (II) a step of regenerating a plant from the transgenic plant cell in which the DNA or the vector having the DNA inserted therein has been introduced in step (I).

(13) A method for determining whether a plant has resistance or susceptibility to a 4-HPPD inhibitor, wherein the method comprises analyzing a base sequence of at least one DNA, in a test plant, selected from the group consisting of the following (a) to (d) or a base sequence of an expression control region of the DNA:

(a) a DNA encoding a protein having an amino acid sequence of any one of SEQ ID NOs: 2 and 17;

(b) a DNA encoding a protein having an amino acid sequence of any one of SEQ ID NOs: 2 and 17, in which one or more amino acids are substituted, deleted, added, and/or inserted;

(c) a DNA hybridizing under stringent conditions to a DNA having a base sequence of any one of SEQ ID NOs: 1 and 16; and (d) a DNA encoding an amino acid sequence having a homology of 60% or more with an amino acid sequence of any one of SEQ ID NOs: 2 and 17.

(14) A method for determining whether a plant has resistance or susceptibility to a 4-HPPD inhibitor, wherein the method comprises detecting an expression of at least one DNA, in a test plant, selected from the group consisting of the following (a) to (d), or a molecular weight of any one of an amplification product and an expression product of the DNA:

(a) a DNA encoding a protein having an amino acid sequence of any one of SEQ ID NOs: 2 and 17;

(b) a DNA encoding a protein having an amino acid sequence of any one of SEQ ID NOs: 2 and 17, in which one or more amino acids are substituted, deleted, added, and/or inserted;

(c) a DNA hybridizing under stringent conditions to a DNA having a base sequence of any one of SEQ ID NOs: 1 and 16; and (d) a DNA encoding an amino acid sequence having a homology of 60% or more with an amino acid sequence of any one of SEQ ID NOs: 2 and 17.

(15) A method for breeding a plant having increased resistance to a 4-HPPD inhibitor, the method comprising:

(a) a step of crossing a plant cultivar resistant to a 4-HPPD inhibitor with any cultivar;

(b) a step of determining whether individuals obtained by the crossing in step (a) have resistance or susceptibility to a 4-HPPD inhibitor by the method according to any one of (13) and (14); and (c) a step of selecting an individual determined to have resistant to the 4-HPPD inhibitor.

(16) A method for breeding a plant having increased susceptibility to a 4-HPPD inhibitor, the method comprising:

(a) a step of crossing a plant cultivar susceptible to a 4-HPPD inhibitor with any cultivar;

(b) a step of determining whether individuals obtained by the crossing in step (a) have resistance or susceptibility to a 4-HPPD inhibitor by the method according to any one of (13) and (14); and (c) a step of selecting an individual determined to have susceptibility to the 4-HPPD inhibitor.

Advantageous Effects of Invention

A utilization of genes identified in the present invention makes it possible to efficiently produce a plant having increased resistance or susceptibility to a 4-HPPD inhibitor. Moreover, targeting the genes identified in the present invention makes it possible to efficiently determine whether a plant has resistance or susceptibility to a 4-HPPD inhibitor.

BRIEF DESCRIPTION OF DRAWINGS

FIG. 19 is a representation for comparing the amino acid sequences of proteins encoded by the HIS1 gene and a homologous gene thereof (HSL1 gene), and illustrating the homology.

DESCRIPTION OF EMBODIMENTS

<Agent for Providing Plant with Resistance to 4-HPPD Inhibitor>

An agent for providing a plant with resistance to a 4-HPPD inhibitor of the present invention is characterized in that the agent comprises a DNA or a vector having the DNA inserted therein, the DNA encoding a protein having an activity of providing a plant with resistance to a 4-HPPD inhibitor (hereinafter may be referred to as resistance DNA of the present invention).

Figure 1:
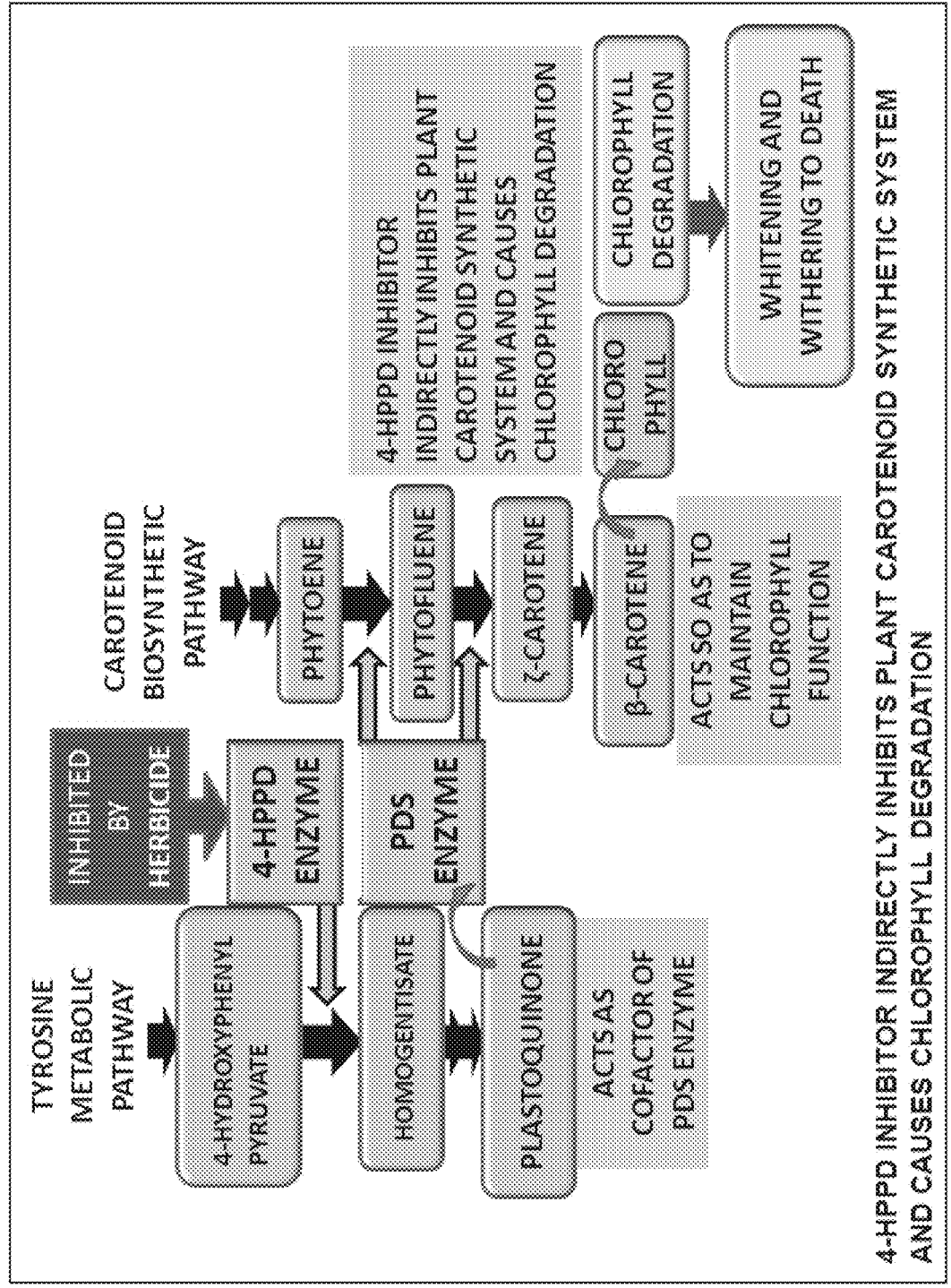
FIG. 1 is a diagram for illustrating a schematic and a relation of a 4-HPPD inhibitor to a tyrosine metabolic pathway and a carotenoid biosynthetic pathway.
Figure 2:
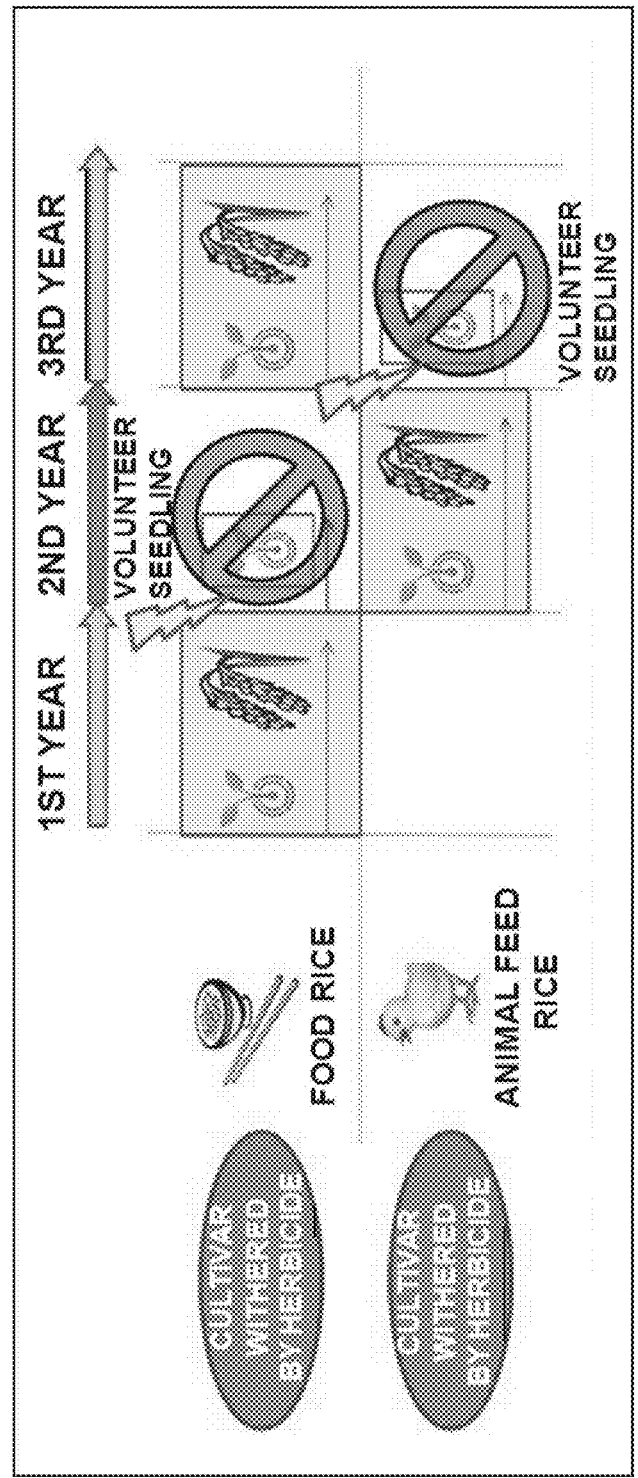
FIG. 2 is a diagram for illustrating a schematic of controlling a germination risk of "self-sown seeds" from the previous years in crop rotation cycles with food and feed rice cultivars.
Figure 3:
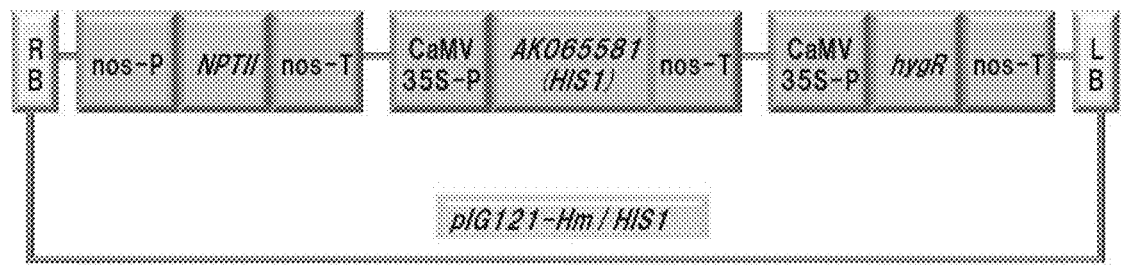
FIG. 3 is a representation for illustrating a schematic of a binary vector (pIG121-Hm/HIS1) used for transformation of *Arabidopsis thaliana* by an *Agrobacterium* method, the binary vector obtained by linking boundary sequences (RB: right boundary sequence, LB: left boundary sequence) to expression cassettes of a kanamycin resistance gene (NPTII) driven by a nos promoter (nos-P), a hygromycin resistance gene (hygR) driven by a CaMV35S promoter (CaMV35S-P), and AK065581 (HIS1) driven by a CaMV35S promoter.
Figure 4:
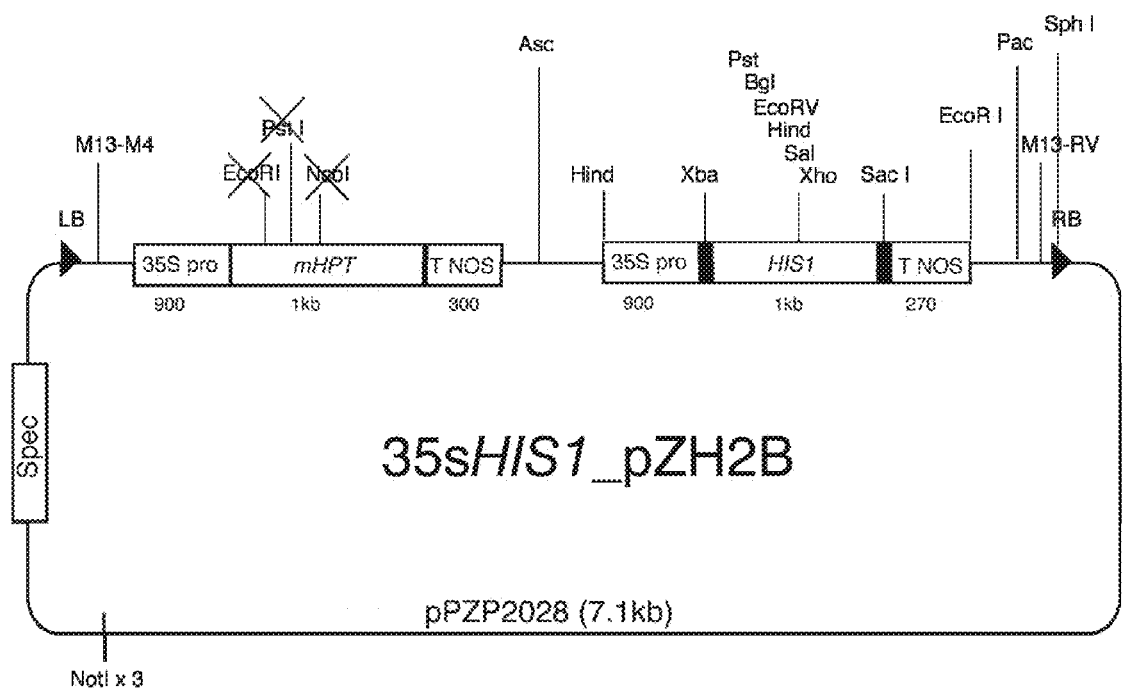
FIG. 4 is a representation for illustrating a schematic of a binary vector (35sHIS1 pZH2B) used for transformation of *Arabidopsis thaliana* and rice by the *Agrobacterium* method, the binary vector obtained by linking boundary sequences (RB: right boundary sequence, LB: left boundary sequence) to expression cassettes of a hygromycin resistance gene (mHPT) driven by a CaMV35S promoter (35S Pro) and AK065581 (HIS1) driven by a CaMV35S promoter (35S Pro).

In the present invention, a "4-HPPD inhibitor" means an agent for inhibiting a function of 4-HPPD (4-hydroxyphenylpyruvate dioxygenase) (4-HPPD inhibitor). As shown in FIG. 1, a 4-HPPD inhibitor inhibits a function of 4-HPPD, and thereby indirectly inhibits a carotenoid synthetic system and causes chlorophyll degradation to whiten and wither the plant to death. In the present invention, examples of the "4-HPPD inhibitor" include triketone type 4-HPPD inhibitors such as benzobicyclon (BBC), mesotrione, tefuryltrione, tembotrione, and 2-(2-nitro-4-trifluoromethylbenzoyl)cyclohexane-1,3-dione (NTBC), and pyrazole type 4-HPPD inhibitors such as pyrazolate, benzofenap, and pyrazoxyfen. The 4-HPPD inhibitor, resistance to which is provided to a plant using the resistance DNA of the present invention, is preferably triketone type 4-HPPD inhibitors such as BBC, mesotrione, tefuryltrione, tembotrione, and NTBC; particularly preferable is BBC.

Note that although components of herbicides such as 4-HPPD inhibitors as described above are quite diverse compounds, it is possible to classify the herbicides into several groups based on mode of action as follows (see "From Pesticides to Agrobioregulators-disease, pest, and weed controls at present and in the future," Japan, CMC Publishing Co., Ltd., January 2010).

(I) Acetyl-Coa Carboxylase (ACCase) Inhibiting Herbicides

This herbicide group inhibits ACCase involved at the first stage of lipid synthesis, and inhibits cell membrane synthesis, impeding the plant growth. The herbicides belonging to this group are further classified into (1) 4-aryloxyphenoxypropionate type, (2) cyclohexanedione oxime type, and (3) dione type.

(II) Acetolactate Synthase (ALS) Inhibiting Herbicides

This herbicide group, which targets ALS, inhibits ALS activity, and inhibits branched-amino acid synthesis, thereby impeding plant growth. The herbicides belonging to this group are further classified into (1) sulfonylurea type, (2) triazolinone type, (3) triazolopyrimidine type, (4) pyrimidinylsalicylate type, and (5) imidazolinone type.

(III) 4-HPPD Metabolism Inhibiting Herbicides

This herbicide group inhibits 4-HPPD metabolism in a tyrosine metabolic pathway, and indirectly inhibits a carotenoid synthetic system of a plant to whiten and wither the plant to death. The herbicides belonging to this group are further classified into (1) cyclohexanedione type, (2) pyrazole type, (3) bicyclo type, (4) isoxazole type, and (5) triketone type. Moreover, examples of (1) cyclohexanedione type include benzoylcyclohexane-1,3-dione derivatives. Examples of (2) pyrazole type include pyrazolate, benzofenap, and pyrazoxyfen. Examples of (3) bicyclo type include 3-substituted benzoyl-bicyclo[4,1,0]heptane-2,4-dione derivatives. An example of (4) isoxazole type is isoxaflutole. Examples of (5) triketone type include BBC, mesotrione, tefuryltrione, and tembotrione.

(IV) Protoporphyrinogen IX Oxidase (PPO) Inhibitor Herbicides

Herbicides of this group inhibit chlorophyll synthesis, degrade the cell membrane, and cause death by withering. The herbicides belonging to this group are further classified into (1) diphenyl ether type, (2) diallyl type, and (3) pyrazole type.

(V) Very-Long-Chain Fatty Acid Elongase (VLCFAE) Inhibiting Herbicides

Herbicides of this group inhibit biosynthetic system enzymes of very-long-chain fatty acids having C20 or longer in the plant lipid biosynthetic system, and wither the plant to death.

(VI) Phytoene Desaturase (PDS) Inhibiting Herbicides

This herbicide group inhibits a PDS enzyme in the carotenoid biosynthetic pathway, and causes plant chlorophyll degradation to whiten and wither the plant to death.

(VII) PS II Inhibiting Herbicides

Inhibitors of this group bind to plastoquinone (PQ), and as a result inhibit PQ-involving electron transfer from photosystem II (PS II) to photosystem I (PS I), so that the carbon fixation function in the plant cannot work, and the plant is withered to death.

(VIII) Synthetic Auxin Herbicides

Inhibitors of this group act like natural auxin, which is present at a low concentration in plants and regulates the plant growth, so that the plant differentiates and grows abnormally and is consequently withered to death.

(IX) EPSP Synthase (EPSPS) Inhibiting Herbicides

Inhibitors of this group bind to EPSPS in the shikimic acid pathway, and inhibit EPSP synthesis. As a result, tryptophan, phenylalanine, and tyrosine are not biosynthesized, and the plant is withered to death.

As examples of the resistance DNA of the present invention, the base sequence of a hypothetical gene (HIS1 gene; Os02g0280700) of an iron/ascorbate-dependent oxidoreductase gene derived from Nipponbare is shown in SEQ ID NO: 1, and the amino acid sequence of a protein encoded by the DNA is shown in SEQ ID NO: 2.

Moreover, as another example of the resistance DNA of the present invention, the base sequence of a gene (HIS1-LIKE (HSL) 1 gene; Os06g0176700/Os06g0178500 (AK241948) derived from Nipponbare is shown in SEQ ID NO: 16), and the amino acid sequence of a protein encoded by the DNA is shown in SEQ ID NO: 17.

One form of the resistance DNA of the present invention is a DNA encoding a protein having an amino acid sequence of SEQ ID NO: 2 (typically, a DNA comprising a coding region for the base sequence of SEQ ID NO: 1).

Moreover, another form of the resistance DNA of the present invention is a DNA encoding a protein having an amino acid sequence of SEQ ID NO: 17 (typically, a DNA comprising a coding region for the base sequence of SEQ ID NO: 16).

Once obtaining information on such DNA base sequences in the current state of the art, those skilled in the art could modify the base sequences in various ways to produce a mutation gene encoding a protein having an activity of providing a plant with resistance to a 4-HPPD inhibitor. Moreover, in nature also, a base sequence may be mutated. Thus, the resistance DNA of the present invention includes a DNA encoding a protein having an amino acid sequence of any one of SEQ ID NOs: 2 and 17, in which one or more amino acids are substituted, deleted, added, and/or inserted, as long as a protein having the above-described activity is encoded. Herein, the term "more" refers to generally 50 amino acids or less, preferably 30 amino acids or less, more preferably 10 amino acids or less, and particularly preferably several amino acids or less (for example, 5 amino acids or less, 3 amino acids or less, 2 amino acids or less, or 1 amino acid) in the entire amino acid sequence of the HIS1 protein or the HSL1 protein.

Further, once obtaining a particular resistance DNA in the current state of the art, those skilled in the art could utilize information on the DNA base sequence to isolate a homologous gene, which encodes a protein having an activity of providing a plant with resistance to a 4-HPPD inhibitor, from a plant of the same or different species. As the plant from which such a homologous gene is obtained, monocots are preferable, and Poaceae plants are particularly preferable. Examples of the Poaceae plants include rice (for example, 4-HPPD inhibitor-resistant cultivars Nipponbare, Koshihikari, Kitaaoba, Akihikari, Akitakomachi, Fukuhibiki, Bekoaoba, Bekogonomi, Yumeaoba, Hokuriku 193, Leaf Star, Tachisugata, Kusanohoshi, Hoshiaoba, Nishiaoba, Tachiaoba, Makimizuho, Mogumoguaoba, Hamasari, Minamiyutaka), barley, sorghum, corn, and the like.

Examples of a method for obtaining the homologous gene include hybridization techniques (Southern, E. M., J. Mol. Biol., 98: 503, 1975) and polymerase chain reaction (PCR) techniques (Saiki, R. K., et al. Science, 230: 1350-1354, 1985, Saiki, R. K. et al. Science, 239: 487-491, 1988). To isolate the homologous gene, generally, a hybridization reaction is carried out under stringent conditions. Examples of the stringent hybridization conditions include conditions of 6 M urea, 0.4% SDS, and 0.5×SSC; and hybridization conditions of equivalent stringency thereto. It can be expected that when higher stringency conditions are used, for example, conditions of 6 M urea, 0.4% SDS, and 0.1×SSC, a gene having a higher homology is isolated. The resistance DNA of the present invention includes a DNA hybridizing under stringent conditions to a DNA having a base sequence of any one of SEQ ID NOs: 1 and 16, as long as a protein having an activity of providing a plant with resistance to a 4-HPPD inhibitor is encoded.

The protein encoded by the homologous gene thus obtained generally has a high homology with the amino acid sequence of any one of SEQ ID NOs: 2 and 17. The high homology refers to a sequence homology of at least 60% or more, preferably 80% or more (for example, 85%, 90%, 95%, 97%, 99% or more). The homology of sequences can be determined utilizing a BLASTX (amino acid level) program (Altschul et al. J. Mol. Biol., 215: 403-410, 1990). This program is based on algorithm BLAST by Karlin and Altschul (Proc. Natl. Acad. Sci. USA, 87: 2264-2268, 1990, Proc. Natl. Acad. Sci. USA, 90:5873-5877, 1993). When an amino acid sequence is analyzed with BLASTX, the parameters are set at, for example, score=50 and word length=3. Alternatively, when an amino acid sequence is analyzed using a Gapped BLAST program, the analysis can be performed as described in Altschul et al (Nucleic Acids Res. 25: 3389-3402, 1997). When BLAST and Gapped BLAST programs are used, the default parameters of each program are used. The specific procedures of these analysis methods are known. The resistance DNA of the present invention includes a DNA encoding an amino acid sequence having a homology of 60% or more with an amino acid sequence of any one of SEQ ID NOs: 2 and 17, as long as a protein having an activity of providing a plant with resistance to a 4-HPPD inhibitor is encoded. Examples of such a DNA include a barley-derived gene (HvHCP1 (AF527606)), a corn-derived gene (ZmHSL1 (BT062842), ZmHSL2 (NM_001153464)), and a sorghum-derived gene (SbHSL1 (XM_002436546)) (see FIG. 21).

Whether or not a protein encoded by a particular gene has an activity of providing a plant with resistance to a 4-HPPD inhibitor can be determined, for example, by introducing the gene into a plant, and assaying whether or not the plant thus produced is provided with the resistance as described in Examples later (see Example 2). Specifically, in a case of using *A. thaliana* (ecotype Columbia) that would be whitened by an agar medium containing 0.03 μM BBC, if a transformant produced by introducing the gene into *A. thaliana* can grow without being whitened in the presence of BBC at the above concentration, the protein encoded by the gene can be determined to have an activity of providing a plant with resistance to a 4-HPPD inhibitor. Moreover, in a case of using a BBC susceptible rice cultivar "Kanto 239" that would be whitened by an agar medium containing 0.1 μM BBC, if a transformant produced by introducing the gene into Kanto 239 can grow without being whitened in the presence of BBC at the above concentration, the protein encoded by the gene can be determined to have an activity of providing a plant with resistance to a 4-HPPD inhibitor. Further, in a case of using a triketone type 4-HPPD inhibitor other than BBC (mesotrione, tefuryltrione, tembotrione, NTBC, or the like), if a transformant produced by introducing the gene into Kanto 239 can grow without being whitened in the presence of 1 μM mesotrione, 2.5 μM tefuryltrione, 0.5 μM tembotrione, or 1 μM NTBC, the protein encoded by the gene can be determined to have an activity of providing a plant with resistance to a 4-HPPD inhibitor.

The form of the resistance DNA of the present invention is not particularly limited, and includes, besides a cDNA, a genomic DNA and a chemically synthesized DNA. These DNAs can be prepared by utilizing conventional means for those skilled in the art. A genomic DNA can be prepared, for example, by extracting a genomic DNA from a plant, constructing a genomic library (the vector that can be utilized is a plasmid, phage, cosmid, BAC, PAC, or the like), deploying the library, followed by colony hybridization or plaque hybridization using a probe prepared based on the base sequence of the HIS1 gene (for example, DNA having SEQ ID NO: 1) or the HSL1 gene (for example, DNA having SEQ ID NO: 16). Alternatively, the genomic DNA can also be prepared by producing a primer specific to the HIS1 gene or the HSL1 gene, followed by PCR utilizing the primer. Meanwhile, the cDNA can be prepared, for example, by synthesizing a cDNA based on an mRNA extracted from a plant, inserting the cDNA into a vector such as AZAP to construct a cDNA library, deploying the library, followed by PCR or followed by colony hybridization or plaque hybridization in the same manner as above. Alternatively, using a commercially-available DNA synthesizer, a target DNA can also be prepared by synthesis.

<Agent for Providing Plant with Susceptibility to 4-HPPD Inhibitor>

Additionally, the present invention provides an agent for providing a plant with susceptibility to a 4-HPPD inhibitor. As illustrated in Examples later, suppressing a function of a protein encoded by the HIS1 gene suppresses resistance to a 4-HPPD inhibitor. Thus, the agent for providing a plant with resistance to a 4-HPPD inhibitor of the present invention is characterized in that the agent comprises a DNA or a vector having the DNA inserted therein, the DNA encoding an RNA having an activity of providing a plant with susceptibility to a 4-HPPD inhibitor.

One form of the DNA encoding an RNA having an activity of providing a plant with susceptibility to a 4-HPPD inhibitor, is a DNA encoding a dsRNA (double-stranded RNA) complementary to a transcript of the endogenous resistance DNA of the present invention described above. Introducing a dsRNA having a sequence the same as or similar to the target gene sequence into a cell can induce a phenomenon called RNAi (RNA interference), by which expressions of both the introduced exogenous gene and the target endogenous gene are suppressed. When approximately 40 to several hundred base pairs of dsRNA are introduced into a cell, an RNaseIII-like nuclease called Dicer, which has a helicase domain, excises approximately 21 to 23 base pairs of the dsRNA from the 3' end at a time in the presence of ATP, forming siRNA (short interference RNA). A specific protein binds to the siRNA to form a nuclease complex (RISC: RNA-induced silencing complex).

This complex recognizes and binds to a sequence identical to that of the siRNA, and cleaves a transcript (mRNA) of the target gene at a location corresponding to a central portion of the siRNA by an RNaseIII-like enzyme activity. Meanwhile, independently of this pathway, an antisense strand of the siRNA binds to mRNA and acts as a primer for an RNA-dependent RNA polymerase (RsRP), and a dsRNA is synthesized. This dsRNA again serves as a substrate of Dicer to form other siRNA, and is considered as a pathway for amplifying the action.

The DNA encoding the dsRNA of the present invention comprises: an antisense DNA encoding an antisense RNA for any region of a transcript (mRNA) of a target gene, that is, the endogenous resistance DNA of the present invention; and a sense DNA encoding a sense RNA for any region of the mRNA. The antisense RNA and the sense RNA can be expressed by the antisense DNA and the sense DNA, respectively. Moreover, the dsRNA can be prepared by these antisense RNA and sense RNA.

As the configuration to incorporate the dsRNA expression system of the present invention into a vector or the like, the antisense RNA and the sense RNA may by expressed from the same vector, or the antisense RNA and the sense RNA may be expressed from different vectors, respectively. As the configuration in which the antisense RNA and the sense RNA are expressed from the same vector, for example, an antisense RNA expression cassette and a sense RNA expression cassette are constructed, in each of which a promoter capable of expressing a short RNA, such as a pol III system, is linked upstream of the antisense DNA and the sense DNA, and these cassettes are inserted into the vector in the same direction or opposite directions.

Moreover, it is also possible to construct an expression system in which the antisense DNA and the sense DNA are arranged in opposite directions in such a manner as to face each other on the different strands. This construct includes: a single double-stranded DNA (siRNA-encoding DNA) in which an antisense RNA-encoding strand is paired with a sense RNA-encoding strand; and promoters facing each other on both sides of the DNA so that the antisense RNA and the sense RNA can be expressed from the respective strands. In this case, in order to avoid addition of extra sequences downstream of the sense RNA and the antisense RNA, it is preferable to provide a terminator at the 3' end of each of the strands (the antisense RNA-encoding strand, the sense RNA-encoding strand). As the terminator, a sequence of four or more consecutive A (adenine) bases, or the like can be used. In addition, in this palindromic expression system, the type of the two promoters is preferably different.

Meanwhile, as the configuration in which the antisense RNA and the sense RNA are expressed from different vectors, for example, an antisense RNA expression cassette and a sense RNA expression cassette are constructed, in each of which a promoter capable of expressing a short RNA, such as a pol III system, is linked upstream of the antisense DNA and the sense DNA, and these cassettes are incorporated into different vectors.

The dsRNA used in the present invention is preferably a siRNA. A "siRNA" means a double-stranded RNA made of short strands in such a range that no toxicity is demonstrated within a cell. The length is not particularly limited, as long as the expression of the target gene can be suppressed and no toxicity is demonstrated. The length of the dsRNA is for example 15 to 49 base pairs, preferably 15 to 35 base pairs, and further preferably 21 to 30 base pairs.

As the DNA encoding the dsRNA of the present invention, it is also possible to use such a construct including an appropriate sequence (desirably, intron sequence) inserted between inverted repeats of the target sequence as to encode a double-stranded RNA having a hairpin structure (self-complementary 'hairpin' RNA (hpRNA)) (Smith, N. A., et al. Nature, 407: 319, 2000, Wesley, S. V. et al. Plant J. 27: 581, 2001, Piccin, A. et al. Nucleic Acids Res. 29: E55, 2001).

The DNA encoding the dsRNA of the present invention does not necessarily have to have completely the same base sequence as that of the target gene, but the homology of the sequences is at least 70% or more, preferably 80% or more, and further preferably 90% or more (for example, 95%, 96%, 97%, 98%, 99% or more). The homology of the sequences can be determined with the above-described procedure (BLAST program).

In the dsRNA, a double-stranded RNA portion where RNAs are paired may include not only RNAs which are completely paired, but also an unpaired portion by a mismatch (corresponding bases are not complementary to each other), a bulge (one strand does not have a corresponding base), or the like. In the present invention, the double-stranded RNA region where RNAs of the dsRNA are paired may include both a bulge and a mismatch.

Another form of the DNA encoding an RNA having an activity of providing a plant with susceptibility to a 4-HPPD inhibitor is a DNA (antisense DNA) encoding an antisense RNA complementary to a transcript of the endogenous resistance DNA of the present invention. Examples of an action by the antisense DNA to suppress an expression of the target gene include: inhibition of transcription initiation by triple strand formation; suppression of transcription by hybrid formation at a site where an open loop structure is locally formed by an RNA polymerase; inhibition of transcription by hybrid formation with an RNA being synthesized; suppression of splicing by hybrid formation at a boundary between an intron and an exon; suppression of splicing by hybrid formation at a site where a spliceosome is formed; suppression of translocation from the nucleus to the cytoplasm by hybrid formation with mRNA; suppression of splicing by hybrid formation at a capping site or poly (A) addition site; suppression of translation initiation by hybrid formation at a binding site for a translation initiation factor; suppression of translation by hybrid formation at a ribosome binding site near the start codon; inhibition of peptide chain elongation by hybrid formation in a translated region and at a polysome binding site of mRNA; suppression of gene expression by hybrid formation at a site where a nucleic acid interacts with a protein; and the like. These inhibit a process of transcription, splicing, or translation, and suppress an expression of the target gene (Hirajima and Inoue, "Shin Seikagaku Jikken Kouza (New Courses in Biochemistry Experiments) 2, Kakusan (nucleic acid) IV, Idenshi no Fukusei to Hatsugen (Gene Replication and Expression)", edited by the Japanese Biochemical Society, Tokyo Kagaku Dojin, pp. 319-347, 1993). The antisense DNA used in the present invention may suppress an expression of the target gene by any of the aforementioned actions. As one mode, if an antisense sequence is designed complementary to an untranslated region near the 5' end of an mRNA of the target gene, it will effectively inhibit translation of the gene. Nevertheless, it is also possible to use a sequence complementary to an untranslated region on the 3' side or a coding region. As described above, the antisense DNA utilized in the present invention also includes a DNA containing an antisense sequence for sequences of not only a translated region but also an untranslated region of the gene. The antisense DNA used is linked downstream of an appropriate promoter, and preferably a sequence containing a transcription termination signal is linked on the 3' side.

The antisense DNA can be prepared based on the sequence information on the resistance DNA of the present invention (for example, DNA having the base sequence of SEQ ID NO: 1) by a phosphorothioate method (Stein, Nucleic Acids Res., 16: 3209-3221, 1988) or the like. The DNA thus prepared can be introduced into a plant by known methods described later. The sequence of the antisense DNA is preferably a sequence complementary to a transcript of the endogenous resistance DNA of the present invention of the plant, but does not have to be completely complementary, as long as the gene expression can be effectively inhibited. Transcribed RNA has a complementarity of preferably 90% or more (for example, 95%, 96%, 97%, 98%, 99% or more) to a transcript of the target gene. In order to effectively inhibit an expression of the target gene, the length of the antisense DNA is at least 15 bases or longer, preferably 100 bases or longer, and further preferably 500 bases or longer. Generally, the length of the antisense DNA used is shorter than 5 kb, preferably shorter than 2.5 kb.

Another form of the DNA encoding an RNA having an activity of providing a plant with susceptibility to a 4-HPPD inhibitor, is a DNA encoding an RNA having a ribozyme activity of specifically cleaving a transcript of the endogenous resistance DNA of the present invention. Ribozymes include one having a size of 400 nucleotides or longer such as group I intron type and M1RNA included in RNaseP, and also one called a hammer-head or hairpin type having an active domain of approximately 40 nucleotides (Makoto Koizumi and Eiko Ohtsuka, Tanpakushitu Kakusan Koso (Protein, Nucleic Acid, Enzyme), 35: 2191, 1990).

For example, a self-cleaving domain of a hammer-head type ribozyme cleaves the 3' side of C15 of G13U14C15; but for the activity, it is important that U14 and A at position 9 form a base pair, and the base at position 15 is shown to be cleaved if A or U is in place of C (Koizumi et al., FEBS Lett. 228: 225, 1988). A restriction enzyme-like RNA-cleaving ribozyme that recognizes a sequence such as UC, UU, or UA in the target RNA can be produced if a substrate binding site of the ribozyme is designed complementary to the RNA sequence near the target site (Koizumi et. al., FEBS Lett. 239: 285, 1988, Makoto Koizumi and Eiko Ohtsuka, Tanpakushitu Kakusan Koso (protein, nucleic acid, enzyme), 35: 2191, 1990, Koizumi et. al., Nucleic. Acids. Res. 17: 7059, 1989).

Meanwhile, a hairpin-type ribozyme is also useful for the object of the present invention. The hairpin-type ribozyme is found, for example, in the minus strand of tobacco ringspot virus satellite RNA (Buzayan, Nature 323: 349, 1986). It has been shown that this ribozyme can also be designed such that target-specific RNA cleavage occurs (Kikuchi and Sasaki, Nucleic Acids Res. 19: 6751, 1992, Yo Kikuchi, Kagaku to Seibutsu (Chemistry and Biology) 30: 112, 1992). The ribozyme designed to be capable of cleaving the target is linked to a promoter such as a cauliflower mosaic virus 35S promoter and a transcription termination sequence so that the ribozyme can be transcribed in plant cells. The effect can be increased by arranging such constituent units in tandem so that multiple sites can be cleaved in the target gene (Yuyama et al., Biochem. Biophys. Res. Commun. 186: 1271, 1992). Such a ribozyme is used to specifically cleave the target transcript of the endogenous resistance DNA of the present invention, so that an expression of the DNA can be suppressed.

<Vector having DNA According to Present Invention Inserted Therein>

The vector having the DNA of the present invention (the resistance DNA of the present invention, or the DNA encoding an RNA having an activity of providing a plant with susceptibility to a 4-HPPD inhibitor) inserted therein is not particularly limited, as long as the inserted gene can be expressed in a plant cell. The vector according to the present invention may comprise a promoter for stably or inductively expressing the DNA of the present invention. Examples of the promoter for stable expression include a cauliflower mosaic virus 35S promoter, a rice actin promoter, a corn ubiquitin promoter, and the like. Meanwhile, examples of the promoter for inductive expression include promoters known to be expressed by external factors such as infection and invasion of filamentous fungi, bacteria, and viruses, low temperature, high temperature, dryness, ultraviolet irradiation, and spraying of a certain compound; and other promoters. Examples of such promoters include a rice chitinase gene promoter and a tobacco PR protein gene promoter expressed by infection and invasion of filamentous fungi, bacteria, and virus; a rice lip19 gene promoter induced by low temperature; rice hsp80 gene and hsp72 gene promoters induced by high temperature; an *Arabidopsis thaliana* rab16 gene promoter induced by dryness; a parsley chalcone synthase gene promoter induced by ultraviolet irradiation; a corn alcohol dehydrogenase gene promoter induced by an anaerobic condition; and the like. In addition, the rice chitinase gene promoter and the tobacco PR protein gene promoter may also be induced by a particular compound such as salicylic acid, and rab16 may also be induced by spraying a plant hormone, abscisic acid.

The agent of the present invention may be by itself the DNA of the present invention or the vector having the DNA inserted therein, or may comprise other components mixed therewith. Such other components are not particularly limited, and examples thereof include sterile water, a saline, a vegetable oil, a surfactant, a lipid, a solubilizer, a buffer, and a preservative. Furthermore, when a transgenic plant cell of the present invention is prepared by an Agrobacterium-mediated method described below, the agent may comprise Agrobacterium having the DNA introduced therein.

<Transgenic Plant Cell of the Present Invention>

A transgenic plant cell capable of regenerating a plant having increased resistance to a 4-HPPD inhibitor of the present invention is a plant cell transformed by introducing therein the resistance DNA of the present invention or a vector having the DNA inserted therein, the DNA encoding a protein having an activity of providing a plant with resistance to a 4-HPPD inhibitor.

In addition, a transgenic plant cell capable of regenerating a plant having increased susceptibility to a 4-HPPD inhibitor of the present invention is a plant cell transformed by introducing therein the above DNA or a vector having the DNA inserted therein, the DNA encoding an RNA having an activity of providing a plant with susceptibility to a 4-HPPD inhibitor.

A plant, from which the plant cell of the present invention is derived, is not particularly limited, and examples thereof include Poaceae plants such as rice, barley, wheat, sorghum, corn, and creeping bentgrass; Brassicaceae plants such as *Arabidopsis thaliana;* Solanaceae plants such as tomato; Fabaceae plants such as soybean, alfalfa, and *Lotus japonicas;* Malvaceae plants such as cotton plant; and Chenopodiaceae plants such as sugar beet.

Particularly, 4-HPPD inhibitor-susceptible cultivars of these plants are preferable as a target of the present invention whose resistance to a 4-HPPD inhibitor is to be increased. Examples of a 4-HPPD inhibitor-susceptible rice cultivar include Habataki, Takanari, Momiroman, Mizuhochikara, Ruriaoba, Odorokimochi, Hyogo-ushiwakamaru, Kasalath, and Kanto 239, but are not limited thereto.

Meanwhile, particularly 4-HPPD inhibitor-resistant cultivars of these plants are preferable as a target of the present invention whose susceptibility to a 4-HPPD inhibitor is to be increased. Examples of a 4-HPPD inhibitor-resistant rice cultivar include Nipponbare, Koshihikari, Kitaaoba, Akihikari, Akitakomachi, Fukuhibiki, Bekoaoba, Bekogonomi, Yumeaoba, Hokuriku 193, Leaf Star, Tachisugata, Kusanohoshi, Hoshiaoba, Nishiaoba, Tachiaoba, Makimizuho, Mogumoguaoba, Hamasari, and Minamiyutaka, but are not limited thereto.

The plant cell of the present invention includes, besides culture cells, cells in the plants. Further, the plant cell of the present invention includes plant cells in various forms, for example, suspended culture cells, protoplasts, leaf sections, calli, immature embryos, pollens, and the like.

As a method for introducing the vector having the resistance DNA of the present invention inserted therein into the plant cell, it is possible to use various methods known to those skilled in the art, such as a polyethylene glycol method, an electroporation method, an *Agrobacterium*-mediated method, and a particle gun method.

<Plant of Present Invention, Propagation Material thereof, and Method for Producing the Plant>

The present invention provides a plant regenerated from the above transgenic plant cell (hereinafter also referred to as transgenic plant). The plant can be regenerated from the transgenic plant cell by methods known to those skilled in the art, depending on the type of the plant cell.

For example, several techniques of the procedure for producing transgenic rice plants have been already established, such as a method in which a gene is introduced into protoplasts using polyethylene glycol and a plant is regenerated (Datta, S. K. In Gene Transfer To Plants (Potrykus I and Spangenberg Eds.) pp 66-74, 1995); a method in which a gene is introduced into protoplasts using electric pulse and a plant is regenerated (Toki et al. Plant Physiol. 100, 1503-1507, 1992); a method in which a gene is directly introduced into cells by a particle gun method and a plant is regenerated (Christou et al. Bio/technology, 9: 957-962, 1991); and a method in which a gene is introduced using *Agrobacterium* and a plant is regenerated (Hiei et al. Plant J. 6: 271-282, 1994). These are widely used in the technical field of the present invention.

Moreover, examples of the procedure for producing transgenic plants of barley includes methods described in Tingay et al. (Tingay S. et al. Plant J. 11: 1369-1376, 1997), Murray et al. (Murray F et al. Plant Cell Report 22: 397-402, 2004), and Travalla et al. (Travalla S et al. Plant Cell Report 23: 780-789, 2005).

As the method for regenerating sorghum plants, preferably used are, for example, a method in which a gene is introduced into immature embryos or calli by an *Agrobacterium* method or a particle gun method and a plant is regenerated; and a method in which pollens having a gene introduced therein using ultrasound are used for pollination (J. A. Able et al., In Vitro Cell. Dev. Biol. 37: 341-348, 2001, A. M. Casas et al., Proc. Natl. Acad. Sci. USA 90: 11212-11216, 1993, V. Girijashankar et al., Plant Cell Rep 24: 513-522, 2005, Je. M. JEOUNG et al., Hereditas 137: 20-28, 2002, V Girijashankar et al., Plant Cell Rep 24 (9): 513-522, 2005, Zuo-yu Zhao et al., Plant Molecular Biology 44: 789-798, 2000, S. Gurel et al., Plant Cell Rep 28 (3): 429-444, 2009, Z Y Zhao, Methods Mol Biol, 343: 233-244, 2006, A K Shrawat and H Lorz, Plant Biotechnol J, 4 (6): 575-603, 2006, D Syamala and P Devi Indian J Exp Biol, 41 (12): 1482-1486, 2003, Z Gao et al., Plant Biotechnol J, 3 (6): 591-599, 2005).

Further, an example of the procedure for *Arabidopsis thaliana* includes a method by Akama et al. (Akama et al. Plant Cell Reports 12: 7-11, 1992). In the present invention, these methods can be preferably used.

Once a plant having the DNA of the present invention introduced in the genome is obtained, it is possible to obtain a progeny from the plant by sexual reproduction or asexual reproduction. In addition, propagation materials (for example, seeds, fruits, spikes, stubs, calli, protoplasts, and the like) are obtained from the plant or a progeny or a clone thereof, from which the plant can also be produced in mass. Thus, the present invention includes plant cells comprising the DNA of the present invention, plants comprising the cells, progenies and clones of the plants, as well as propagation materials of the plants, the progenies, and the clones.

Moreover, the present invention also provides a method for producing a plant having increased resistance to a 4-HPPD inhibitor, wherein the method comprises:

(I) a step of introducing into a plant cell the resistance DNA of the present invention or a vector having the DNA inserted therein; and (II) a step of regenerating a plant from the transgenic plant cell in which the DNA or the vector having the DNA inserted therein has been introduced into in step (I).

Furthermore, the present invention also provides a method for producing a plant having increased susceptibility to a 4-HPPD inhibitor, wherein the method comprises:

(I) a step of introducing into a plant cell the DNA encoding an RNA having an activity of providing a plant with susceptibility to a 4-HPPD inhibitor or a vector having the DNA inserted therein; and (II) a step of regenerating a plant from the transgenic plant cell in which the DNA or the vector having the DNA inserted therein has been introduced in step (I).

<Method for Determining Whether Plant Has Resistance or Susceptibility to 4-HPPD Inhibitor>

A method for determining whether a plant has resistance or susceptibility to a 4-HPPD inhibitor of the present invention is characterized in that the method comprises analyzing a base sequence of the resistance DNA of the present invention or a corresponding susceptibility DNA (hereinafter referred to as detection target DNA of the present invention) in a test plant or a base sequence of an expression control region of the DNA. Note that a "susceptibility DNA" is a DNA, encoding a protein having an activity of providing a plant with susceptibility to a 4-HPPD inhibitor.

The detection target DNA of the present invention is typically at least one DNA selected from the group consisting of the following (a) to (d):

(a) a DNA encoding a protein having an amino acid sequence of any one of SEQ ID NOs: 2 and 17;

(b) a DNA encoding a protein having an amino acid sequence of any one of SEQ ID NOs: 2 and 17, in which one or more amino acids are substituted, deleted, added, and/or inserted;

(c) a DNA hybridizing under stringent conditions to a DNA having a base sequence of any one of SEQ ID NOs: 1 and 16; and (d) a DNA encoding an amino acid sequence having a homology of 60% or more with an amino acid sequence of any one of SEQ ID NOs: 2 and 17.

Note that the DNAs of (a) to (d) basically mean ones as described above, but particularly mean an endogenous DNA regarding the detection target DNA of the present invention, and mean to include both the resistance DNA and the susceptibility DNA.

As illustrated in Examples described later, in comparison with the HIS1 gene of a 4-HPPD inhibitor-resistant cultivar Nipponbare, base insertion or deletion is observed in the sequences of the corresponding genes of 4-HPPD inhibitor-susceptible cultivars Momiroman, Takanari, and Kasalath. Thus, analyzing the base sequence of the detection target DNA of the present invention makes it possible to determine whether a plant has resistance or susceptibility to a 4-HPPD inhibitor.

Moreover, as illustrated in Examples described later, the susceptibility to a 4-HPPD inhibitor is inherited in a recessive manner. Accordingly, analyzing an expression level of the detection target DNA of the present invention as well as the base sequence of a region (enhancer, promoter, silencer, insulator) controlling the expression level also makes it possible to determine whether a plant has resistance or susceptibility to a 4-HPPD inhibitor.

In analyzing the base sequence of the detection target DNA of the present invention or the expression control region, it is possible to use an amplification product of the detection target DNA of the present invention or the expression control region amplified by PCR. When the PCR is carried out, a primer used is not limited, as long as the detection target DNA of the present invention or the expression control region can be amplified specifically. The primer can be designed as appropriate based on the sequence information (for example, SEQ ID NO: 1) of the detection target DNA of the present invention or the expression control region. Examples of a preferable primer include a primer having a base sequence of SEQ ID NO: 13 and a primer having a base sequence of SEQ ID NO: 14. By combining these primers as appropriate, a particular base sequence of the detection target DNA of the present invention or the expression control region can be amplified.

Note that determining whether a test plant has resistance or susceptibility to a 4-HPPD inhibitor may comprise, for example, a comparison step with a "control base sequence." The "control base sequence" compared with the base sequence of the detection target DNA of the present invention or the expression control region in a test plant is typically the base sequence of the detection target DNA of the present invention or the expression control region of, in a case of rice, a 4-HPPD inhibitor-resistant cultivar (for example, Nipponbare, Koshihikari, Kitaaoba, Akihikari, Akitakomachi, Fukuhibiki, Bekoaoba, Bekogonomi, Yumeaoba, Hokuriku 193, Leaf Star, Tachisugata, Kusanohoshi, Hoshiaoba, Nishiaoba, Tachiaoba, Makimizuho, Mogumoguaoba, Hamasari, Minamiyutaka) or a 4-HPPD inhibitor-susceptible cultivar (for example, Habataki, Takanari, Momiroman, Mizuhochikara, Ruriaoba, Odorokimochi, Hyogo-ushiwakamaru, Kasalath, Kanto 239).

Note that, as an example of the susceptibility DNA of the present invention, the base sequence of a hypothetical gene (mutated HIS1 gene) of an iron/ascorbate-dependent oxidoreductase gene derived from Takanari or Momiroman is shown in SEQ ID NO: 15.

By comparing the determined base sequence of the detection target DNA of the present invention or the expression control region in the test plant with the base sequence (for example, SEQ ID NO: 1, SEQ ID NO: 16) of 4-HPPD inhibitor-resistant cultivars or the base sequence (for example, SEQ ID NO: 15) of 4-HPPD inhibitor-susceptible cultivars, whether the test plant has resistance or susceptibility to a 4-HPPD inhibitor can be evaluated. For example, if the base sequence is greatly different (particularly, if the molecular weight or the amino acid sequence of the encoded protein is greatly changed due to occurrence of anew stop codon or a frame shift) in comparison with the base sequence (for example, SEQ ID NO: 1) of a 4-HPPD inhibitor-resistant cultivar, the test plant is determined to be highly likely to have susceptibility to a 4-HPPD inhibitor.

Note that, in the determination method of the present invention, a DNA can be prepared from a test plant by using ordinary methods, for example, the CTAB method. As a plant from which a DNA is prepared, it is possible to use not only a grown plant, but also a seed and a seedling. Moreover, the base sequence can be determined by ordinary methods, for example, the dideoxy method, the Maxam-Gilbert method, or the like. In determining the base sequence, commercially-available sequencing kits and sequencers can be utilized.

Whether or not the base sequence of the detection target DNA of the present invention or the expression control region in a test plant is different from the control base sequence can be indirectly analyzed by various methods, besides directly determining the base sequence as described above. Examples of such methods include the PCR-SSCP (single-strand conformation polymorphism) method, the RFLP method or PCR-RFLP method utilizing Restriction Fragment Length Polymorphism (RFLP), denaturant gradient gel electrophoresis (DGGE), Allele Specific Oligonucleotide (ASO) hybridization method, and the ribonuclease A mismatch cleavage method.

Another method for determining whether a plant has resistance or susceptibility to a 4-HPPD inhibitor of the present invention is characterized in that the method comprises detecting an expression of at least one DNA, in a test plant, selected from the group consisting of the above (a) to (d), or a molecular weight of any one of an amplification product and an expression product of the DNA.

As illustrated in Examples described later, a front half region of the fourth exon of the HIS1 gene of each 4-HPPD inhibitor-resistant cultivar of Nipponbare, Koshihikari, and Hokuriku 193 is longer than those of 4-HPPD inhibitor-susceptible cultivars Momiroman and Takanari. Thus, detecting the molecular weight of any one of the amplification product and the expression product of the detection target DNA of the present invention makes it possible to determine whether the plant has resistance or susceptibility to a 4-HPPD inhibitor.

Moreover, as illustrated in Examples described later, the susceptibility to a 4-HPPD inhibitor is inherited in a recessive manner. Accordingly, detecting an expression of the detection target DNA of the present invention makes it possible to determine whether a plant has resistance or susceptibility to a 4-HPPD inhibitor.

Herein, the phrase "detecting an expression of DNA" means to include both detecting at a transcription level and detecting at a translation level. Moreover, the phrase "detecting an expression" means to include not only detecting presence or absence of an expression, but also detecting the degree of the expression.

The detection target DNA of the present invention (for example, genomic DNA) can be amplified by the PCR (Polymerase chain reaction) method.

The DNA according to the present invention can be detected at a transcription level by ordinary methods, for example, the RT-PCR (Reverse transcribed-Polymerase chain reaction) method or the northern blotting method. A primer used when the PCR is carried out is not limited, as long as the detection target DNA of the present invention can be amplified specifically. The primer can be designed as appropriate based on the sequence information (for example, SEQ ID NO: 1, SEQ ID NO: 16, SEQ ID NO: 15) of the resistance DNA or the susceptibility DNA of the present invention having been determined already. Examples of a preferable primer include primers having a base sequence of any of SEQ ID NOs: 3 to 14. Moreover, by combining these primers as appropriate, a particular base sequence of the detection target DNA of the present invention can be amplified.

Meanwhile, detection at a translation level can be performed by ordinary methods, for example, the western blotting method. An antibody used in western blotting may be a polyclonal antibody or a monoclonal antibody. Methods for preparing these antibodies are well-known to those skilled in the art.

In addition, an expression of the detection target DNA of the present invention can be determined by: constructing a vector having a reporter gene expressibly linked downstream of the expression control region of the detection target DNA of the present invention; introducing the vector into a plant cell; and detecting the reporter activity.

As a result of detecting a gene expression, if the expression level of the detection target DNA of the present invention of the test plant is significantly lower than the expression level of a 4-HPPD inhibitor-resistant cultivar (for example, in a case of rice, Nipponbare, Koshihikari, Kitaaoba, Akihikari, Akitakomachi, Fukuhibiki, Bekoaoba, Bekogonomi, Yumeaoba, Hokuriku 193, Leaf Star, Tachisugata, Kusanohoshi, Hoshiaoba, Nishiaoba, Tachiaoba, Makimizuho, Mogumoguaoba, Hamasari, Minamiyutaka) (for example, if the detection target DNA of the present invention is not substantially expressed), or if the molecular weight of any one of the amplification product and the expression product of the detection target DNA of the present invention is significantly different from the molecular weight in the 4-HPPD inhibitor-resistant cultivar (for example, Nipponbare, Koshihikari, Kitaaoba, Akihikari, Akitakomachi, Fukuhibiki, Bekoaoba, Bekogonomi, Yumeaoba, Hokuriku 193, Leaf Star, Tachisugata, Kusanohoshi, Hoshiaoba, Nishiaoba, Tachiaoba, Makimizuho, Mogumoguaoba, Hamasari, Minamiyutaka), the test plant is determined to be highly likely to have susceptibility to a 4-HPPD inhibitor. In fact, as illustrated in Examples described later, the molecular weight of the susceptibility DNA of the 4-HPPD inhibitor-susceptible cultivars (Momiroman, Takanari) is significantly low in comparison with the resistance DNA of the 4-HPPD inhibitor-resistant cultivars (Nipponbare, Koshihikari, Hokuriku 193).

<Method for Breeding Plant of Present Invention>

The present invention provides a method for breeding a plant having increased resistance to a 4-HPPD inhibitor. The breeding method comprises:

(a) a step of crossing a plant cultivar resistant to a 4-HPPD inhibitor with any plant cultivar;

(b) a step of determining whether individuals obtained by the crossing have resistance or susceptibility to a 4-HPPD inhibitor by the above determination method of the present invention; and (c) a step of selecting a cultivar determined to have resistance to the 4-HPPD inhibitor.

Moreover, the present invention provides a method for breeding a plant having increased susceptibility to a 4-HPPD inhibitor. The breeding method comprises:

(a) a step of crossing a plant cultivar susceptible to a 4-HPPD inhibitor with any plant cultivar;

(b) a step of determining whether individuals obtained by the crossing have resistance or susceptibility to a 4-HPPD inhibitor by the above determination method of the present invention; and (c) a step of selecting a cultivar determined to have susceptibility to the 4-HPPD inhibitor.

Examples of "any plant cultivar" crossed with the plant cultivar resistant to a 4-HPPD inhibitor include 4-HPPD inhibitor-susceptible cultivars, and individuals obtained by crossing 4-HPPD inhibitor-resistant cultivars with 4-HPPD inhibitor-susceptible cultivars, but are not limited thereto. Moreover, examples of "any plant cultivar" crossed with the plant cultivar susceptible to a 4-HPPD inhibitor include 4-HPPD inhibitor-resistant cultivars, and individuals obtained by crossing 4-HPPD inhibitor-resistant cultivars with 4-HPPD inhibitor-susceptible cultivars, but are not limited thereto. Since the susceptibility to a 4-HPPD inhibitor is inherited in a recessive manner, in order for individuals obtained by the crossing to show susceptibility to the 4-HPPD inhibitor, it is preferable to have the 4-HPPD inhibitor-susceptibility HIS1 gene homozygously.

A utilization of the breeding method of the present invention makes it possible to select a 4-HPPD inhibitor-resistant or -susceptible cultivar at the stage of seed or seedling, hence making it possible to breed a cultivar having the trait in a short period of time.

EXAMPLES

Hereinafter, the present invention will be described more specifically based on Examples. However, the present invention is not limited to the following Examples. Meanwhile, the experiments and analyses in the following Examples were carried out as follows.

<QTL Analysis>

A Koshihikari/Habataki chromosome segment substitution line and Tachisugata//Tachisugata/Momiroman BC1F4 were tested. Specifically, Koshihikari/Habataki chromosome segment substitution lines (KHSL) were analyzed, in which a portion of chromosome fragments of a resistant cultivar Koshihikari serving as the genetic background was substituted with a chromosome of an indica type susceptible cultivar Habataki. Note that KHSL consists of 32 lines, and enables analysis on all of the whole 12 chromosomes of Habataki (as to KHSL, see Kazumasa Murata et al., "Development and evaluation of CSSLs carrying overlapping chromosome segments of rice cultivar Habataki in a genetic background of cultivar Koshihikari, " Breeding Research, Mar. 27, 2009, vol. 11, supplement issue 1, p. 66). In addition, 94 BC1F4 lines obtained by one-time backcrossing of a resistant cultivar Tachisugata to a susceptible cultivar Momiroman were analyzed using 80 SSR markers (as to the SSR markers used, see "Development and mapping of 2240 new SSR markers for rice (*Oryza sativa* L.)", DNA Res, 2002, vol. 9, iss. 6, pp. 199 to 207, and http://www.gramene.org/).

<Linkage Analysis Using Tos17-Inserted Lines>

A retrotransposon Tos17 discovered in rice is activated by tissue culture, and its copies are transposed into a genome. It is known that when the transposition site is inside a gene, the gene is to be disrupted, causing a mutation (see Hirochika et al., Proc. Natl. Acad. Sci. USA, 1996, vol. 93, pp. 7783 to 7788). The present Examples utilized a rice population having accumulated mutations caused by tissue culture utilizing the phenomenon (mutant panel, database name: Tos17 mutant panel database (http://tos.nias.affrc.go.jp/ to miyao/pub/tos17/)). From the Tos17 mutant panel database, two lines were selected, in each of which Tos17 was inserted in a transcription site of a hypothetical gene of an iron/ascorbate oxidoreductase gene, which was strongly suspected of being associated with BBC susceptibility located at a gene locus specified by the QTL analysis. Then, self-fertilized seeds obtained by planting 15 individuals of each of these two lines were used to examine phenotype (BBC susceptibility) and genotype (Tos17 insertion).

<Acquisition of Gene Clone>

A hypothetical mRNA (AK065581) of the iron/ascorbate-dependent oxidoreductase gene located at the gene locus specified by the QTL analysis was obtained from a rice gene bank.

<Vector Construction and Transformation>

For transformation by an Agro method, binary vectors were constructed by linking an expression cassettes a kanamycin resistance gene (NPT2) driven by a nos promoter or a hygromycin resistance gene (mHPT) driven by a CaMV35S promoter to that of AK065581 (HIS1 gene) or AK241948 (HSL1 gene), which were driven by a CaMV35S promoter (see FIGS. 3 to 7).

For transformation of *A. thaliana*, ecotype "Columbia" was used, and a Floral dip method was performed (see Weigel and Glazebrook, *Arabidopsis*, a laboratory manual, Cold Spring Harbor Laboratory Press (2002) p131-132). Specifically, first, *Agrobacterium* was shake-cultured in a liquid medium (LB or YEB) containing an antibiotic. Approximately 16 hours later, 2 ml of the culture solution was added to a liquid medium (LB or YEB) containing an antibiotic, and further shake-cultured. Then, the culture solution obtained approximately 16 hours thereafter was centrifuged at 8000 rpm at 4° C. for 10 minutes. The supernatant liquid was discarded, and the resulting precipitate was suspended in 500 ml of a solution containing 5% sucrose. Subsequently, immediately before the transformation, a transformation reagent silwet (registered trademark: SILWET L-77, product number: BMS-SL7755, manufactured by Bio Medical Science Inc.) was added thereto at a final concentration of 0.025%. Then, into the *Agrobacterium* suspension thus obtained, *Arabidopsis* from which already flowered and pollinated buds had been removed was dipped for 30 to 120 seconds. Thereafter, the plants were left standing for 16 hours and then grown to obtain the seeds.

For transformation of rice, a BBC susceptible rice cultivar Kanto 239 was used, and the method described in "Taniguchi et al., Plant Cell Rep., 2010, vol. 29, iss. 11, pp. 1287 to 1295" was performed with some modification. Specifically, first, sterilized mature seeds were sown on an N6D medium. After culturing at 30° C. for 7 days, the seeds were infected with *Agrobacterium*, and co-cultured in an acetosyringone (AS)-containing N6 medium (2N6-AS medium) under a dark condition at 25° C. for 3 days. Thereafter, the infected tissues were cultured in a carbenicillin-containing N6D medium for 4 to 6 weeks (18 hours day length) in the presence of 40 mg/L hygromycin (Hyg), and Hyg-tolerant calli were re-differentiated.

Figure 5:
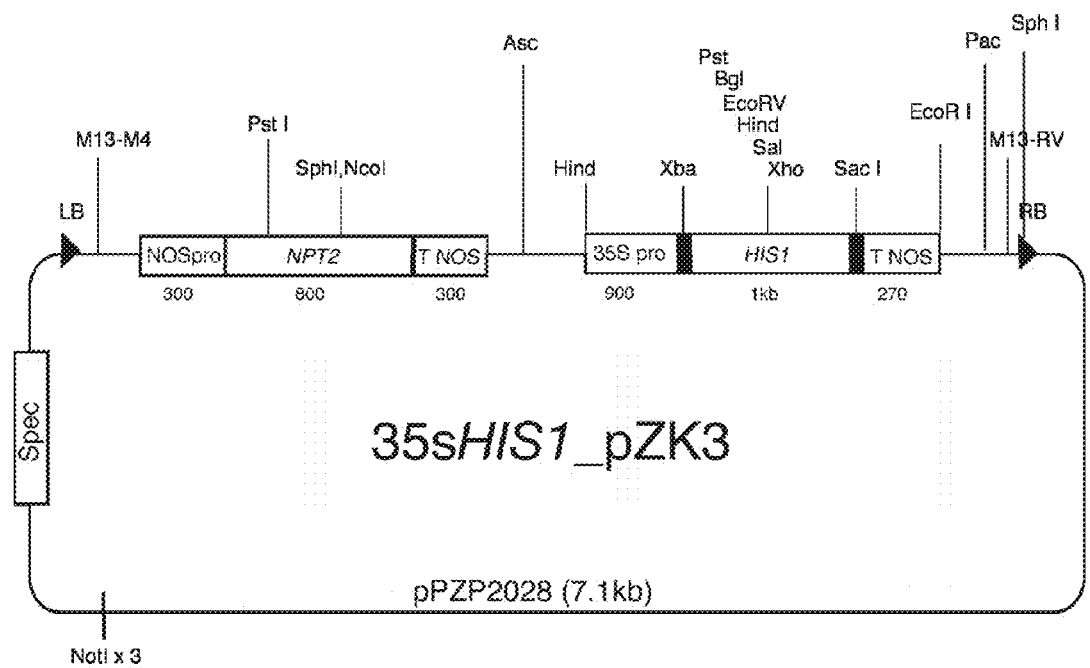
FIG. 5 is a representation for illustrating a schematic of a binary vector (35sHIS1 pZK3) used for transformation of tomatoes by the *Agrobacterium* method, the binary vector obtained by linking boundary sequences (RB: right boundary sequence, LB: left boundary sequence) to expression cassettes of a kanamycin resistance gene (NPT2) driven by a nos promoter (NOSpro) and AK065581 (HIS1) driven by a CaMV35S promoter (35S Pro).
Figure 6:
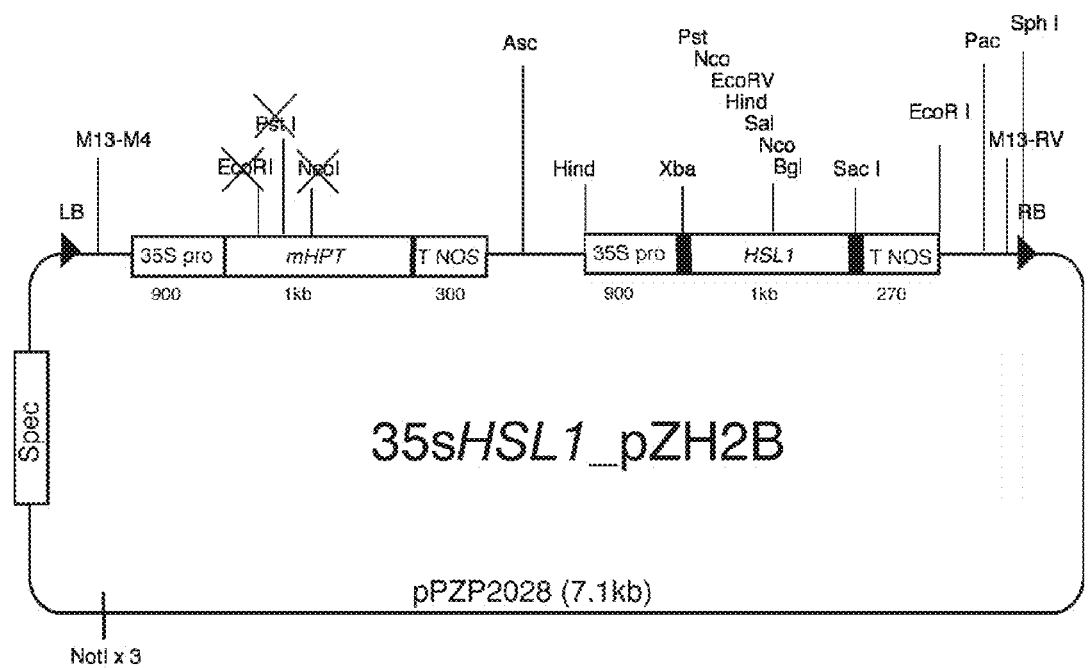
FIG. 6 is a representation for illustrating a schematic of a binary vector (35sHSL1 pZH2B) used for transformation of *Arabidopsis thaliana* and rice by the *Agrobacterium* method, the binary vector obtained by linking boundary sequences (RB: right boundary sequence, LB: left boundary sequence) to expression cassettes of a hygromycin resistance gene (mHPT) driven by a CaMV35S promoter (35S Pro) and AK241948 (HSL1) driven by a CaMV35S promoter (35S Pro).
Figure 7:
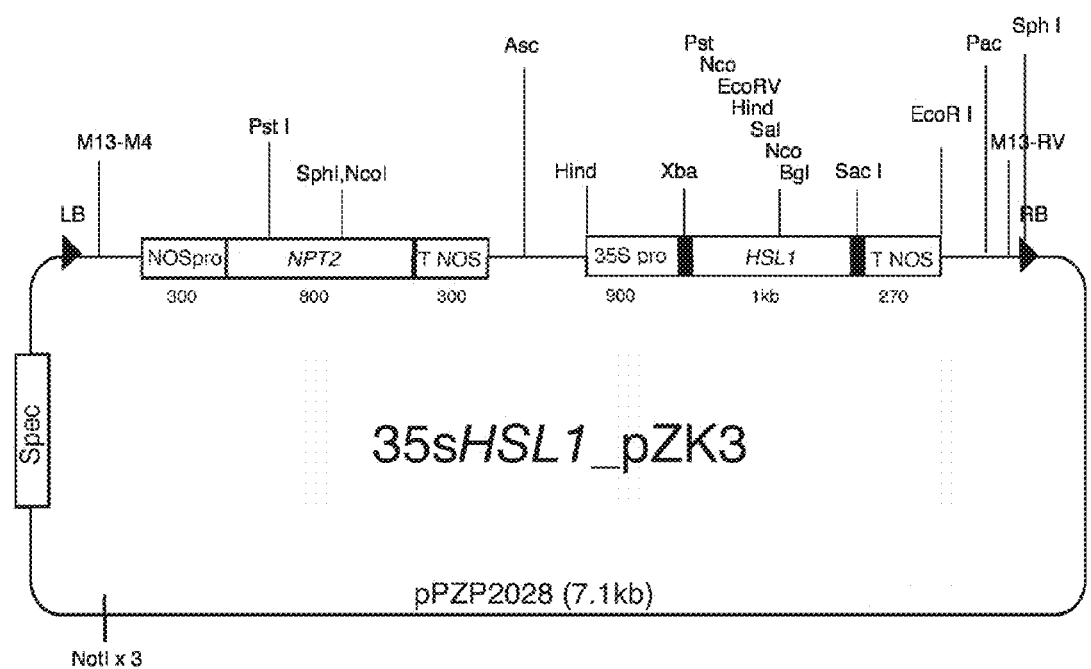
FIG. 7 is a representation for illustrating a schematic of a binary vector (35sHSL1 pZK3) used for transformation of tomatoes by the *Agrobacterium* method, the binary vector obtained by linking boundary sequences (RB: right boundary sequence, LB: left boundary sequence) to expression cassettes of a kanamycin resistance gene (NPT2) driven by a nos promoter (NOSpro) and AK241948 (HSL1) driven by a CaMV35S promoter (35S Pro).

For transformation of tomatoes, a cultivar "Micro-Tom" was tested, and an *Agrobacterium* method was performed using vectors (35SHIS1pZK3, 35SHSL1pZK3) shown in FIGS. 5 and 7. Note that when seeds of the original cultivar Micro-Tom were germinated on an agar medium containing 0.3 µM benzobicyclon (BBC) using an incubator at 25° C., it was clearly observed approximately 2 weeks later that leaf parts thereof were whitened.

As a result of the tomato transformation, multiple re-differentiated plants having the HIS1 gene or the HSL1 gene introduced therein were obtained. Moreover, the genes introduced into the re-differentiated plants were confirmed by PCR <BBC Resistance Assay on Recombinants>

*A. thaliana* recombinants (T2 generation) and rice recombinants (T0 generation) were produced and subjected to a BBC resistance assay using a BBC substance possessed by SDS Biotech K.K. at a concentration to be described later.

<Triketone Type 4-HPPD Inhibitor-Resistance Assay on Recombinants>

Rice recombinants (T1 and T2 generations) were produced and subjected to a resistance assay with triketone type 4-HPPD inhibitors, that is, mesotrione, tefuryltrione, tembotrione, and NTBC, using commercially-available reagents at concentrations to be described later.

<PCR>

Primers specifically amplifying five exon regions of HIS1 (AK065581) were designed and used for PCR. Note that the PCR was carried out in 35 cycles each consisting of 94° C. for 30 seconds, 55° C. for 30 seconds, and 72° C. for 30 seconds, using the primers having base sequences shown in Table 1. Moreover, as the template DNAs, used were genomic DNAs extracted by the CTAB method from leaves of BBC susceptible rice cultivars (Momiroman, Takanari, Kasalath) and BBC resistant rice cultivars (Nipponbare, Koshihikari, Hokuriku 193).

TABLE 1

| Amplification target | Sequence | SEQ ID NO |
|---|---|---|
| exon 1 of HIS1 gene | CTAGCTCCCCAAGTCGAAAC ATGGGGTGAACTCACATGG | 3 4 |
| exon 2 of HIS1 gene | GCAGGCTATAGATGAGCTGAAA CAGGAAGAAGCCCCAATTCT | 5 6 |
| exon 3 of HIS1 gene | CTTACCAACCATGGAGTAGAAGC TGAAAGATTCAGGATGGTCAG | 7 8 |
| exon 4 of HIS1 gene | GTTCTGAACAAGTATGCATCAGGA GGTGTCACCTAAGTTGATCAGCAAT | 9 10 |
| exon 5 of HIS1 gene | GGGTTTCTGAATGCTGATGC TGCCTTGAAACGTGAGAACG | 11 12 |
| front half of exon 4 of HIS1 gene | TGTTGTCTGAATTCAGAAAGTAC TCCTCATCAAGCTCAAGAAGC | 13 14 |

Example 1

Specifying 4-HPPD Inhibitor-Resistance Gene Locus

Among *japonica* type rice, no cultivar is known to have susceptibility to BBC, one of 4-HPPD inhibitors. Meanwhile, a rice cultivar bred by crossing a *japonica* type with an indica type may have BBC susceptibility.

Accordingly, the QTL analysis was performed as described above on the Koshihikari/Habataki chromosome segment substitution lines (KHSL) using the BBC resistant rice cultivar "Koshihikari" and the susceptible rice cultivar "Habataki". As a result, only KHSL (KHSL04) whose short arm region of chromosome 2 was substituted with that of the Habataki type showed susceptibility. This revealed that the gene locus for determining the BBC resistance was located on a short arm of chromosome 2 of Koshihikari (see Table 2). Note that Table 2 shows part of the result of the QTL analysis on the KHSL. Additionally, in Table 2, "A" indicates that the marker was derived from Koshihikari, and "B" indicates that the marker was derived from Habataki.

TABLE 2

| Chromosome 2 | Marker | (cN) | KHSL01 BC5F4 | KHSL02 EC4F4 | KHSL03 BC4F4 | KHSL04 BC4F4 | KHSL05 BC4F4 | KHSL06 BC4F4 | KHSL07 BC4F4 |
|---|---|---|---|---|---|---|---|---|---|
| Chromosome 2 | RM2770 | 4.7 | A | A | A | B | A | A | A |
| | RM7562 | 8.9 | A | A | A | B | A | A | A |
| | RM4355 | 19 | A | A | A | B | A | A | A |
| | RM6378 | 28 | A | A | A | B | A | A | A |
| | RM6853 | 42.1 | A | A | A | B | A | A | A |
| | RM1313 | 51.1 | A | A | A | B | A | A | A |
| | RM4499 | 62.2 | A | A | A | B | B | A | A |
| | RM6023 | 81.7 | A | A | A | B | B | A | A |
| | RM3874 | 94.3 | A | A | A | A | B | A | A |
| | RM1920 | 103.4 | A | A | A | A | B | A | A |
| | RM3512 | 112.6 | A | A | A | A | B | A | A |
| | RM6933 | 123.9 | A | A | A | A | B | A | A |
| | RM3316 | 180.2 | A | A | A | A | B | A | A |
| | RM5916 | 146.9 | A | A | A | A | B | A | A |
| | RM2265 | 157.9 | A | A | A | A | B | A | A |

Further, the QTL analysis was performed as described above on Tachisugata//Tachisugata/Momiroman BC1F4 using the BBC resistant rice cultivar "Tachisugata" and the susceptible rice cultivar "Momiroman". As a result, it was revealed that the gene locus for determining the BBC resistance was located on a short arm of chromosome 2 of Tachisugata as in the above case. It was demonstrated that the gene loci specified by the QTL analyses using different rice cultivars were located on the same region, and that 11 candidate genes existed according to the rice cultivar "Nipponbare" database information (see Table 3).

TABLE 3

| Length (bp) | Function |
|---|---|
| 6359 | Similar to NBS-LRR protein (Fragment) |
| 3899 | Leucine-rich repeat, cysteine-containing subtype containing protein |
| 8999 | Protein phosphatase 2C family protein |
| 3991 | Similar to Iron/ascorbate-dependent oxidoreductase |
| 741 | Similar to Glyoxalase I |
| 9866 | Similar to Dual specificity kinase 1 |
| 1558 | Similar to Xyloglucan endotransglycosylase (Fragment) |
| 1510 | Similar to Xet3 protein |
| 1688 | Micro-fibrillar-associated 1, C-terminal family protein |
| 655 | Non-protein coding transcript, unclassifiable transcript. |
| 3856 | Conserved hypothetical protein |

Moreover, it was also revealed that both the base sequences of the 11 candidate genes and hypothetical amino acid sequences did not have a homology with enzymes and genes thereof in the tyrosine metabolic pathway and the carotenoid biosynthetic pathway, which were influenced by BBC (see FIG. 1).

Figure 8:
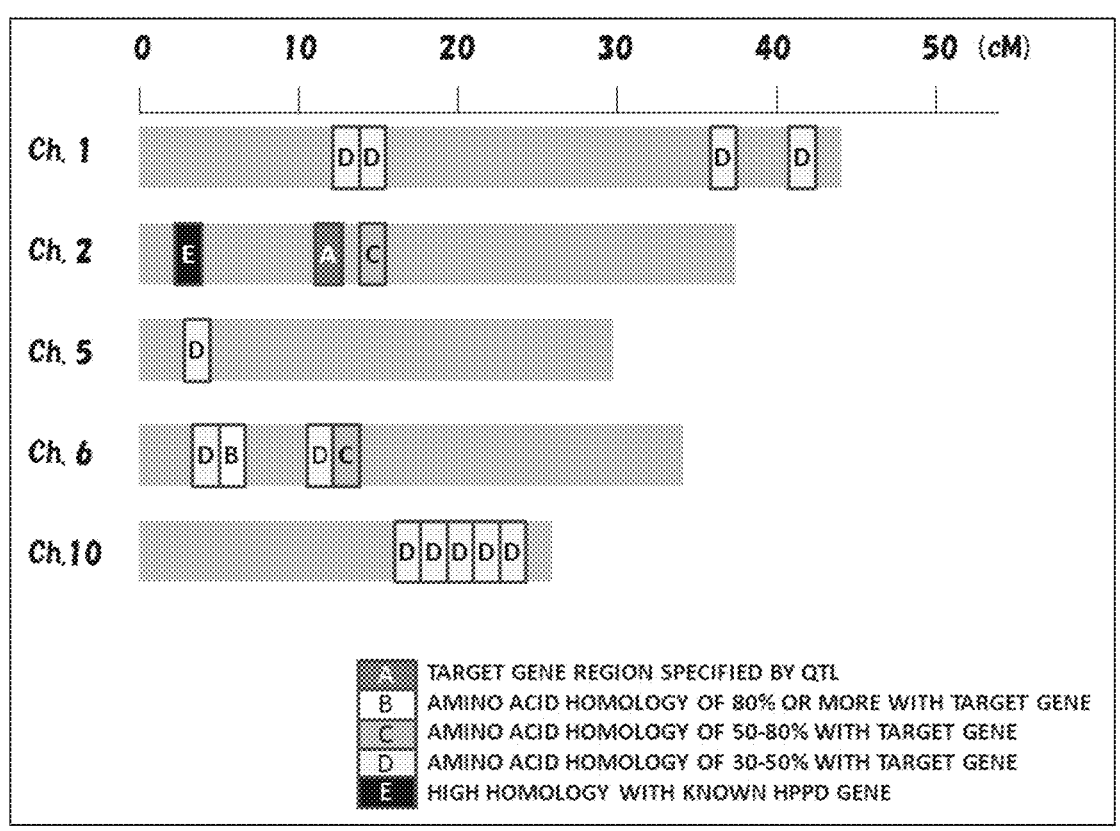
FIG. 8 is a representation showing the 4-HPPD inhibitor-resistance gene (AK065581) specified by a QTL analysis and homologous genes thereof, which are located on rice chromosomes.

Incidentally, according to the rice cultivar "Nipponbare" database information, a rice gene having the highest homology with the known gene encoding an HPPD enzyme whose activity is inhibited by BBC is located on the short arm of chromosome 2, but a gene locus thereof was different from that specified by the QTL analysis (see FIG. 8).

Furthermore, in order to narrow down the region where a gene associated with the BBC resistance was located, an F2 population was produced by crossing KHSL04 with Koshihikari, and a population for analysis of the short arm of chromosome 2 was produced from the BC1F4 lines obtained by one-time backcrossing of Tachisugata to Momiroman. The analysis was attempted again using the two populations. As a result, it was revealed that the gene associated with the BBC resistance existed between the SSR markers RM12980 and RM12983. Moreover, genes existing in the region thus narrowed down were searched for by RAP-DB. The result demonstrated the existence of 10 candidate genes excluding a protein similar to glyoxalase I (741 bp).

Example 2

Identification of 4-HPPD Inhibitor-Resistance Gene

As described above, the QTL analysis suggested that the gene for determining resistance to a 4-HPPD inhibitor be located on the short arm of chromosome 2 of rice. Accordingly, focusing on the hypothetical gene of the iron/ascorbate-dependent oxidoreductase gene located on the gene locus, the Tos17-inserted lines were tested to reveal a linkage between phenotype (high BBC susceptibility) and genotype, and also recombinants of BBC susceptible *A. thaliana* and rice having the gene introduced therein were produced to examine an effect of providing the BBC resistance.

Specifically, at the gene locus for determining the BBC resistance specified by the QTL analysis, the hypothetical gene of iron/ascorbate-dependent oxidoreductase (hereinafter also referred to as "target gene") is located, similarly to the HPPD enzyme whose activity is inhibited by BBC (see Table 4).

TABLE 4

| Gene | Os02g0280700 |
|---|---|
| mRNA | AK065581 |
| Position | chr02: 10415297 ... 10419287 (+strand) |
| Length | 3991 bp |
| Description | Similar to iron/ascorbate-dependent oxidoreductase (Os02t0280700-01) |
| transcript_mutant | Os02t0280700-01 |

Although the original cultivar "Nipponbare" of the Tos17-inserted lines is a BBC resistant cultivar, BBC susceptible individuals are derived from the lines having Tos17 inserted in the transcription site of the target gene. The phenotype (BBC susceptibility) and the genotype (Tos17-inserted homozygote) were examined by the linkage analysis tested on 30 individuals in total. As a result, all the progenies of six Tos17-inserted homozygous individuals showed BBC susceptibility. Meanwhile, all the progenies of 18 Tos17-inserted heterozygous individuals were segregated into BBC susceptible individuals. These results suggested that the hypothetical gene of the iron/ascorbate oxidoreductase gene be closely associated with the BBC resistance.

Figure 9:
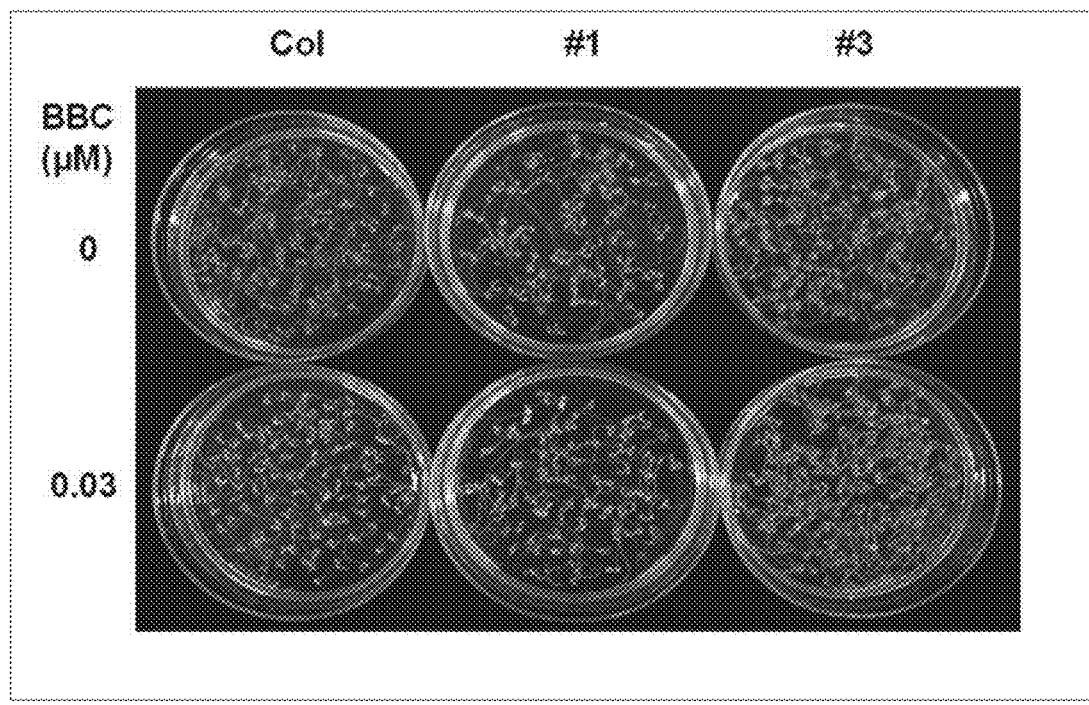
FIG. 9 shows a photograph for illustrating resistance of recombinant *A. thaliana* (ecotype Columbia) to a 4-HPPD inhibitor (benzobicyclon (BBC)), the recombinant *A. thaliana* having the target gene (AK065581) introduced therein. Note that, in the figure, "Col" shows the result of *A. thaliana* wildtype (ecotype Columbia), "#1" and "#3" show the results of recombinant *A. thaliana* (ecotype Columbia) having the target gene (AK065581) introduced therein.

Accordingly, in order to verify that the target gene was a BBC resistance gene, recombinants (T2 generation) were prepared by introducing the target gene into *A. thaliana* (ecotype Columbia) that would be whitened by an agar medium containing 0.03 µM BBC, and the growth state of the recombinants was examined in the presence of BBC at this concentration. FIG. 9 shows the obtained result.

Figure 10:
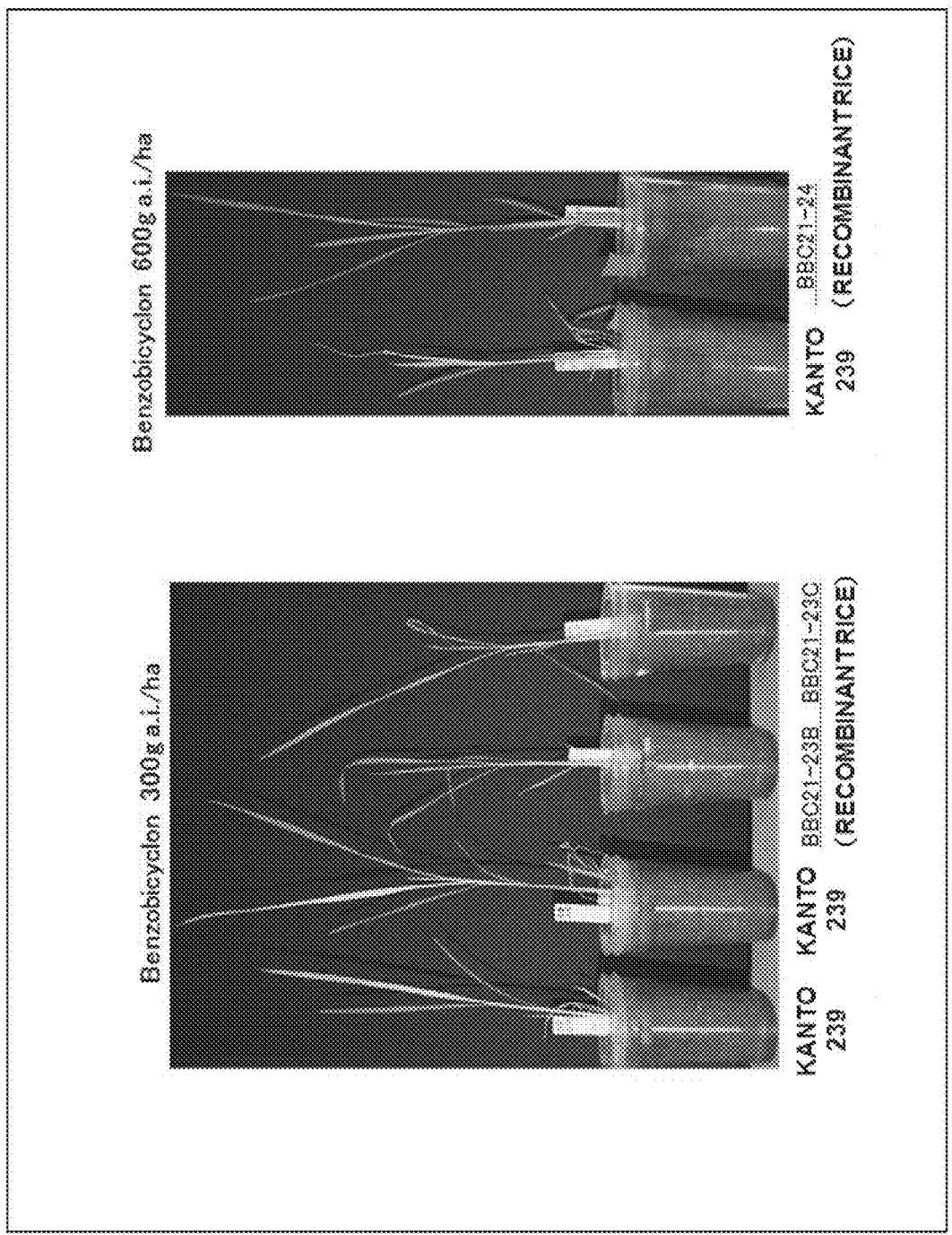
FIG. 10 shows photographs for illustrating resistance of recombinant rice (4-HPPD inhibitor-susceptible cultivar: Kanto 239) to a 4-HPPD inhibitor (benzobicyclon), the recombinant rice havingthe target gene (AK065581) introduced therein. Note that, in the figure, "Kanto 239" shows the result of Kanto 239 (wildtype), and "BBC21-23B" and "BBC21-23C" show the results of Kanto 239(recombinant rice) having the target gene (AK065581) introduced therein.

Further, recombinants (T0 generation) were prepared by introducing the target gene into the BBC susceptible rice cultivar "Kanto 239" that would be whitened by an agar medium containing 0.1 µM BBC, and the growth state of the recombinants was examined in composted soil treated with BBC at 300 ga.i./ha. FIG. 10 shows the obtained result.

Figure 11:
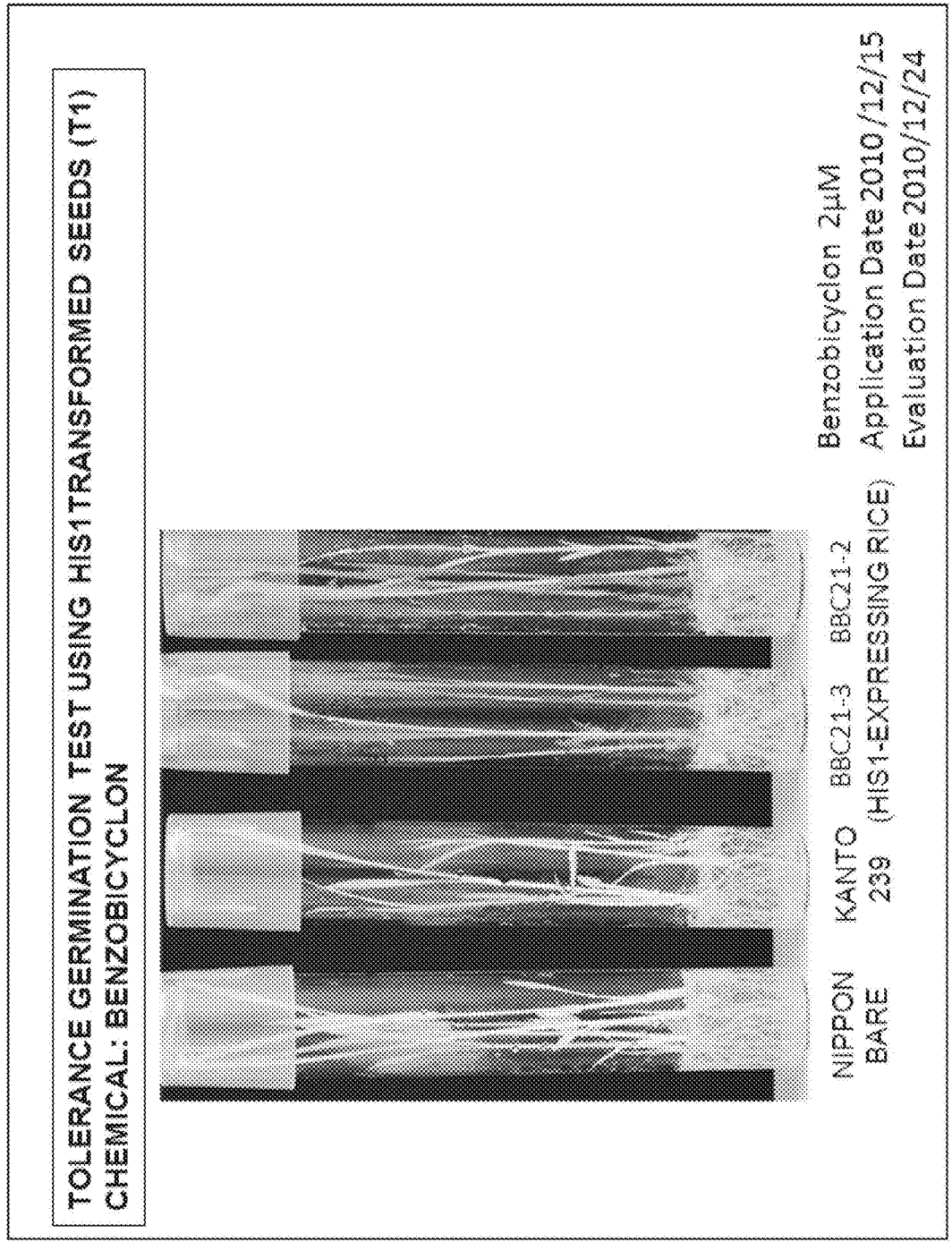
FIG. 11 shows a photograph for illustrating resistance of recombinant rice (Kanto 239) to a 4-HPPD inhibitor (benzobicyclon), the recombinant rice havingthe target gene (AK065581) introduced therein. Note that, in the figure, "Nipponbare" and "Kanto 239" respectively show the results of Nipponbare (wildtype) (4-HPPD inhibitor-resistant cultivar) and Kanto 239 (wildtype), and "BBC21-1A, 2, 3, 3D, 3F, 3-3, 9, 15" show the results of Kanto 239 (recombinant rice) having the target gene (AK065581) introduced therein (the same applies to FIGS. 12 to 15). In addition, "Application Date" and "Evaluation Date" respectively indicate "date when the seeds were seeded on a solid (agar)medium supplemented with a 4-HPPD inhibitor" and "date when the growth state of the plants grown from the seeds was examined" (the same applies to FIGS. 12 to 15 and 22).
Figure 12:
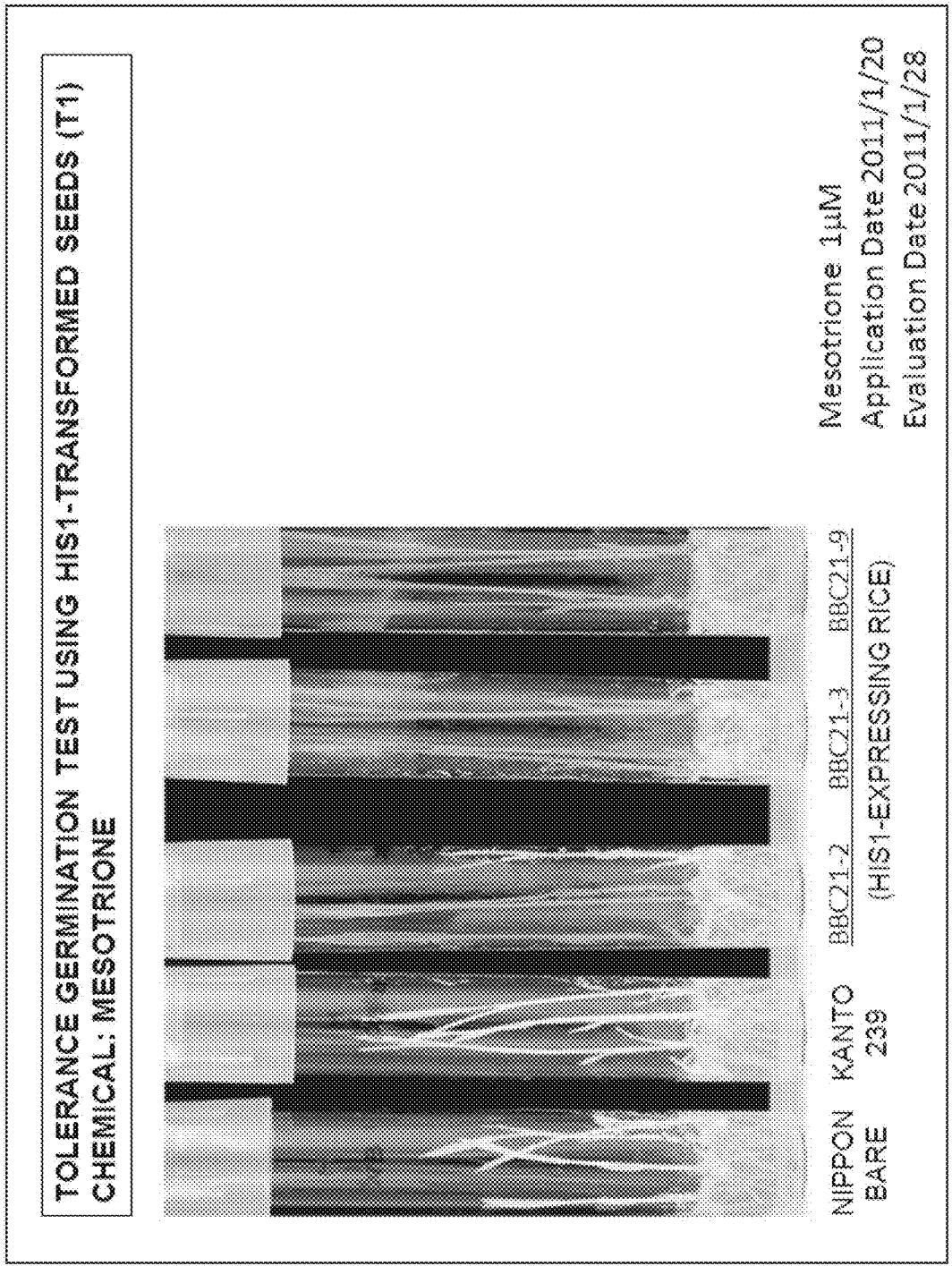
FIG. 12 shows a photograph for illustrating resistance of recombinant rice (Kanto 239) to a 4-HPPD inhibitor (mesotrione), the recombinant rice having the target gene (AK065581) introduced therein.
Figure 13:
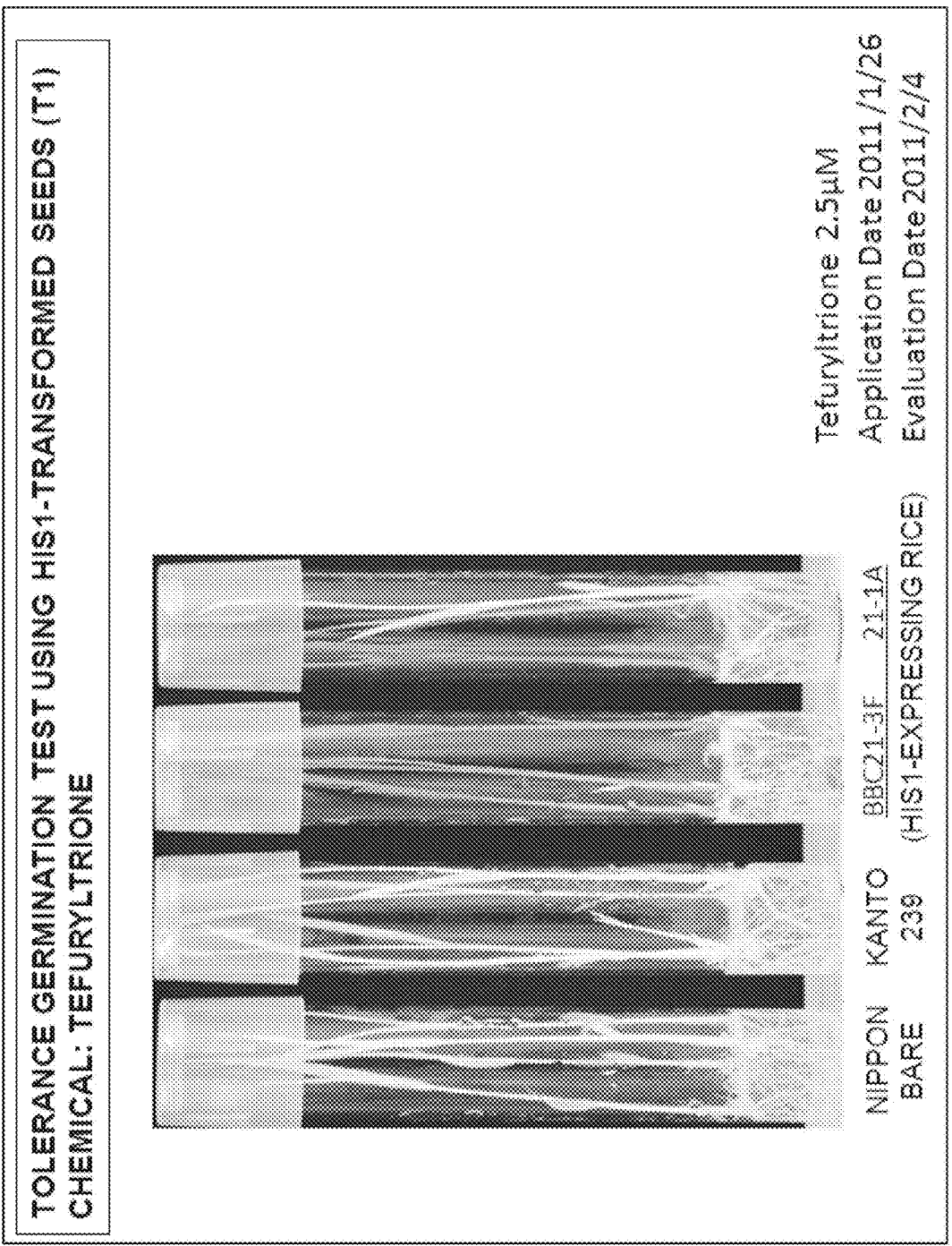
FIG. 13 shows photographs for illustrating resistance of recombinant rice (Kanto 239) to a 4-HPPD inhibitor (tefuryltrione), the recombinant rice havingthe target gene (AK065581) introduced therein.
Figure 14:
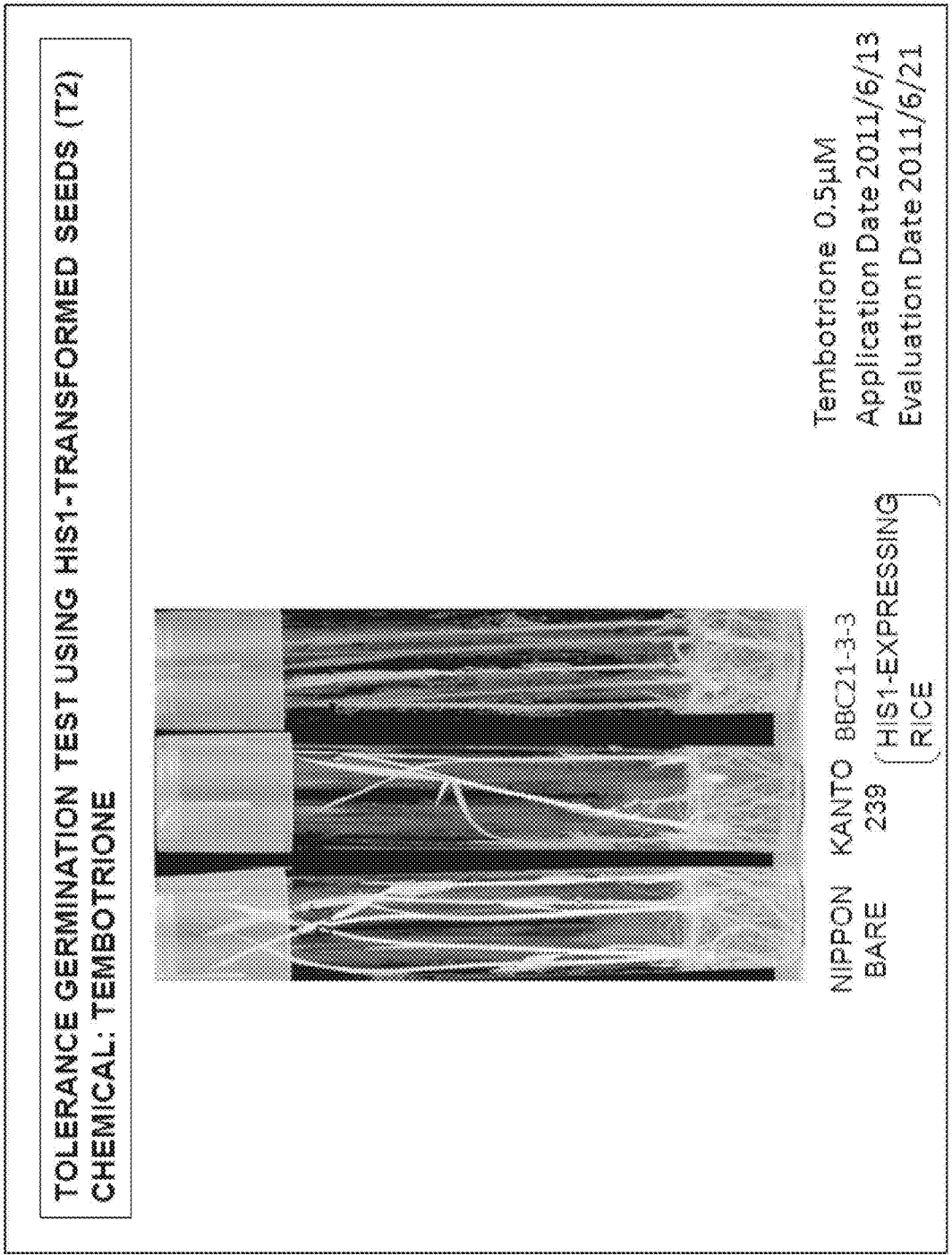
FIG. 14 shows a photograph for illustrating resistance of recombinant rice (Kanto 239) to a 4-HPPD inhibitor (tembotrione), the recombinant rice having the target gene (AK065581) introduced therein.
Figure 15:
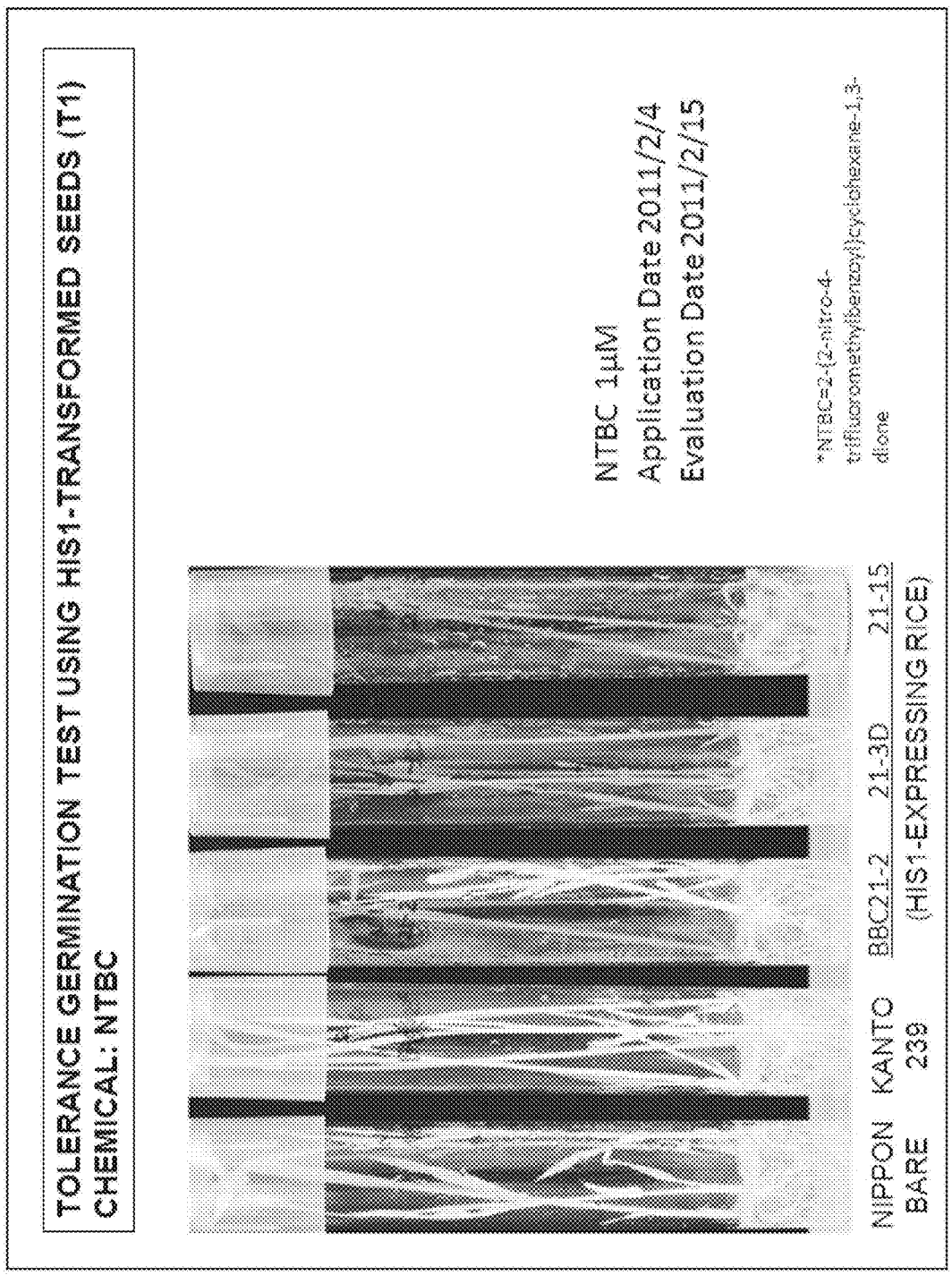
FIG. 15 shows a photograph for illustrating resistance of recombinant rice (Kanto 239) to a 4-HPPD inhibitor (NTBC), the recombinant rice having the target gene (AK065581) introduced therein.

Furthermore, recombinants were prepared by introducing the target gene into the BBC susceptible rice cultivar "Kanto 239" that would be whitened by an agar medium containing 0.1 µM BBC, and T1 seeds or T2 seeds were obtained. These were seeded on an agar medium containing 2 µM BBC, and the growth state of the recombinants was examined. FIG. 11 shows the obtained result. Moreover, the seeds were seeded on an agar medium containing 1 µM mesotrione, 2.5 µM tefuryltrione, 0.5 µM tembotrione, or 1 µM NTBC, and the growth state of the recombinants was examined. FIGS. 12 to 15 show the obtained results.

As apparent from the result shown in FIG. 9, the *A. thaliana* recombinants having the target gene introduced therein grew without being whitened by the agar medium containing 0.03 µM BBC. Moreover, as apparent from the result shown in FIG. 10, the rice recombinants having the target gene introduced therein grew without being whitened by the composted soil treated with BBC at 300 ga.i./ha. Further, as apparent from the result shown in FIG. 11, the rice recombinants having the target gene introduced therein grew without being whitened by the agar medium treated with 2 µM BBC. It should be noted that this concentration is a high concentration sufficient to whiten the BBC resistant cultivar Nipponbare.

Furthermore, as apparent from the results shown in FIGS. 12 to 15, the rice recombinants having the target gene introduced therein grew without being whitened also in the medium containing the triketone type 4-HPPD inhibitor (mesotrione, tefuryltrione, tembotrione or NTBC) other than BBC. Specifically, the rice recombinants having the target gene introduced therein grew without being whitened by the agar medium treated with 1 µM mesotrione, 2.5 µM tefuryltrione, 0.5 µM tembotrione, or 1 µM NTBC.

These results verified that the target gene was a 4-HPPD inhibitor-resistance gene (HIS1 gene), that is, a DNA encoding a protein having an activity of providing a plant with resistance to a 4-HPPD inhibitor.

Example 3

Determination of Resistance or Susceptibility to 4-HPPD Inhibitor by Analyzing Base Sequence of HIS1 Gene Although the HIS1 gene on chromosome 2 of *japonica* type rice was specified, the amplification product of the HIS1 gene, amplified by PCR, was also obtained from BBC susceptible rice cultivars. In addition, among the BBC susceptible rice cultivars, it is sometimes difficult to determine whether Kasalath has susceptibility or resistance, depending on the BBC-treatment condition. For this reason, whether or not it was possible to determine a relation between the base sequence of the HIS1 gene and the degree of BBC susceptibility was examined by PCR by which a particular region of the HIS1 gene was amplified.

It should be noted that although unillustrated, all of Momiroman, Takanari, and Kasalath are BBC susceptible cultivars at different levels; it has been confirmed that Momiroman and Takanari show high BBC susceptibility in comparison with the BBC susceptibility of Kasalath.

Figure 16:
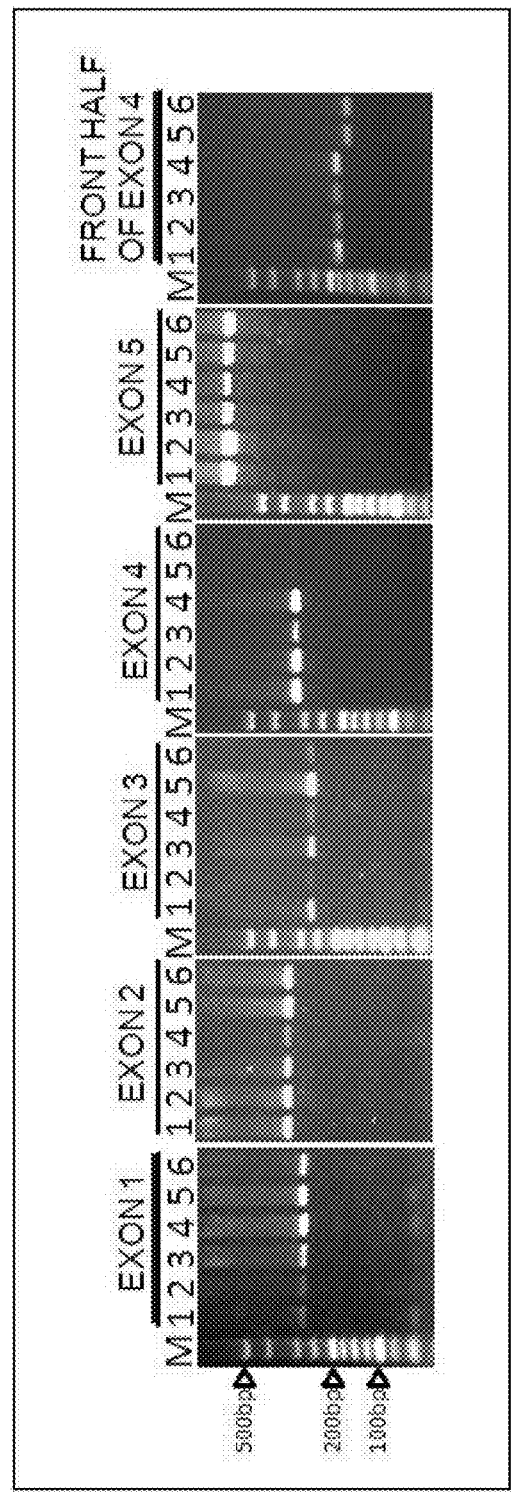
FIG. 16 shows electrophoresis images for illustrating PCR patterns of amplified exon regions of the HIS1 gene of rice cultivars. Note that, in the figure, "1" shows the result of Nipponbare, "2" shows the result of Koshihikari, "3" shows the result of Kasalath, "4" shows the result of Hokuriku 193, "5" shows the result of Takanari, "6" shows the result of Momiroman, and "M" indicates a size marker. Moreover, "exon 1" indicates the region of exon 1 of the HIS1 gene, which was amplified by PCR using a primer having a base sequence of SEQ ID NO: 3 and a primer having a base sequence of SEQ ID NO: 4, "exon 2" indicates the region of exon 2 of the HIS1 gene, which was amplified by PCR using a primer having a base sequence of SEQ ID NO: 5 and a primer having a base sequence of SEQ ID NO: 6, "exon 3" indicates the region of exon 3 of the HIS1 gene, which was amplified PCR using a primer having a base sequence of SEQ ID NO: 7 and a primer having a base sequence of SEQ ID NO: 8, "exon 4" indicates the region exon 4 of the HIS1 gene, which was amplified by PCR using a primer having a base sequence of SEQ ID NO: 9 and a primer having a base sequence of SEQ ID NO: 10, and "exon 5" indicates the region of exon 5 of the HIS1 gene, which was amplified by PCR using a primer having a base sequence of SEQ ID NO: 11 and a primer having a base sequence of SEQ ID NO: 12. Further, "front half of exon 4" indicates a front half region inside exon 4 of the HIS1 gene, which was amplified by PCR using a primer having a base sequence of SEQ ID NO: 13 and a primer having a base sequence of SEQ ID NO: 14. Furthermore, in the figure, the arrow heads indicate sizes of 100 pb, 200 bp, and 500 bp.

Hence, first, BBC susceptible cultivars (Momiroman, Takanari, Kasalath) and BBC resistant cultivars (Nipponbare, Koshihikari, Hokuriku 193) were analyzed by PCR using the primers specifically amplifying the five exon regions of the HIS1 gene. FIG. 16 shows the obtained result.

As apparent from the result shown in FIG. 16, the analysis result of PCR using the primer specifically amplifying a front half portion of the fourth exon of the HIS1 gene revealed that the molecular weights of PCR products of the BBC highly-susceptible cultivars Momiroman and Takanari were low in comparison with those of the BBC resistant cultivars.

Figure 17:
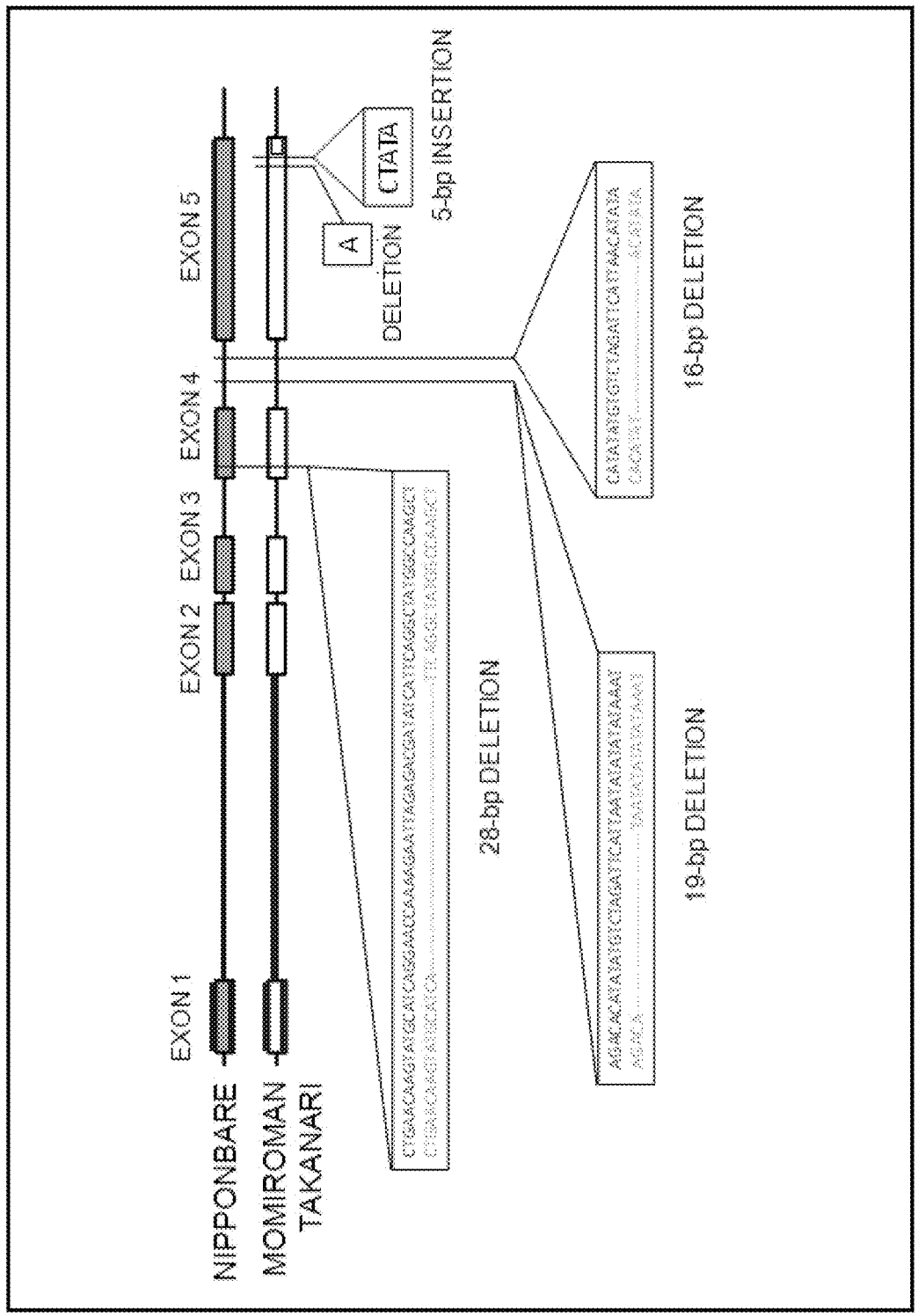
FIG. 17 is a schematic representation for illustrating the result of comparing the structure of the HIS1 gene of Nipponbare with those of the corresponding genes of Momiroman and Takanari.

Further, the genomic DNA sequences of the BBC susceptible cultivars Momiroman and Takanari were compared with that of the BBC resistant cultivar Nipponbare. FIG. 17 shows the obtained result.

As apparent from the result shown in FIG. 17, in agreement with the above-described PCR analysis result, it was found out that Momiroman and Takanari had a 28-bp deletion in the front half portion of the fourth exon of the HIS1 gene. Further, it was revealed that an intron between the fourth exon and the fifth exon of the HIS1 gene also had 19-bp and 16-bp deletion sites. Moreover, it was also observed that the fifth exon of the HIS1 gene had a 1-bp (adenine) deletion and a 5-bp insertion.

Figure 18:
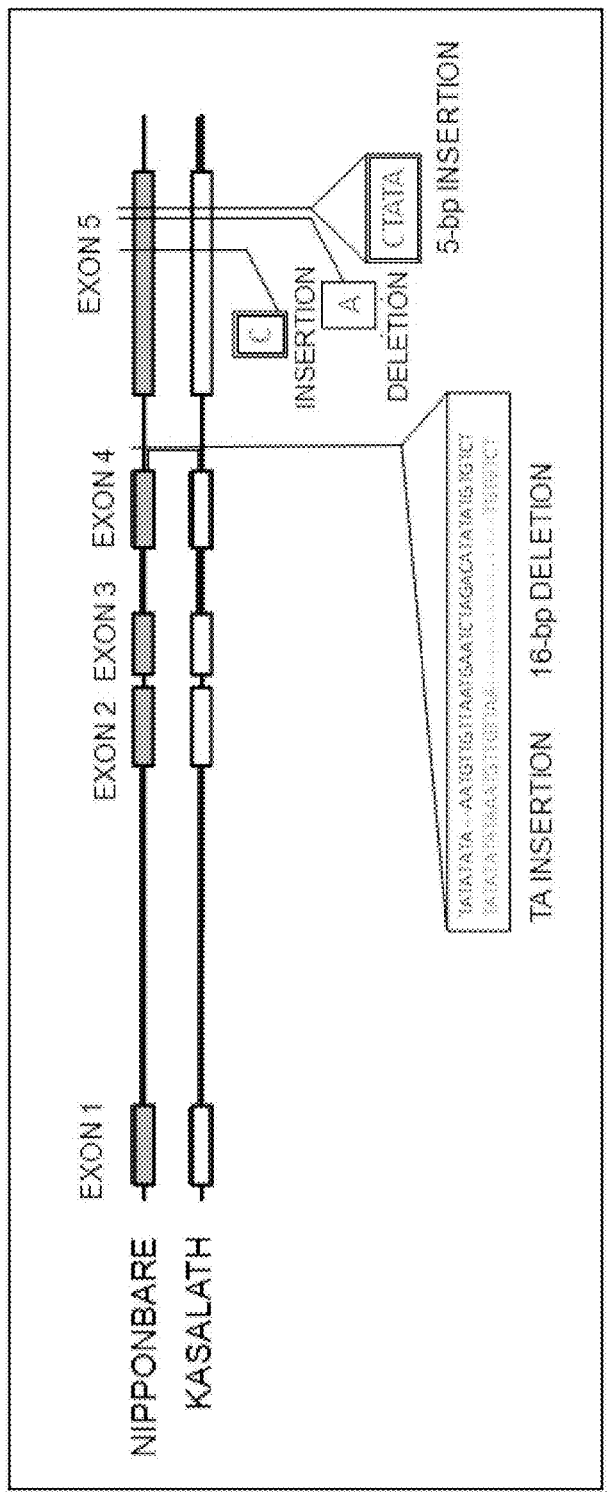
FIG. 18 is a schematic representation for illustrating the result of comparing the structure of the HIS1 gene of Nipponbare with that of the corresponding gene of Kasalath.

Furthermore, the genomic DNA sequence of the BBC susceptible cultivar Kasalath was compared with that of the BBC resistant cultivar Nipponbare. FIG. 18 shows the obtained result.

As apparent from the result shown in FIG. 18, in agreement with the above-described PCR analysis result, no deletion in the front half portion of the fourth exon of the HIS1 gene was observed in Kasalath. Nevertheless, it was revealed that an intron between the fourth exon and the fifth exon of the HIS1 gene had a TA insertion and a 16-b.p. deletion site. Moreover, it was also observed that the fifth exon of the HIS1 gene had an adenine deletion, a 5-bp insertion, and a cytosine insertion.

Thus, these results revealed that an activity that a protein encoded by the HIS1 gene had so as to provide a plant with resistance to a 4-HPPD inhibitor was suppressed by the base deletion and/or insertion from the fourth exon to the fifth exon of the HIS1 gene. In addition, it seems that the difference of Momiroman and Takanari from Kasalath in susceptibility to a 4-HPPD inhibitor is attributable to whether or not a deletion is present in the front half portion of the fourth exon of the HIS1 gene, and so forth.

Example 4

Analysis of Gene Having Homology with HIS1 Gene

Next, a database was searched for a gene having a homology with the HIS1 gene. Specifically, using NCBI Blast, a tBLASTN search (default setting) was conducted using the amino acid sequence of the protein encoded by the HIS-1 gene as a query. Note that the data to be searched was nr/nt (non-redundant nucleotide collection).

As a result, it was revealed that the rice gene (HSL1 gene) having the highest homology with the HIS1 gene was located on chromosome 6, and that the homology of the hypothetical amino acid sequences was as high as approximately 86% (see FIG. 19). Moreover, it was also revealed that the homologous genes on chromosome 6 formed a gene cluster nearby.

Nonetheless, it is presumed that proteins encoded by these homologous genes on chromosome 6 are also expressed in a susceptible cultivar having the HIS1 gene mutated.

Figure 20:
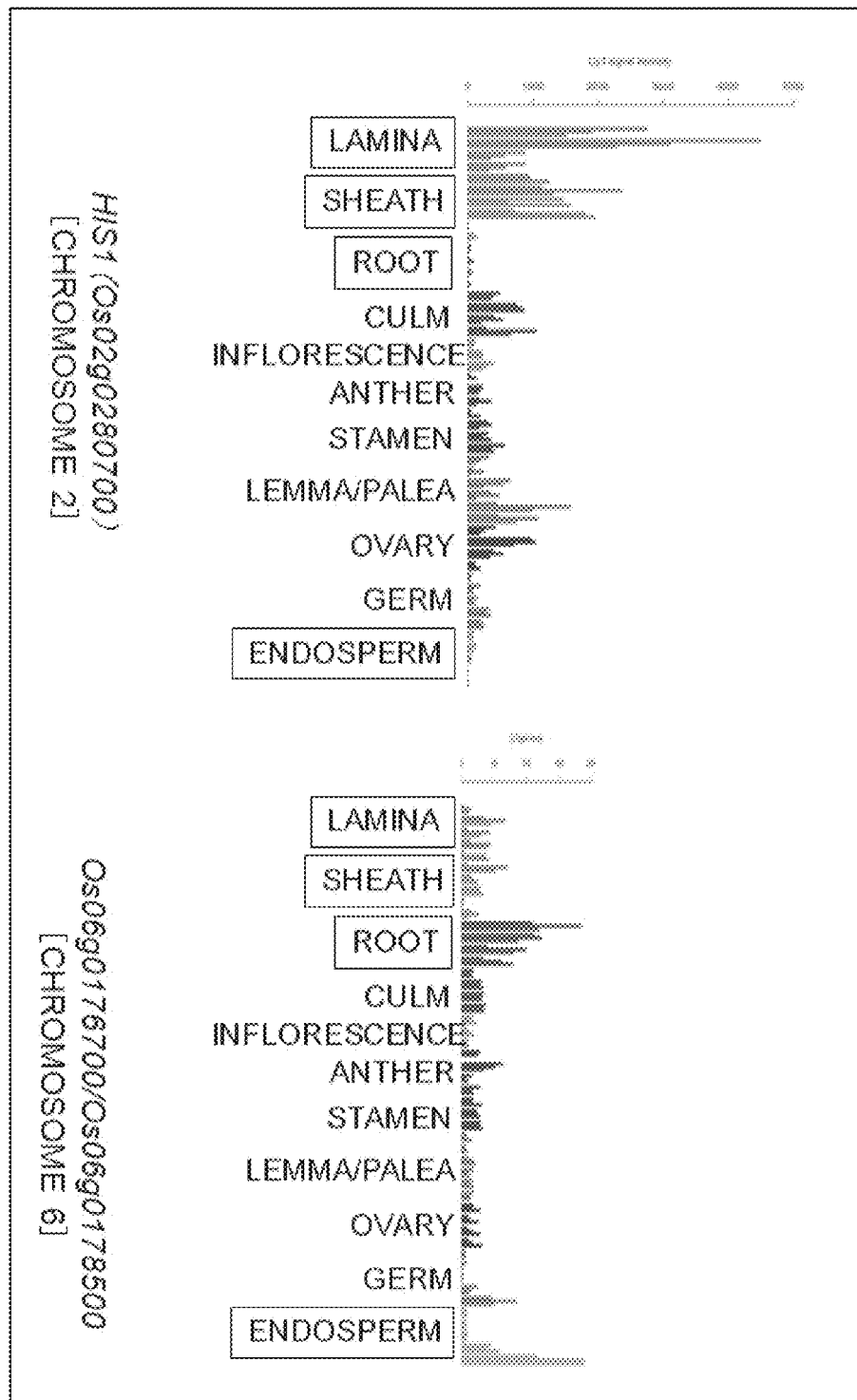
FIG. 20 shows graphs for illustrating expression patterns, in tissues, of a gene locus (chromosome 2) where the HIS1 gene is located and a gene locus (chromosome 6) where the homologous gene (HSL1 gene: Os06g0176700/ 0s06g0178500) is located.

Regarding this point, as shown in FIG. 20, the HIS1 gene is mainly expressed in leaves, while the homologous genes on chromosome 6 are mainly expressed in roots and maturing seeds. For this reason, it is thought that although the proteins encoded by the homologous genes on chromosome 6 potentially have an activity of providing a plant with resistance to a 4-HPPD inhibitor, the effect may not be exhibited because the expression level in leaves is low.

Incidentally, FIG. 20 is based on the result of analyzing expression patterns of HIS1 (Os02g0280700) and the homologous genes (Os06g0176700/Os06g0178500) on chromosome 6 in different tissues and growth periods using RiceXPro (rice gene expression database /http://ricexpro.dna.affrc.go.jp/) (see Sato et al., Nucleic Acids Res. Nov. 2, 2010 [Epub ahead of print]).

Figure 21:
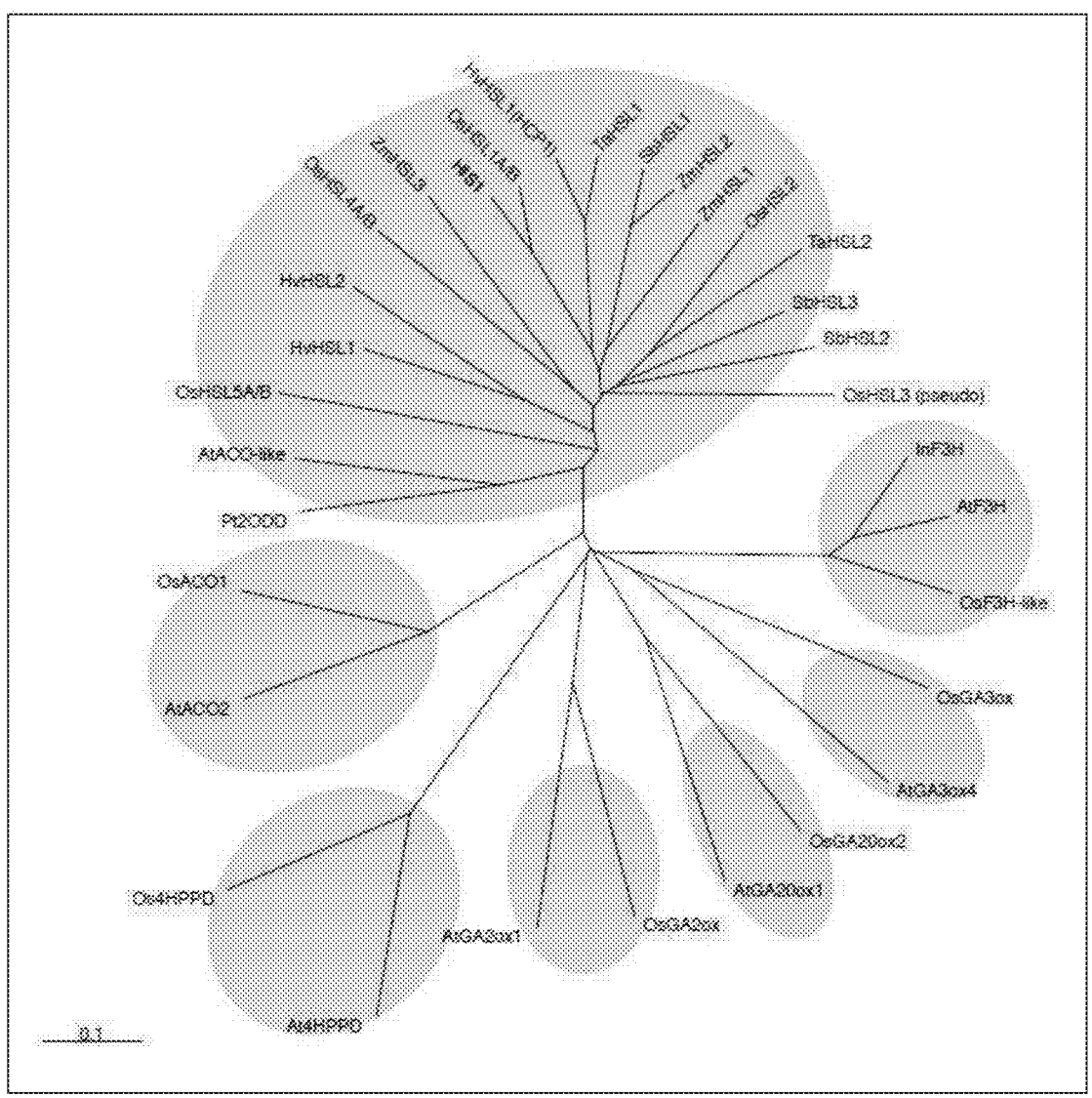
FIG. 21 is a phylogenetic tree for illustrating that the HIS1 gene and the homologous gene belong to genes specific to Poaceae (monocot) plants. Note that, in the figure, "HSL" is an abbreviation for "HIS1-LIKE," indicating a homologous gene of HIS1.

Moreover, it was revealed that the homologous genes of the HIS1 gene were scattered only among monocots, and were not found among dicots (see FIG. 21). Furthermore, genes having a slightly low homology with the HIS1 gene including ethylene synthesizing ACC oxidase genes are thoroughly distributed among plants, but the functions are thought to be different. Incidentally, FIG. 21 is obtained by extracting amino acid sequences of proteins having a homology with HIS1 by the tBLASTN analysis, performing a phylogenetic tree analysis on the basis of the obtained sequences using ClustalW software, and drawing the result with TreeView software.

Example 5

Analysis of HSL1 Gene

The rice gene (HSL1 gene) having the highest homology with the HIS1 gene and located on chromosome 6 was examined whether or not the HSL1 gene was a DNA encoding a protein having an activity of providing a plant with resistance to a 4-HPPD inhibitor.

Figure 22:
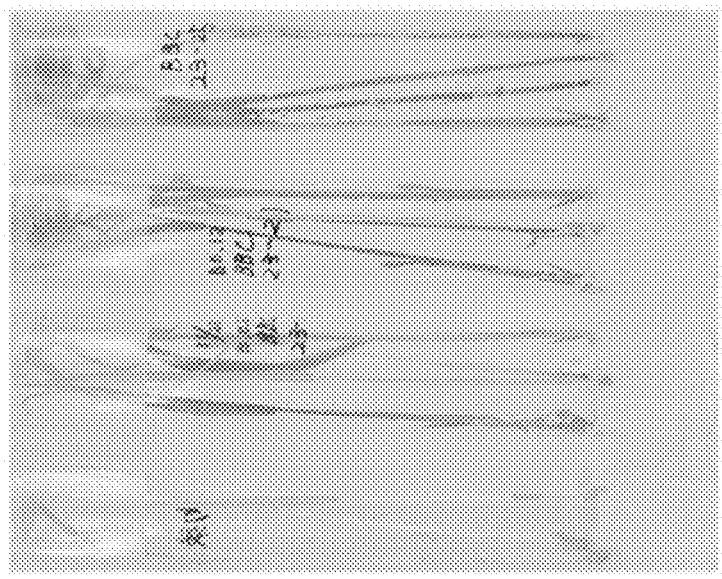
FIG. 22 shows a photograph for illustrating resistance of recombinant rice (Kanto 239), in which the gene (HSL1; AK241948) having a high homology with the HIS1 gene was introduced, to the 4-HPPD inhibitor (benzobicyclon). Note that, in the figure, "Kanto 239" shows the result of Kanto 239 (wildtype), and "23-1", "23-21", and "23-25" show the results of Kanto 239(recombinant rice) having the homologous gene (AK241948) introduced therein.

Specifically, recombinants were prepared by introducing the target gene into the BBC susceptible rice cultivar "Kanto 239" that would be whitened by an agar medium containing 0.1 μM BBC, and T1 seeds or T2 seeds were obtained. These were seeded on an agar medium containing 0.12 μM BBC, and the growth state of the recombinants was examined. FIG. 22 shows the obtained result.

As apparent from the result shown in FIG. 22, the rice recombinants having the homologous gene introduced therein grew without being whitened by the agar medium containing 0.12 μM BBC. This concentration is a concentration at which the BBC resistant cultivar "Nipponbare" is not whitened. This result verified that although the tolerance level was low, the HSL1 gene was a DNA encoding a protein having an activity of providing a plant with resistance to a 4-HPPD inhibitor, similarly to the HIS1 gene.

Industrial Applicability

When plants having increased resistance to a 4-HPPD inhibitor of the present invention are used and cultivated, the weed control can be efficiently carried out in cultivation paddy fields or cultivation fields. In addition, a method for determining whether a plant has resistance or susceptibility to a 4-HPPD inhibitor of the present invention can be utilized, for example, to reduce a germination risk of self-sown seeds from the previous year in crop rotation cycles. In this manner, the present invention can contribute greatly to stable production and yield increase of useful plants.

[Sequence Listing Free Text]
SEQ ID NOs: 3 to 14
<223> sequences of artificially synthesized primers

The invention claimed is:

1. An agent for providing a plant with resistance to a 4-HPPD inhibitor, the agent comprising a DNA selected from the following (a) to (b):
  (a) a DNA comprising a nucleotide sequence which encodes a protein comprising the amino acid sequence of SEQ ID NO: 2 or 17, and wherein said DNA further comprises a heterologous nucleotide sequence; and
  (b) a DNA comprising a nucleotide sequence which encodes an amino acid sequence having at least 90% sequence identity to the amino acid sequence of SEQ ID NO: 17 and contains at least 10 substitutions relative to the amino acid sequence of SEQ ID NO: 17.

2. A transgenic plant cell capable of regenerating a plant having increased resistance to a 4-HPPD inhibitor, the transgenic plant cell comprising a DNA selected from the following (a) to (b):
  (a) a DNA comprising a nucleotide sequence which encodes a protein comprising the amino acid sequence of SEQ ID NO: 2 or 17; and
  (b) a DNA comprising a nucleotide sequence which encodes a protein having an amino acid sequence having at least 90% sequence identity to the amino acid sequence of SEQ ID NO: 2 or 17.

3. A plant having increased resistance to a 4-HPPD inhibitor, wherein said plant is regenerated from the transgenic plant cell of claim 2, and wherein said plant comprises said DNA.

4. A plant having increased resistance to a 4-HPPD inhibitor, which is a progeny or a clone of the plant of claim 3, and wherein said progeny or clone comprises said DNA.

5. A propagation material of the plant of claim 3 and wherein said propagation material comprises said DNA.

6. A method for producing a plant having increased resistance to a 4-HPPD inhibitor, the method comprising:
(I) introducing, into a plant cell, a DNA selected from the following (a) to (b),
   (a) a DNA comprising a nucleotide sequence which encodes a protein comprising the amino acid sequence of SEQ ID NO: 2 or 17, and
   (b) a DNA comprising a nucleotide sequence which encodes a protein having an amino acid sequence having at least 90% sequence identity to the amino acid sequence of SEQ ID NO: 2 or 1; and
(II) regenerating a plant from the transgenic plant cell, wherein said plant comprises said DNA.

7. An agent for providing a plant with susceptibility to a 4-HPPD inhibitor, the agent comprising a DNA selected from the following (a) and (b):
   (a) a DNA encoding a double-stranded RNA complementary to a transcript of a DNA selected from the following (d) to (e); and
   (b) a DNA encoding an RNA having a ribozyme activity of specifically cleaving a transcript of a DNA selected from the following (d) to (e),
   (d) a DNA comprising a nucleotide sequence which encodes a protein comprising the amino acid sequence of SEQ ID NO: 2 or 17; and
   (e) a DNA comprising a nucleotide sequence which encodes a protein having an amino acid sequence having at least 90% sequence identity to the amino acid sequence of SEQ ID NO: 2 or 17.

8. A transgenic plant cell capable of regenerating a plant having increased susceptibility to a 4-HPPD inhibitor, the transgenic plant cell comprising a DNA selected from the following (a) and (b):
   (a) a DNA encoding a double-stranded RNA complementary to a transcript of a DNA selected from the following (d) to (e); and
   (b) a DNA encoding an RNA having a ribozyme activity of specifically cleaving a transcript of a DNA selected from the following (d) to (e),
   (d) a DNA comprising a nucleotide sequence which encodes a protein comprising the amino acid sequence of SEQ ID NO: 2 or 17; and
   (e) a DNA comprising a nucleotide sequence which encodes a protein having an amino acid sequence having at least 90% sequence identity to the amino acid sequence of SEQ ID NO: 2 or 17.

9. A plant having increased susceptibility to a 4-HPPD inhibitor, wherein said plant is regenerated from the transgenic plant cell of claim 8, and wherein said plant comprises said DNA selected from the (a) and (b).

10. A plant having increased susceptibility to a 4-HPPD inhibitor, which is a progeny or a clone of the plant of claim 9, and wherein said progeny or clone comprises said DNA selected from the (a) and (b).

11. A propagation material of the plant of claim 9, having increased susceptibility to a 4-HPPD inhibitor, and wherein said propagation material comprises said DNA selected from the (a) and (b).

12. A method for producing a plant having increased susceptibility to a 4-HPPD inhibitor, the method comprising:
(I) introducing, into a plant cell, a DNA selected from the following (a) and (b),
   (a) a DNA encoding a double-stranded RNA complementary to a transcript of a DNA selected from the following (d) to (e), and
   (b) a DNA encoding an RNA having a ribozyme activity of specifically cleaving a transcript of a DNA selected from the following (d) to (e),
   (d) a DNA comprising a nucleotide sequence which encodes a protein comprising the amino acid sequence of SEQ ID NO: 2 or 17, and
   (e) a DNA comprising a nucleotide sequence which encodes a protein having an amino acid sequence having at least 90% sequence identity to the amino acid sequence of SEQ ID NO: 2 or 17; and
(II) regenerating a plant from the transgenic plant cell, wherein said plant comprises said DNA selected from the (a) and (b).

13. A method for selecting a plant with resistance or susceptibility to a 4-HPPD inhibitor, wherein the method comprises:
(I) analyzing a test plant to determine the presence or absence of a DNA sequence selected from the following (a) to (b), or to determine the nucleotide sequence of an expression control region of said DNA,
   (a) a DNA comprising a nucleotide sequence which encodes a protein comprising the amino acid sequence of SEQ ID NO: 2 or 17, and
   (b) a DNA comprising a nucleotide sequence which encodes a protein having an amino acid sequence having at least 90% sequence identity to the amino acid sequence of SEQ ID NO: 2 or 17, and wherein
   the test plant is analyzed by using a PCR with a pair of primers selected from the primer group consisting of a primer having a base sequence of SEQ ID NO: 3, a primer having a base sequence of SEQ ID NO: 4, a primer having a base sequence of SEQ ID NO: 5, a primer having a base sequence of SEQ ID NO: 6, a primer having a base sequence of SEQ ID NO:7, a primer having a base sequence of SEQ ID NO: 8, a primer having a base sequence of SEQ ID NO: 9, a primer having a base sequence of SEQ ID NO: 10, a primer having a base sequence of SEQ ID NO: 11, a primer having a base sequence of SEQ ID NO: 12, a primer having a base sequence of SEQ ID NO: 13 and a primer having a base sequence of SEQ ID NO: 14; and
(II) selecting a plant with resistance or susceptibility to a 4-HPPD inhibitor based on the results of said analysis; and
(III) cultivating the plant with resistance or susceptibility to a 4-HPPD inhibitor;
wherein the test plant is a rice plant, the transgenic plant of claim 8, or a regenerated plant having the DNA selected from the (a) and (b) of the transgenic plant of claim 8.

14. A method for selecting a plant with resistance or susceptibility to a 4-HPPD inhibitor, wherein the method comprises:
(I) detecting, in a test plant, either the expression of a DNA sequence selected from the following (a) to (b) or detecting the molecular weight of an amplification product or an expression product of said DNA,
   (a) a DNA comprising a nucleotide sequence which encodes a protein comprising the amino acid sequence of SEQ ID NO: 2 or 17, and
   (b) a DNA comprising a nucleotide sequence which encodes a protein having an amino acid sequence having at least 90% sequence identity to the amino acid sequence of SEQ ID NO: 2 or 17, and wherein either the expression or the molecular weight is detected by using a PCR with a pair of primers selected from the primer group consisting of a primer having a base sequence of SEQ ID NO: 3, a primer having a base sequence of SEQ ID NO: 4, a primer having a base sequence of SEQ ID NO: 5, a primer having a base sequence of SEQ ID NO: 6, a primer having a base sequence of SEQ ID NO: 7, a primer having a base sequence of SEQ ID NO: 8, a primer having a base sequence of SEQ ID NO: 9, a primer having a base sequence of SEQ ID NO: 10, a primer having a base sequence of SEQ ID NO: 11, a primer having a base sequence of SEQ ID NO: 12, a primer having a base sequence of SEQ ID NO: 13 and a primer having a base sequence of SEQ ID NO: 14;

(II) selecting a plant with resistance or susceptibility to a 4-HPPD inhibitor based on the results of said analysis; and (III) cultivating the plant with resistance or susceptibility to a 4-HPPD inhibitor;

wherein the test plant is a rice plant, the transgenic plant of claim 8, or a regenerated plant having the DNA selected from the a) and b) of the transgenic plant of claim 8.

15. A method for breeding a plant having increased resistance to a 4-HPPD inhibitor, the method comprising:
(a) crossing a plant cultivar resistant to a 4-HPPD inhibitor with any cultivar; and
(b) determining whether individuals obtained by the crossing in step (a) have resistance or susceptibility to a 4-HPPD inhibitor, and selecting an individual determined to have resistance to the 4-HPPD inhibitor, by the method according to claim 13.

16. A method for breeding a plant having increased susceptibility to a 4-HPPD inhibitor, the method comprising:
(a) crossing a plant cultivar susceptible to a 4-HPPD inhibitor with any cultivar;
(b) determining whether individuals obtained by the crossing in step (a) have resistance or susceptibility to a 4-HPPD inhibitor, and selecting an individual determined to have susceptibility to the 4-HPPD inhibitor, by the method according to claim 13.

* * * * *